United States Patent
Hoveyda et al.

(10) Patent No.: US 11,020,730 B2
(45) Date of Patent: Jun. 1, 2021

(54) HALOGEN-CONTAINING METATHESIS CATALYSTS AND METHODS THEREOF

(71) Applicants: Massachusetts Institute of Technology, Cambridge, MA (US); Trustees of Boston College, Chestnut Hill, MA (US)

(72) Inventors: Amir H. Hoveyda, Lincoln, MA (US); Ming Joo Koh, Chestnut Hill, MA (US); Thach T. Nguyen, Newton, MA (US); Richard R. Schrock, Winchester, MA (US); Jakub Hyvl, Honolulu, HI (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 16/317,452

(22) PCT Filed: Jul. 14, 2017

(86) PCT No.: PCT/US2017/042169
§ 371 (c)(1),
(2) Date: Jan. 11, 2019

(87) PCT Pub. No.: WO2018/013943
PCT Pub. Date: Jan. 18, 2018

(65) Prior Publication Data
US 2019/0314799 A1   Oct. 17, 2019

Related U.S. Application Data

(60) Provisional application No. 62/363,066, filed on Jul. 15, 2016.

(51) Int. Cl.
| | | |
|---|---|---|
| *C07C 17/37* | (2006.01) |
| *B01J 31/22* | (2006.01) |
| *B01J 31/18* | (2006.01) |
| *C07C 41/18* | (2006.01) |
| *C07C 67/475* | (2006.01) |
| *C07C 209/68* | (2006.01) |
| *C07C 319/20* | (2006.01) |
| *C07D 209/08* | (2006.01) |
| *C07D 209/48* | (2006.01) |
| *C07D 211/18* | (2006.01) |
| *C07D 211/56* | (2006.01) |
| *C07D 307/79* | (2006.01) |
| *C07D 333/54* | (2006.01) |
| *C07F 7/08* | (2006.01) |
| *C07F 11/00* | (2006.01) |
| *C07F 17/02* | (2006.01) |

(52) U.S. Cl.
CPC ......... *B01J 31/2208* (2013.01); *B01J 31/181* (2013.01); *B01J 31/1805* (2013.01); *C07C 17/37* (2013.01); *C07C 41/18* (2013.01); *C07C 67/475* (2013.01); *C07C 209/68* (2013.01); *C07C 319/20* (2013.01); *C07D 209/08* (2013.01); *C07D 209/48* (2013.01); *C07D 211/18* (2013.01); *C07D 211/56* (2013.01); *C07D 307/79* (2013.01); *C07D 333/54* (2013.01); *C07F 7/083* (2013.01); *C07F 11/00* (2013.01); *C07F 17/02* (2013.01); *B01J 2231/543* (2013.01); *B01J 2531/64* (2013.01)

(58) Field of Classification Search
CPC .................................................. B01J 31/2208
USPC ........................................................ 546/12
See application file for complete search history.

(56) References Cited

U.S. PATENT DOCUMENTS

| | | | | |
|---|---|---|---|---|
| 7,169,541 B2* | 1/2007 | Hasegawa | ............ | C07D 307/00 430/270.1 |
| 7,576,099 B2* | 8/2009 | Kelly | ............ | C07C 233/65 514/311 |
| 2013/0116434 A1 | 5/2013 | Schrock et al. | | |
| 2016/0009746 A1 | 1/2016 | Schrock et al. | | |

FOREIGN PATENT DOCUMENTS

| | | |
|---|---|---|
| EP | 3023430 | 5/2016 |
| WO | 2009094201 | 7/2009 |
| WO | 2011097642 | 8/2011 |
| WO | 2012167171 | 12/2012 |
| WO | 2013070725 | 5/2013 |
| WO | 2014/139679 A2 | 9/2014 |
| WO | 2016073750 | 5/2016 |

OTHER PUBLICATIONS

Peryshkov American Chemical Society (2011), 133(51), 20754-20757.*
Gerber, Journal of the American Chemical Society (2011), 133(45), 18142-18144.*
Nomura, Organometallics (2012), 31(14), 5114-5120.*
Dorwald F. A. Side Reactions in Organic Synthesis, 2005, Wiley: VCH, Weinheim p. IX of Preface p. 1-15.*
Koh, Nature, Mar. 24, 2016, 531(7595): 459-465.*
Jeong, Organometallics 2015, 34, 4408-4418.*
International Search Report and Written Opinion dated Sep. 27, 2017 for International application PCT/US2017/042169.
(Continued)

*Primary Examiner* — Nizal S Chandrakumar
(74) *Attorney, Agent, or Firm* — Stoel Rives LLP

(57) ABSTRACT

The present disclosure provides compounds, compositions, and methods for preparing alkenyl halides and/or haloalkyl-substituted olefins with Z-selectivity. The methods are particularly useful for preparing alkenyl fluorides such as $CF_3$-substituted olefins by means of cross-metathesis reactions using halogen-containing molybdenum and tungsten complexes.

3 Claims, No Drawings

(56) References Cited

OTHER PUBLICATIONS

Extended European Search Report dated Jan. 24, 2020 for EP application 17828545.8.
Gerber, LCH., Investigations of Sterically Demanding Ligands in Molybdenum and Tungsten Monopyrrolide Monoalkoxide Catalysts for Olefin Metathesis, Aug. 12, 2013 (Aug. 12, 2013), pp. 1-217, Retrieved from the Internet <URL:https://dspace.mit.edu/bitstream/handle/1721.1/84373/867635229-MIT .pdf? sequence=2#page=59> [retrieved on Sep. 7, 2017].
International Search Report and Written Opinion dated Sep. 27, 2017 as received in PCT International Application No. PCT/US2017/042169 (20 pages).

* cited by examiner

HALOGEN-CONTAINING METATHESIS CATALYSTS AND METHODS THEREOF

CROSS-REFERENCE TO RELATED APPLICATIONS

This patent application is the U.S. National Stage filing under 35 U.S.C. 371 of International Patent Application No. PCT/US2017/042169 entitled HALOGEN-CONTAINING METATHESIS CATALYSTS AND METHODS THEREOF, filed on Jul. 14, 2017, which claims priority to U.S. Patent Application No. 62/363,066 entitled HALOGEN-CONTAINING METATHESIS CATALYSTS AND METHODS THEREOF, filed on Jul. 15, 2016, each of which is incorporated herein by reference in its entirety.

STATEMENT REGARDING FEDERALLY SPONSORED RESEARCH OR DEVELOPMENT

This invention was made with government support under Grant No. GM59426 awarded by the National Institute of Health. The US government has certain rights in the invention.

FIELD OF THE INVENTION

The present disclosure relates to halogen-containing metal complexes useful in cross metathesis reactions between an internal or terminal olefin with a halogen-containing olefin, and to metathesis reactions using the metal complexes.

BACKGROUND

Metal complexes useful in catalyzing metathesis reactions and metathesis reactions using the metal complexes are known.

E.g., WO 2009/094201, WO 2011/097642 and WO 2012/167171 disclose molybdenum- and tungsten-based catalysts of general formula

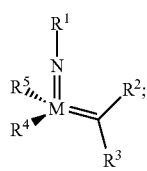

WO 2013/070725 discloses tungsten oxo alkylidene complexes of general formula

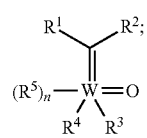

wherein residues $R^1$ to $R^5$ have the meaning as defined therein. The compounds are used to promote specific types of metathesis reactions resulting in specific olefins.

WO 2016/073750 discloses Mo-based catalysts in which $R^4$ is aryloxo and $R^5$ is a pyrrolide (so-called MAP catalysts). Such complexes have been used in cross-metathesis (CM) and ring-opening/cross-metathesis (ROCM) to introduce halo groups into olefins. Products were obtained in moderate to good yields and Z-selectivity.

Olefins containing halogen atoms, for example, organofluorine olefins, have wide applications and play important roles in the development of new pharmaceuticals and agrochemicals, as well as in materials science. Examples are e.g. the following known compounds:

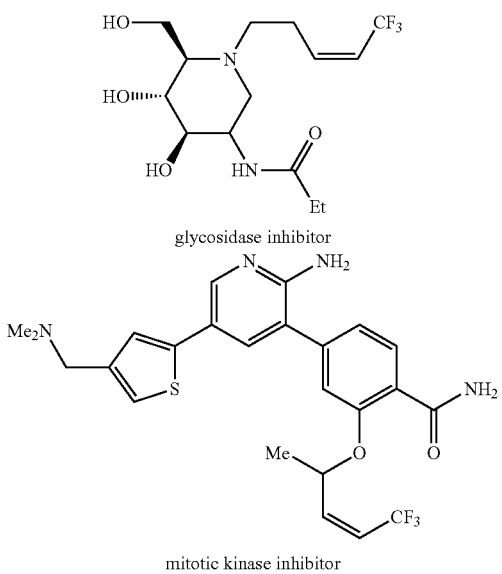

glycosidase inhibitor mitotic kinase inhibitor

Accordingly, halogenated olefins such as trifluoromethyl-substituted olefins, e.g. trifluoromethyl-substituted Z alkenes, may represent valuable compounds with considerable potential as drug candidates in medicinal chemistry. Nonetheless, the persisting lack of reliable, efficient and direct protocols for regioselective and stereoselective incorporation of a $CF_3$ group within an olefin group has restricted useful investigation of such important molecules.

OBJECT OF THE INVENTION

There is an ongoing need to provide improved catalysts which beneficially catalyze a method of making halogen-containing olefins such as fluorine-containing olefins, preferably perhaloalkyl-containing olefins such as perfluoroalkyl-containing olefins, e.g. $CF_3$-containing olefins, in particular in the Z-form and in high yield.

SUMMARY

The inventors discovered an entirely unprecedented and attractive approach to access Z-halo-substituted olefins, preferably Z-perhaloalkyl-substituted olefins such as Z-trifluoromethyl-substituted olefins. This approach entails catalytic olefin cross-metathesis (CM) between an internal or terminal olefin and a readily available and inexpensive halogen-containing olefin such as a fluorine-containing olefin, preferably an olefin bearing a perfluoroalky group such as a trifluoromethyl-substituted alkenyl reagent. Such catalytic CM reactions provide a compelling and strategically unique approach for site- and stereoselective late-stage incorporation of e.g. $CF_3$ units within alkene-tethered biologically and/or medicinally active entities. What is more, versatile reagents may become readily accessible that can then be utilized in a variety of manners to access a far wider range of products that contain e.g. Z-trifluoromethyl-substituted olefins.

The inventors discovered that molybdenum-based and tungsten-based oxygen-containing monohalide complexes or tungsten oxo-based monohalide complexes such as molybdenum monoaryloxide monohalide, tungsten monoaryloxide monohalide or tungsten oxo monoaryloxide monohalide complexes (in the following also termed as MAX complexes) afford e.g. Z-trifluoromethyl-substituted alkenes efficiently under mild conditions and with exceptional stereoselectivity. In particular the effectiveness of MAX complexes (containing a halide ligand) versus the closely related and much more extensively examined MAP variants (containing a pyrrolide ligand in place of said halide ligand) is entirely unexpected.

E.g., it has been surprisingly found that the catalysts according to the disclosure may promote cross-metathesis (CM) of olefins with halogen-containing olefins in high yields and Z-selectivity, wherein the analogous reaction using MAP catalysts is inferior.

Accordingly, the present disclosure provides metal complexes as catalysts for highly stereoselective synthesis of halogen- or haloalkyl-substituted olefins, in particular fluorine- or fluoroalkyl-substituted olefins, in particular Z olefins, via a metathesis reaction. The disclosure also provides a method of making such olefins.

According to a FIRST ASPECT, the present disclosure relates to a compound of formula I-a or I-b:

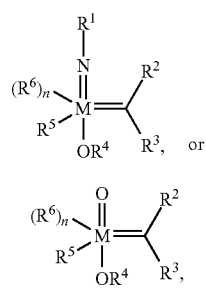

wherein:
M is molybdenum in the compound of formula I-a, or M is tungsten in the compound of formula I-b;
$R^1$ is a group selected from
$C_{1-20}$ aliphatic, or $C_{1-20}$ heteroaliphatic having 1-3 heteroatoms independently selected from nitrogen, oxygen, and sulfur; or
a 3-7 membered saturated carbocyclic ring, or an 8-10 membered bicyclic or tricyclic saturated ring; or
a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur;
each of $R^2$ and $R^3$ is independently hydrogen or a group selected from $C_{1-20}$ aliphatic, $C_{1-20}$ heteroaliphatic having 1-3 heteroatoms independently selected from nitrogen, oxygen, and sulfur, or aryl;

$R^4$ is a group selected from
$C_{1-20}$ aliphatic, or $C_{1-20}$ heteroaliphatic having 1-3 heteroatoms independently selected from nitrogen, oxygen, and sulfur; or
a 3-7 membered saturated carbocyclic ring, or an 8-10 membered bicyclic or tricyclic saturated ring; or
a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur, or an 8-14 membered bicyclic or tricyclic heteroaryl ring having 1-5 heteroatoms independently selected from nitrogen, oxygen, and sulfur; and
triaryl silyl;
$R^5$ is halogen;
each $R^6$ is independently a neutral ligand, preferably selected from an ether, a nitrile, a pyridine, an amine, and a phosphine; and
n is 0-2;
wherein
each of $R^1$, $R^4$, or $C_{1-20}$ aliphatic, $C_{1-20}$ heteroaliphatic or aryl as defined for $R^2$ and $R^3$ may be optionally independently substituted with one or more of halogen, or R', —OR', —SR', —OSi(R')$_3$, —N(R')$_2$, —NR'C(O)R', or —NR'OR', wherein
R' is independently hydrogen, $C_{1-20}$ aliphatic, $C_{1-20}$ heteroaliphatic having 1-3 heteroatoms independently selected from nitrogen, oxygen, and sulfur, a 3-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur;
with the proviso that the compound of formula I-a is not Mo(NAr*)(CHCMe$_2$Ph)Cl(OAr*)(py);

Mo(NAr*)(CHCMe$_2$Ph)Cl(O-t-Bu)(py);

Mo(NAr*)(CHCMe$_2$Ph)Cl[OCMe(CF$_3$)$_2$](py);

Mo(NAr*)(CHCMe$_2$Ph)Cl(OAr')(py);

and the compound of formula I-b is not

W(O)(CH-t-Bu)Cl(OHIPT)(PMe$_2$Ph);

W(O)(CH-t-Bu)Cl(OHMT)(PMe$_2$Ph);

W(O)(CHCMe$_2$Ph)Cl(OHMT)(PMe$_2$Ph);

W(O)(CHCMe$_2$Ph)Cl(ODFT)(PMe$_2$Ph);

W(O)(CHCMe$_2$Ph)Cl(OTPP)(PMe$_2$Ph);

W(O)(CHCMe$_2$Ph)Cl(OdAdP)(PMe$_2$Ph);

W(O)(CHCMe$_2$Ph)Cl(ODBMP)(PMe$_2$Ph);

wherein Ar* is 2,6-dimesitylphenyl (HMT); Ar' is 2,6-dimethylphenyl; HIPT is 2,6-(2,4,6-(i-Pr)$_3$C$_6$H$_2$)$_2$C$_6$H$_3$, DFT is 2,6-di(pentafluorophenyl)phenyl; TPP is 2,3,5,6-tetraphenylphenyl; dAdP is 2,6-diadamantylphenyl; DBMP is 4-methyl-2,6-di(diphenylmethyl)phenyl; Me is methyl; Ph is phenyl; Bu is butyl; and py is pyridine.

In an embodiment, the present disclosure relates to a compound of formula I-a or I-b:

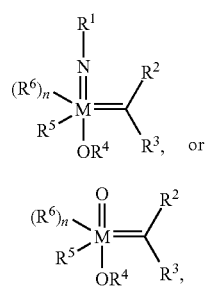

wherein:
M is molybdenum in the compound of formula I-a, or M is tungsten in the compound of formula I-b;
R$^1$ is a group selected from
C$_{1-20}$ aliphatic; or
a 5-7 membered saturated carbocyclic ring, or an 8-10 membered bicyclic or tricyclic saturated ring; or
an aryl ring;
each of R$^2$ and R$^3$ is independently hydrogen or a group selected from C$_{1-20}$ aliphatic or aryl;
R$^4$ is a group selected from
C$_{1-20}$ aliphatic, or C$_{1-20}$ heteroaliphatic having 1-3 heteroatoms independently selected from nitrogen and oxygen; or
a 5-7 membered saturated carbocyclic ring, or an 8-10 membered bicyclic or tricyclic saturated ring; or
an aryl ring;
R$^5$ is chlorine or bromine;
each R$^6$ is independently a neutral ligand, preferably selected from a nitrile, a pyridine and a phosphine; and
n is 0-2;
wherein
each of R$^1$, R$^4$, or C$_{1-20}$ aliphatic or aryl as defined for R$^2$ and R$^3$ may be independently substituted with one or more of halogen, or R', —OR', —SR', —OSi(R')$_3$, —N(R')$_2$, —NR'C(O)R', or —NR'OR', wherein
R' is independently hydrogen, C$_{1-20}$ aliphatic, C$_{1-20}$ heteroaliphatic having 1-3 heteroatoms independently selected from nitrogen and oxygen, a 5-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur;
with the proviso that the compound of formula I-a is not Mo(NAr*)(CHCMe$_2$Ph)Cl(OAr*)(py);

Mo(NAr*)(CHCMe$_2$Ph)Cl(O-$t$-Bu)(py);

Mo(NAr*)(CHCMe$_2$Ph)Cl[OCMe(CF$_3$)$_2$](py);

Mo(NAr*)(CHCMe$_2$Ph)Cl(OAr')(py);

and the compound of formula I-b is not

W(O)(CH-$t$-Bu)Cl(OHIPT)(PMe$_2$Ph);

W(O)(CH-$t$-Bu)Cl(OHMT)(PMe$_2$Ph);

W(O)(CHCMe$_2$Ph)Cl(OHMT)(PMe$_2$Ph);

W(O)(CHCMe$_2$Ph)Cl(ODFT)(PMe$_2$Ph);

W(O)(CHCMe$_2$Ph)Cl(OTPP)(PMe$_2$Ph);

W(O)(CHCMe$_2$Ph)Cl(OdAdP)(PMe$_2$Ph);

W(O)(CHCMe$_2$Ph)Cl(ODBMP)(PMe$_2$Ph);

wherein Ar* is 2,6-dimesitylphenyl (HMT); Ar' is 2,6-dimethylphenyl; HIPT is 2,6-(2,4,6-(i-Pr)$_3$C$_6$H$_2$)$_2$C$_6$H$_3$, DFT is 2,6-di(pentafluorophenyl)phenyl; TPP is 2,3,5,6-tetraphenylphenyl; dAdP is 2,6-diadamantylphenyl; DBMP is 4-methyl-2,6-di(diphenylmethyl)phenyl; Me is methyl; Ph is phenyl; Bu is butyl; and py is pyridine.

In a further embodiment, the present disclosure relates to a compound of formula I-a or I-b:

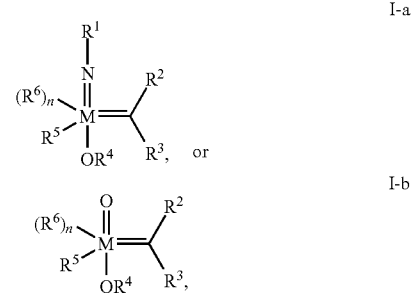

wherein:
M is molybdenum in the compound of formula I-a, or M is tungsten in the compound of formula I-b;
R$^1$ is a group selected from adamantyl, t-butyl, and phenyl;
each of R$^2$ and R$^3$ is independently hydrogen or C(CH$_3$)$_3$ or C(CH$_3$)$_2$C$_6$H$_5$ or phenyl;
R$^4$ is a group selected from
an aryl ring;
R$^5$ is chlorine or bromine;
each R$^6$ is independently a neutral ligand selected from a nitrile, a pyridine and a phosphine; and
n is 0-2;
wherein
each of phenyl as defined for R$^1$, R$^2$ and R$^3$ and aryl as defined for R$^4$ may be independently substituted with one or more of halogen, or R', —OR', —SR', —OSi(R')$_3$, —N(R')$_2$, —NR'C(O)R', or —NR'OR', wherein
R' is independently hydrogen, C$_{1-20}$ aliphatic, C$_{1-20}$ heteroaliphatic having 1-3 heteroatoms independently selected from nitrogen and oxygen, a 5-6 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur;
with the proviso that the compound of formula I-a is not Mo(NAr*)(CHCMe$_2$Ph)Cl(OAr*)(py);

Mo(NAr*)(CHCMe$_2$Ph)Cl(O-$t$-Bu)(py);

Mo(NAr*)(CHCMe$_2$Ph)Cl[OCMe(CF$_3$)$_2$](py);

Mo(NAr*)(CHCMe$_2$Ph)Cl(OAr')(py);

and the compound of formula I-b is not

W(O)(CH-$t$-Bu)Cl(OHIPT)(PMe$_2$Ph);

W(O)(CH-$t$-Bu)Cl(OHMT)(PMe$_2$Ph);

W(O)(CHCMe$_2$Ph)Cl(OHMT)(PMe$_2$Ph);

W(O)(CHCMe$_2$Ph)Cl(ODFT)(PMe$_2$Ph);

W(O)(CHCMe$_2$Ph)Cl(OTPP)(PMe$_2$Ph);

W(O)(CHCMe$_2$Ph)Cl(OdAdP)(PMe$_2$Ph);

W(O)(CHCMe$_2$Ph)Cl(ODBMP)(PMe$_2$Ph);

wherein Ar* is 2,6-dimesitylphenyl (HMT); Ar' is 2,6-dimethylphenyl; HIPT is 2,6-(2,4,6-(i-Pr)$_3$C$_6$H$_2$)$_2$C$_6$H$_3$, DFT is 2,6-di(pentafluorophenyl)phenyl; TPP is 2,3,5,6-tetraphenylphenyl; dAdP is 2,6-diadamantylphenyl; DBMP is 4-methyl-2,6-di(diphenylmethyl)phenyl; Me is methyl; Ph is phenyl; Bu is butyl; and py is pyridine.

In a further embodiment, the present disclosure relates to a compound of formula I-c:

I-c $$\begin{array}{c} R^1 \\ | \\ N \\ || \\ (R^6)_n - M - R^2 \\ R^5 / | \backslash \\ OR^4 \quad R^3, \end{array}$$

wherein:
M is tungsten;
R$^1$ is a group selected from adamantyl, t-butyl, and phenyl;
each of R$^2$ and R$^3$ is independently hydrogen or C(CH$_3$)$_3$ or C(CH$_3$)$_2$C$_6$H$_5$ or phenyl;
R$^4$ is a group selected from
an aryl ring;
R$^5$ is chlorine or bromine;
each R$^6$ is independently a neutral ligand selected from a nitrile, a pyridine and a phosphine; and n is 0-2;
wherein
each of phenyl as defined for R$^1$, R$^2$ and R$^3$ and aryl as defined for R$^4$ may be independently substituted with one or more of halogen, or R', —OR', —SR', —OSi(R')$_3$, —N(R')$_2$, —NR'C(O)R', or —NR'OR', wherein
R' is independently hydrogen, C$_{1-20}$ aliphatic, C$_{1-20}$ heteroaliphatic having 1-3 heteroatoms independently selected from nitrogen and oxygen, a 5-6 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur;
with the proviso that the compound of formula I-c is not W(N-$t$-Bu)(CH-$t$-Bu)Cl(OHMT)(py);

wherein HMT is 2,6-dimesitylphenyl and py is pyridine.
Further embodiments are specified in the attached claims depending thereon.

According to a SECOND ASPECT, the present disclosure provides a method for performing a metathesis reaction, comprising:
reacting a first species comprising a first double bond with a second species comprising a second double bond in the presence of a compound of formula I-a or I-b, or a composition comprising a compound of formula I-a or I-b, to provide at least one product comprising a third double bond, wherein:
a carbon atom of the first double bond in the first species is substituted with a first substituent selected from halogen and optionally substituted C$_{1-6}$ haloalkyl; and
the third double bond in the at least one product comprises a carbon atom of the first double bond and a carbon atom of the second double bond, wherein the carbon atom of the first double bond is substituted with the first substituent;
wherein the compound of formula I-a or I-b is:

I-a $$\begin{array}{c} R^1 \\ | \\ N \\ || \\ (R^6)_n - M - R^2 \\ R^5 / | \backslash \\ OR^4 \quad R^3, \quad \text{or} \end{array}$$

I-b $$\begin{array}{c} O \\ || \\ (R^6)_n - M - R^2 \\ R^5 / | \backslash \\ OR^4 \quad R^3, \end{array}$$

wherein:
M is molybdenum in the compound of formula I-a, or M is tungsten in the compound of formula I-b;
R$^1$ is a group selected from
C$_{1-20}$ aliphatic, or C$_{1-20}$ heteroaliphatic having 1-3 heteroatoms independently selected from nitrogen, oxygen, and sulfur; or
a 3-7 membered saturated carbocyclic ring, or an 8-10 membered bicyclic or tricyclic saturated ring; or a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur;

each of $R^2$ and $R^3$ is independently hydrogen or a group selected from $C_{1-20}$ aliphatic, $C_{1-20}$ heteroaliphatic having 1-3 heteroatoms independently selected from nitrogen, oxygen, and sulfur, or aryl;

$R^4$ is a group selected from $C_{1-20}$ aliphatic, or $C_{1-20}$ heteroaliphatic having 1-3 heteroatoms independently selected from nitrogen, oxygen, and sulfur; or a 3-7 membered saturated carbocyclic ring, or an 8-10 membered bicyclic or tricyclic saturated ring; or a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur, or an 8-14 membered bicyclic or tricyclic heteroaryl ring having 1-5 heteroatoms independently selected from nitrogen, oxygen, and sulfur;

triaryl silyl;

$R^5$ is halogen;

each $R^6$ is independently a neutral ligand, preferably selected from an ether, a nitrile, a pyridine, an amine, and a phosphine; and n is 0-2;

wherein each of $R^1$, $R^4$, or $C_{1-20}$ aliphatic, $C_{1-20}$ heteroaliphatic or aryl as defined for $R^2$ and $R^3$ may be independently substituted with one or more of halogen, or R', —OR', —SR', —OSi(R')$_3$, —N(R')$_2$, —NR'C(O)R', or —NR'OR', wherein R' is independently hydrogen, $C_{1-20}$ aliphatic, $C_{1-20}$ heteroaliphatic having 1-3 heteroatoms independently selected from nitrogen, oxygen, and sulfur, a 3-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein:

two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

In an embodiment, the metathesis reaction is promoted by a compound of formula I-a or I-b:

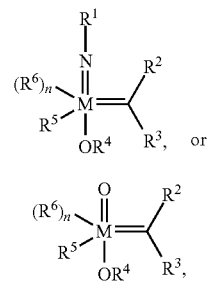
I-a

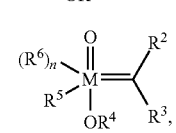
I-b wherein:

M is molybdenum in the compound of formula I-a, or M is tungsten in the compound of formula I-b;

$R^1$ is a group selected from $C_{1-20}$ aliphatic; or a 5-7 membered saturated carbocyclic ring, or an 8-10 membered bicyclic or tricyclic saturated ring; or an aryl ring;

each of $R^2$ and $R^3$ is independently hydrogen or a group selected from $C_{1-20}$ aliphatic or aryl;

$R^4$ is a group selected from $C_{1-20}$ aliphatic, or $C_{1-20}$ heteroaliphatic having 1-3 heteroatoms independently selected from nitrogen and oxygen; or a 5-7 membered saturated carbocyclic ring, or an 8-10 membered bicyclic or tricyclic saturated ring; or an aryl ring;

$R^5$ is chlorine or bromine;

each $R^6$ is independently a neutral ligand, preferably selected from a nitrile, a pyridine and a phosphine; and n is 0-2;

wherein each of $R^1$, $R^4$, or $C_{1-20}$ aliphatic or aryl as defined for $R^2$ and $R^3$ may be independently substituted with one or more of halogen, or R', —OR', —SR', —OSi(R')$_3$, —N(R')$_2$, —NR'C(O)R', or —NR'OR', wherein R' is independently hydrogen, $C_{1-20}$ aliphatic, $C_{1-20}$ heteroaliphatic having 1-3 heteroatoms independently selected from nitrogen and oxygen, a 5-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein:

two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

In a further embodiment, the method is promoted by a compound of formula I-a or I-b:

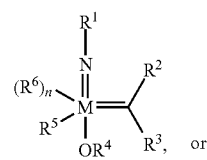
I-a

-continued

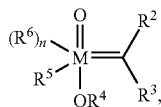

I-b wherein:
M is molybdenum in the compound of formula I-a, or M is tungsten in the compound of formula I-b;
$R^1$ is a group selected from adamantyl, t-butyl, and phenyl;
each of $R^2$ and $R^3$ is independently hydrogen or $C(CH_3)_3$ or $C(CH_3)_2C_6H_5$ or phenyl;
$R^4$ is a group selected from
an aryl ring;
$R^5$ is chlorine or bromine;
each $R^6$ is independently a neutral ligand selected from a nitrile, a pyridine and a phosphine; and
n is 0-2;
wherein
each of phenyl as defined for $R^1$, $R^2$ and $R^3$ and aryl as defined for $R^4$ may be independently substituted with one or more of halogen, or R', —OR', —SR', —OSi(R')$_3$, —N(R')$_2$, —NR'C(O)R', or —NR'OR', wherein
R' is independently hydrogen, $C_{1-20}$ aliphatic, $C_{1-20}$ heteroaliphatic having 1-3 heteroatoms independently selected from nitrogen and oxygen, a 5-6 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

In a further embodiment, the method is promoted by a compound of formula I-c:

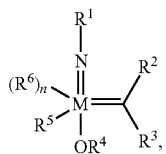

I-c wherein:
M is tungsten;
$R^1$ is a group selected from adamantyl, t-butyl, and phenyl;
each of $R^2$ and $R^3$ is independently hydrogen or $C(CH_3)_3$ or $C(CH_3)_2C_6H_5$ or phenyl;
$R^4$ is a group selected from
an aryl ring;
$R^5$ is chlorine or bromine;
each $R^6$ is independently a neutral ligand selected from a nitrile, a pyridine and a phosphine; and
n is 0-2;
wherein
each of phenyl as defined for $R^1$, $R^2$ and $R^3$ and aryl as defined for $R^4$ may be independently substituted with one or more of halogen, or R', —OR', —SR', —OSi(R')$_3$, —N(R')$_2$, —NR'C(O)R', or —NR'OR', wherein
R' is independently hydrogen, $C_{1-20}$ aliphatic, $C_{1-20}$ heteroaliphatic having 1-3 heteroatoms independently selected from nitrogen and oxygen, a 5-6 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

Further embodiments of the method according to the disclosure are specified in the attached claims depending thereon.

Preferably, said metathesis reaction provides an olefin having Z-selectivity, i.e. the product comprising the third double bond.

DETAILED DESCRIPTION

Definitions

The following terms in quotation marks are used in the meaning of the disclosure.

The term "aliphatic" or "aliphatic group" means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle", "cycloaliphatic" or "cycloalkyl"), that has a single point of attachment to the rest of the molecule. Unless otherwise specified, aliphatic groups contain 1-20 aliphatic carbon atoms or 1-10 aliphatic carbon atoms or 1-5 aliphatic carbon atoms. In yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic" refers to saturated cyclic aliphatic monocyclic, bicyclic, or polycyclic ring systems having from 3 to 14 members, wherein the aliphatic ring system is optionally substituted as defined herein. Cycloaliphatic groups include, without limitation, cyclopropyl, cyclobutyl, cyclopentyl, cycloheptyl, cyclooctyl, norbornyl, and adamantyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated, that has a single point of attachment to the rest of the molecule, or a $C_9$-$C_{16}$ tricyclic hydrocarbon that is completely saturated, that has a single point of attachment to the rest of the molecule.

The term "alkyl" may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. A straight chain or branched chain alkyl has 1-20 carbon atoms in its backbone (e.g., $C_1$-$C_{20}$ for straight chain, $C_2$-$C_{20}$ for branched chain), and alternatively, 1-10. In some embodiments, a cycloalkyl ring has from 3-10 carbon atoms in their ring structure where such rings are monocyclic or bicyclic, and alternatively 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

The term "heteroalkyl" refers to alkyl groups in which one or more carbon atoms is/are replaced with a heteroatom (e.g., oxygen, nitrogen, sulfur, silicon, phosphorus), preferably nitrogen, oxygen, and sulfur, more preferably nitrogen and oxygen. Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl" "aralkoxy" or "aryloxyalkyl" refers to monocyclic or bicyclic or tricyclic or polycyclic ring systems having a total of five to twenty-eight ring members, wherein at least one ring in the system is aromatic and wherein each ring in the system contains 3 to 7 ring members. One example is a bicyclic 10 membered aryl ring. The term "aryl" may be used interchangeably with the term "aryl ring". The term refers to an aromatic ring system which includes, but not limited to, phenyl, biphenyl, naphthyl, tetrahydronaphthyl, binaphthyl, a bi(tetrahydronaphthyl) such as 1,1'-bi(tetrahydronaphthyl), anthracyl, which may bear one or more substituents as defined below. Accordingly, also included within the scope of the term "aryl" is a group in which an aromatic ring is fused to one or more non-aromatic rings. Also included within the scope of the term "aryl" is a group in which an aromatic ring is fused to one or more non-aromatic rings, such as indanyl, phthalimidyl, naphthimidyl, phenanthridinyl, or tetrahydronaphthyl.

The terms "heteroaryl" and "heteroar-" used alone or as part of a larger moiety, e.g., "heteroaralkyl" or "heteroaralkoxy" refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl. The terms "heteroaryl" and "heteroar-" also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group" or "heteroaromatic" any of which terms include rings that are optionally substituted. Suitable substituents are defined below. The term "heteroaralkyl" refers to an alkyl group substituted by a heteroaryl, wherein the alkyl and heteroaryl portions independently are optionally substituted.

The terms "heterocycle", "heterocyclyl", "heterocyclic radical" and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or aromatic heterocyclic radicals include tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety" and "heterocyclic radical" are used interchangeably, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "heteroatom" means one or more of oxygen, sulfur, nitrogen, boron, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "halogen" means F, Cl, Br, or I.

The term "haloalkyl" means an alkyl group wherein one or more hydrogen atoms are independently replaced with one or more halogen atoms. The term encompasses perhaloalkyl groups, i.e. alkyl groups in which all hydrogen atoms are replaced with halogen atoms such as perfluoroalkyl groups.

The compounds, respectively residues $R^1$, $R^2$, $R^3$, $R^4$, $R^5$, $R^6$ of the compounds according to the disclosure, may "optionally be substituted". In general, the term "substituted" whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of chemically feasible compounds.

Suitable monovalent substituents on a substitutable carbon atom of an "optionally substituted" group are independently halogen; —(CH$_2$)$_{0-4}$R$^\circ$, —(CH$_2$)$_{0-4}$OR$^\circ$, —O(CH$_2$)$_{0-4}$R$^\circ$, —O—(CH$_2$)$_{0-4}$(O)OR$^\circ$; —(CH$_2$)$_{0-4}$CH(OR$^\circ$)$_2$, —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$(O)R$^\circ$; —C(S)R$^\circ$; —(CH$_2$)$_{0-4}$C(O)OR$^\circ$; —(CH$_2$)$_{0-4}$(O)SR$^\circ$; —(CH$_2$)$_{0-4}$(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; —SiR$^\circ_3$; —OSiR$^\circ_3$; —(C$_{1-4}$ straight or branched)alkylene)O—N(R$^\circ_2$; or —(C$_{1-4}$ straight or branched)alkylene)C(O)O—N(R$^\circ_2$, wherein each R$^\circ$ may be substituted as defined below and is independently hydrogen, C$_{1-6}$ aliphatic; —CH$_2$Ph; —O(CH$_2$)$_{0-1}$Ph; —CH$_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated ring or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated ring or aryl ring having 0-4 heteroatoms independently selected from nitrogen, oxygen, and sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$, wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated ring or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated ring, or aryl ring having 0-4 heteroatoms independently selected from nitrogen, oxygen, and sulfur.

The term "chiral" refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" refers to a molecule that is superimposable with its mirror image. Typically, achiral molecules possess a plane of symmetry.

The term "neutral ligand" encompasses a neutral molecule which binds to M to form a coordination complex. The ligand may be either monodentate, bidentate, tridentate or polydentate. In some embodiments, two or more monodentate ligands are taken together to form a polydentate ligand. In one embodiment, a ligand is a nitrogen-containing ligand. In another embodiment, a ligand is an oxygen-containing ligand. In another embodiment, a ligand is a phosphorus-containing ligand. Preferably, the ligand binds via the heteroatom to M, i.e. via N or O or P. In another embodiment, a ligand comprises an unsaturated bond, and the unsaturated bond is coordinated to a metal. In some embodiments, a ligand comprises a carbon-carbon double bond, and the double bond is coordinated to a metal. In some embodiments, a ligand is an olefin. When an olefin double bond is coordinated to a metal, the chemical bonding between the olefin and the metal can either be depicted as a 3-membered ring wherein the ring members comprises the metal and both carbon atoms of the double bond, or as a single bond between the metal and the double bond.

The term "protecting group" refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. Protecting groups (and associated protected moieties) are described in detail below.

A "Si protecting group" is a protecting group comprising a Si atom, such as Si-trialkyl (e.g., trimethylsilyl, tributylsilyl, t-butyldimethylsilyl=TBS), Si-triaryl, Si-alkyl-diphenyl (e.g., t-butyldiphenylsilyl), or Si-aryl-dialkyl (e.g., Siphenyldialkyl). Generally, a Si protecting group is attached to an oxygen atom.

Protected hydroxyl groups are well known in the art. Examples of suitable esters include formates, acetates, propionates, pentanoates, crotonates, and benzoates. Examples of suitable carbonates include 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art. Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art. Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art. Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art. Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this disclosure. Such compounds are useful, for example, as analytical tools or probes in biological assays.

The term "electron-withdrawing group" refers to an atom or group that draws electron density from a neighboring atom or group, usually by resonance and/or inductive effects. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —NO$_2$, —S(O)—, and —S(O)$_2$—. Hydrogen is used as reference and regarded as having no effect.

The singular forms "a", "an", and "the" include the plural reference unless the context clearly indicates otherwise. Thus, for example, a reference to "a compound" includes a plurality of such compounds.

Catalysts and Method According to the Disclosure

According to the FIRST ASPECT, the disclosure relates to a compound of formula I-a or I-b:

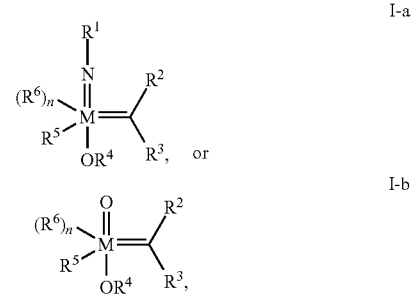

wherein:

M is molybdenum in the compound of formula I-a, or M is tungsten in the compound of formula I-b, and wherein residues $R^1$ to $R^6$ are defined in the SUMMARY section; with the proviso that the compound of formula I-a is not Mo(NAr*)(CHCMe₂Ph)Cl(OAr*)(py);

Mo(NAr*)(CHCMe₂Ph)Cl(O-t-Bu)(py);

Mo(NAr*)(CHCMe₂Ph)Cl[OCMe(CF₃)₂](py);

Mo(NAr*)(CHCMe₂Ph)Cl(OAr')(py);

and the compound of formula I-b is not

W(O)(CH-t-Bu)Cl(OHIPT)(PMe₂Ph);

W(O)(CH-t-Bu)Cl(OHMT)(PMe₂Ph);

W(O)(CHCMe₂Ph)Cl(OHMT)(PMe₂Ph);

W(O)(CHCMe₂Ph)Cl(ODFT)(PMe₂Ph);

W(O)(CHCMe₂Ph)Cl(OTPP)(PMe₂Ph);

W(O)(CHCMe₂Ph)Cl(OdAdP)(PMe₂Ph);

W(O)(CHCMe₂Ph)Cl(ODBMP)(PMe₂Ph);

wherein Ar* is 2,6-dimesitylphenyl (HMT); Ar' is 2,6-dimethylphenyl; HIPT is 2,6-(2,4,6-(i-Pr)₃C₆H₂)₂C₆H₃; DFT is 2,6-di(pentafluorophenyl)phenyl; TPP is 2,3,5,6-tetraphenylphenyl; dAdP is 2,6-diadamantylphenyl; DBMP is 4-methyl-2,6-di(diphenylmethyl)phenyl; Me is methyl; Ph is phenyl; Bu is butyl; and py is pyridine.

In its broadest meaning, $R^1$ is an optionally substituted group selected from $C_{1-20}$ aliphatic, or $C_{1-20}$ heteroaliphatic having 1-3 heteroatoms independently selected from nitrogen, oxygen, and sulfur; or
a 3-7 membered saturated carbocyclic ring, or an 8-10 membered bicyclic or tricyclic saturated ring; or
a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur.

In one embodiment, $R^1$ is optionally substituted $C_{1-20}$ aliphatic, or optionally substituted $C_{1-20}$ cycloaliphatic, or optionally substituted $C_{1-20}$ cycloalkyl, or optionally substituted $C_{1-20}$ polycyclic cycloalkyl. In one embodiment, $R^1$ is optionally substituted $C_{1-12}$ aliphatic, or optionally substituted $C_{1-12}$ cycloaliphatic, or optionally substituted $C_{1-12}$ cycloalkyl. In one embodiment, $R^1$ is optionally substituted adamantyl, preferably 1-adamantyl. In one embodiment, $R^1$ is optionally substituted $C_{1-6}$ aliphatic, or optionally substituted $C_{1-6}$ alkyl. In some embodiments, $R^1$ is optionally substituted hexyl, pentyl, butyl, propyl, ethyl or methyl. In some embodiments, $R^1$ is isopropyl. In some embodiments, $R^1$ is tert-butyl.

In another embodiment, $R^1$ is an optionally substituted $C_{1-20}$ aliphatic, wherein $R^1$ is a tertiary substituent. In some embodiments, $R^1$ is an optionally substituted $C_{1-20}$ cycloaliphatic, wherein $R^1$ is a tertiary substituent. In some embodiments, $R^1$ is an optionally substituted $C_{1-20}$ cycloalkyl, wherein $R^1$ is a tertiary substituent. In one embodiment, $R^1$ is tert.-butyl or 1-adamantyl.

In another embodiment, $R^1$ is optionally substituted phenyl. In some embodiments, $R^1$ is mono-, di-, tri-, tetra- or penta-substituted phenyl; or $R^1$ is monosubstituted phenyl; or $R^1$ is 2,6-disubstituted phenyl; or $R^1$ is tri-substituted phenyl; or $R^1$ is tetra-substituted phenyl; or $R^1$ is penta-substituted phenyl. In one embodiment, a substituent is a halogen. In one embodiment, a substituent is —F, and $R^1$ is phenyl substituted with one or more —F. In another embodiment, $R^1$ is pentafluorophenyl. In other embodiments, a substituent is optionally substituted $C_{1-4}$ aliphatic. In some embodiments, $R^1$ is phenyl disubstituted with halogen or $C_{1-4}$ aliphatic. Such $R^1$ groups include, but are not limited to, 2,6-dichlorophenyl, 2,6-dibromophenyl, 2,6-dimethylphenyl, 2,6-di-tert-butylphenyl, and 2,6-diisopropylphenyl. In some embodiments, $R^1$ is substituted phenyl, wherein at least one substituent is an electron-withdrawing group.

Each of $R^2$ and $R^3$ is independently hydrogen or a group selected from $C_{1-20}$ aliphatic, $C_{1-20}$ heteroaliphatic having 1-3 heteroatoms independently selected from nitrogen, oxygen, and sulfur, or aryl, wherein $C_{1-20}$ aliphatic, $C_{1-20}$ heteroaliphatic or aryl as defined for $R^2$ and $R^3$ may be independently substituted with one or more of halogen, or R', —OR', —SR', —OSi(R')₃, —N(R')₂, —NR'C(O)R', or —NR'OR'.

Each of $R^2$ and $R^3$ may be independently R', —OR', —SR', —N(R')₂, —C(O)N(R')₂, provided that $R^2$ and $R^3$ are not simultaneously hydrogen, wherein R' is independently hydrogen or an optionally substituted group selected from $C_{1-20}$ aliphatic, $C_{1-20}$ heteroaliphatic having 1-3 heteroatoms, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered, saturated ring, or aryl ring having 1-4 heteroatoms independently selected from nitrogen, oxygen, and sulfur.

In an embodiment, one of $R^2$ and $R^3$ is hydrogen and the other is optionally substituted $C_{1-6}$ alkyl. In another embodiment, one of $R^2$ and $R^3$ is hydrogen and the other is optionally substituted methyl. In some embodiments, one of $R^2$ and $R^3$ is hydrogen and the other is —C(Me)₃ or is —C(Me)₂Ph or is aryl such as —C₆H₅ or aryl such as —C₆H₅ bearing an ether group in ortho-position. Examples are 2-methoxyphenyl or 2-isopropoxyphenyl.

$R^4$ may be aryl, optionally substituted, or an optionally substituted group selected from —Ar, —Ar', $C_{1-20}$ aliphatic, $C_{1-20}$ heteroaliphatic having 1-3 heteroatoms independently selected from nitrogen, oxygen, and sulfur, phenyl, a 3-7 membered saturated carbocyclic ring, an 8-10 membered bicyclic saturated ring or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In one embodiment, $R^4$ is an optionally substituted group selected from —Ar, —Ar', $C_{1-20}$ heteroaliphatic having 1-3 heteroatoms independently selected from nitrogen, oxygen, and sulfur, phenyl, a 3-7 membered saturated carbocyclic ring, an 8-10 membered bicyclic saturated ring or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In one embodiment, $R^4$ is an optionally substituted group selected from —Ar, —Ar', $C_{1-20}$ aliphatic, $C_{1-20}$ heteroaliphatic having 1-3 heteroatoms independently selected from nitrogen, oxygen, and sulfur, a 3-7 membered saturated carbocyclic ring, an 8-10 membered bicyclic saturated ring or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In a further embodiment, $R^4$ is an optionally substituted group selected from —Ar, —Ar', $C_{1-20}$ heteroaliphatic having 1-3 heteroatoms independently selected from nitrogen, oxygen, and sulfur, a 3-7 membered saturated carbocyclic ring, an 8-10 membered bicyclic saturated ring or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In one embodiment, $R^4$ is an optionally substituted group selected from —Ar, —Ar', phenyl, an 8-10 membered bicyclic aryl ring, a 5-6 membered monocyclic heteroaryl ring having 1-4 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In an embodiment, $R^4$ is an optionally substituted group selected from —Ar and —Ar'. In one embodiment, $R^4$ is —Ar. In another embodiment, $R^4$ is —Ar'.

Ar is of the following structure:

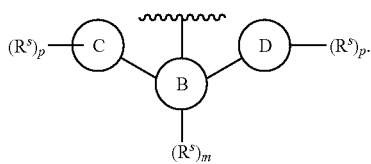

$R^s$ is independently from each other halogen, R', —OR', —SR', —OSi(R')$_3$, —N(R')$_2$, —NR'C(O)R', or —NR'OR', wherein R' is $C_{1-20}$ aliphatic, $C_{1-20}$ heteroaliphatic having 1-3 heteroatoms, a 3-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

As defined, m is 0-3 such as 0, 1, 2 or 3; and each p is independently from one another 0-6 such as 0, 1, 2, 3, 4, 5 or 6.

In one embodiment, Ring B is an optionally substituted group selected from phenyl or a 5-6 membered monocyclic heteroaryl ring having 1-4 heteroatoms independently selected from nitrogen, oxygen, and sulfur. In some embodiments, Ring B is of the following structure:

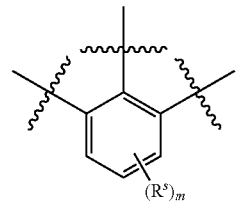

wherein $R^x$ and m are as defined above and described herein. In some embodiments, Ring B is optionally substituted phenyl. In some embodiments, m=0. In some embodiments, Ring B is optionally substituted

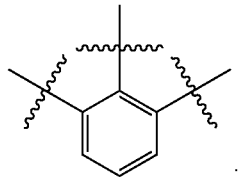 [SMILES: *c1cccc(*)c1*]

In another embodiment, Ring B is an optionally substituted 5-6 membered monocyclic heteroaryl ring having 1-4 heteroatoms independently selected from nitrogen, oxygen, and sulfur. In some embodiments, Ring B is an optionally substituted 5-membered monocyclic heteroaryl ring having 1-4 heteroatoms independently selected from nitrogen, oxygen, and sulfur, and m is 0-2. In some embodiments, Ring B is an optionally substituted 6-membered monocyclic heteroaryl ring having 1-4 heteroatoms independently selected from nitrogen, oxygen, and sulfur, and m is 0-3.

In a further embodiment, Ring B is a 5-6 membered monocyclic heteroaryl ring having 1-4 heteroatoms independently selected from nitrogen, oxygen, and sulfur. In some embodiments, Ring B is a 5-6 membered monocyclic heteroaryl ring having 1-2 heteroatoms independently selected from nitrogen, oxygen, and sulfur.

In some embodiments, Ring B is a 5-membered monocyclic heteroaryl ring having 1-4 heteroatoms independently selected from nitrogen, oxygen, and sulfur. In some embodiments, Ring B is a 5-membered monocyclic heteroaryl ring having 1-2 heteroatoms independently selected from nitrogen, oxygen, and sulfur.

In some embodiments, Ring B is a 6-membered monocyclic heteroaryl ring having 1-4 heteroatoms independently selected from nitrogen, oxygen, and sulfur. In some embodiments, Ring B is a 6-membered monocyclic heteroaryl ring having 1-2 heteroatoms independently selected from nitrogen, oxygen, and sulfur.

Exemplary optionally substituted Ring B heteroaryl groups include thienylene, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and the like.

In one embodiment, Ring C is optionally substituted phenyl. In some embodiments, Ring C is substituted phenyl comprising a 2'-substituent. In some embodiments, Ring C is substituted phenyl comprising a 6'-substituent. In some embodiments, Ring C is substituted phenyl comprising a 2'- and a 6'-substituent. In some embodiments, Ring C is 2'- and 6'-substituted phenyl. In some embodiments, Ring C is substituted phenyl comprising a 4'-substituent. In some embodiments, Ring C is substituted phenyl comprising a 2'-, a 4'- and a 6'-substituent. In some embodiments, Ring C is 2'-, 4'- and 6'-substituted phenyl. In some embodiments, Ring C is substituted phenyl comprising a 3'-substituent. In some embodiments, Ring C is substituted phenyl comprising a 5'-substituent. In some embodiments, Ring C is substituted phenyl comprising a 3'- and a 5'-substituent. In some embodiments, Ring C is 3'- and 5'-substituted phenyl. In some embodiments, each substituent is independently an optionally substituted $C_{1-6}$ alkyl. In some embodiments, a substituent is a primary substituent, e.g., methyl, ethyl, trifluoromethyl, etc. In some embodiments, each substituent is a primary substituent. In some embodiments, a substituent is a secondary substituent, e.g., isopropyl, etc. In some embodiments, each substituent is a secondary substituent. In some embodiments, a substituent is a tertiary substituent, e.g., tert-butyl, etc. In some embodiments, each substituent is a tertiary substituent. In some embodiments, each substituent is independently an unsubstituted $C_{1-6}$ alkyl. In some embodiments, each substituent is independently an unsubstituted linear $C_{1-6}$ alkyl. In some embodiments, each substituent is methyl. In some embodiments, each substituent is ethyl. In some embodiments, each substituent is independently an unsubstituted branched $C_{1-6}$ alkyl. In some embodiments, each substituent is isopropyl. In some embodiments, each substituent is tert-butyl. In some embodiments, each substituent on Ring C is the same.

In some embodiments, Ring C is 2'- and 6'-substituted phenyl, wherein each of the 2'- and 6'-substituents is independently $C_{1-6}$ alkyl. In some embodiments, Ring C is 2'- and 6'-substituted phenyl, wherein each of the 2'- and 6'-substituents is methyl. In some embodiments, Ring C is 2'- and 6'-substituted phenyl, wherein each of the 2'- and 6'-substituents is ethyl. In some embodiments, Ring C is 2'- and 6'-substituted phenyl, wherein each of the 2'- and 6'-substituents is isopropyl. In some embodiments, Ring C is 2'-, 4'- and 6'-substituted phenyl, wherein each of the 2'-, 4'- and 6'-substituents is independently $C_{1-6}$ alkyl. In some embodiments, Ring C is 2'-, 4'- and 6'-substituted phenyl, wherein each of the 2'-, 4'- and 6'-substituents is methyl. In some embodiments, Ring C is 2'-, 4'- and 6'-substituted phenyl, wherein each of the 2'-, 4'- and 6'-substituents is ethyl. In some embodiments, Ring C is 2'-, 4'- and 6'-substituted phenyl, wherein each of the 2'-, 4'- and 6'-substituents is isopropyl. In some embodiments, Ring C is 3'- and 5'-substituted phenyl, wherein each of the 3'- and 5'-substituents is independently $C_{1-6}$ alkyl. In some embodiments, Ring C is 3'- and 5'-substituted phenyl, wherein each of the 3'- and 5'-substituents is independently tertiary $C_{1-6}$ alkyl. In some embodiments, Ring C is 3'- and 5'-substituted phenyl, wherein each of the 3'- and 5'-substituents is independently tert-butyl.

In some embodiments, Ring C is 2,4,6-trimethylphenyl. In some embodiments, Ring C is 2,4,6-triethylphenyl. In some embodiments, Ring C is 2,4,6-triisopropylphenyl. In some embodiments, Ring C is 3,5-di(tert-butyl)phenyl.

In some embodiments, Ring C is an optionally substituted group selected from phenyl, an 8-10 membered bicyclic aryl ring, a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, Ring C is an optionally substituted group selected from phenyl or an 8-10 membered bicyclic aryl ring. In some embodiments, Ring C is optionally substituted phenyl. In some embodiments, Ring C is optionally substituted 8-10 membered bicyclic aryl. In some embodiments, Ring C is optionally substituted naphthyl. In some embodiments, Ring C is optionally substituted 1-naphthyl. In some embodiments, Ring C is 1-naphthyl. In some embodiments, Ring C is optionally substituted 2-naphthyl. In some embodiments, Ring C is 2-naphthyl.

In some embodiments, Ring C is an optionally substituted 3-7 membered saturated or partially unsaturated carbocyclic ring. In some embodiments, Ring C is an optionally substituted 8-10 membered bicyclic saturated, partially unsaturated or aryl ring. In some embodiments, Ring C is an optionally substituted 5-6 membered monocyclic heteroaryl ring having 1-4 heteroatoms independently selected from nitrogen, oxygen, and sulfur. In some embodiments, Ring C is an optionally substituted 4-7 membered saturated or partially unsaturated heterocyclic ring having 1-3 heteroatoms independently selected from nitrogen, oxygen, and sulfur. In some embodiments, Ring C is an optionally substituted 7-10 membered bicyclic saturated or partially unsaturated heterocyclic ring having 1-5 heteroatoms independently selected from nitrogen, oxygen, and sulfur. In some embodiments, Ring C is an optionally substituted 8-10 membered bicyclic heteroaryl ring having 1-5 heteroatoms independently selected from nitrogen, oxygen, and sulfur.

In some embodiments,

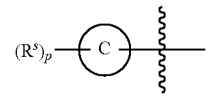

is 2,4,6-trimethylphenyl or 2,4,6-triethylphenyl or 2,4,6-triisopropylphenyl or 3,5-di(tert-butyl)phenyl or phenyl or naphthyl or 1-naphthyl or 2-naphthyl or 4-(tert-butyl)phenyl or 3,5-dimethylphenyl or 3,5-diphenylphenyl.

In some embodiments, Ring D is optionally substituted phenyl. In some embodiments, Ring D is substituted phenyl comprising a 2'-substituent. In some embodiments, Ring D is substituted phenyl comprising a 6'-substituent. In some embodiments, Ring D is substituted phenyl comprising a 2'- and a 6'-substituent. In some embodiments, Ring D is 2'- and 6'-substituted phenyl. In some embodiments, Ring D is substituted phenyl comprising a 4'-substituent. In some embodiments, Ring D is substituted phenyl comprising a 2'-, a 4'- and a 6'-substituent. In some embodiments, Ring D is 2'-, 4'- and 6'-substituted phenyl. In some embodiments, Ring D is substituted phenyl comprising a 3'-substituent. In some embodiments, Ring D is substituted phenyl comprising a 5'-substituent. In some embodiments, Ring D is substituted phenyl comprising a 3'- and a 5'-substituent. In some embodiments, Ring D is 3'- and 5'-substituted phenyl. In some embodiments, each substituent is independently an optionally substituted $C_{1-6}$ alkyl. In some embodiments, a substituent is a primary substituent, e.g., methyl, ethyl, trifluoromethyl, etc. In some embodiments, each substituent is a primary substituent. In some embodiments, a substituent is a secondary substituent, e.g., isopropyl, etc. In some embodiments, each substituent is a secondary substituent. In some embodiments, a substituent is a tertiary substituent, e.g., tert-butyl, etc. In some embodiments, each substituent is a tertiary substituent. In some embodiments, each substituent is independently an unsubstituted $C_{1-6}$ alkyl. In some embodiments, each substituent is independently an unsubstituted linear $C_{1-6}$ alkyl. In some embodiments, each substituent is methyl. In some embodiments, each substituent is ethyl. In some embodiments, each substituent is independently an unsubstituted branched $C_{1-6}$ alkyl. In some embodiments, each substituent is isopropyl. In some embodiments, each substituent is tert-butyl. In some embodiments, each substituent on Ring D is the same.

In some embodiments, Ring D is 2'- and 6'-substituted phenyl, wherein each of the 2'- and 6'-substituents is independently $C_{1-6}$ alkyl. In some embodiments, Ring D is 2'- and 6'-substituted phenyl, wherein each of the 2'- and 6'-substituents is methyl. In some embodiments, Ring D is 2'- and 6'-substituted phenyl, wherein each of the 2'- and 6'-substituents is ethyl. In some embodiments, Ring D is 2'- and 6'-substituted phenyl, wherein each of the 2'- and 6'-substituents is isopropyl. In some embodiments, Ring D is 2'-, 4'- and 6'-substituted phenyl, wherein each of the 2'-, 4'- and 6'-substituents is independently $C_{1-6}$ alkyl. In some embodiments, Ring D is 2'-, 4'- and 6'-substituted phenyl, wherein each of the 2'-, 4'- and 6'-substituents is methyl. In some embodiments, Ring D is 2'-, 4'- and 6'-substituted phenyl, wherein each of the 2'-, 4'- and 6'-substituents is ethyl. In some embodiments, Ring D is 2'-, 4'- and 6'-substituted phenyl, wherein each of the 2'-, 4'- and 6'-substituents is isopropyl. In some embodiments, Ring D is 3'- and 5'-substituted phenyl, wherein each of the 3'- and 5'-substituents is independently $C_{1-6}$ alkyl. In some embodiments, Ring D is 3'- and 5'-substituted phenyl, wherein each of the 3'- and 5'-substituents is independently tertiary $C_{1-6}$ alkyl. In some embodiments, Ring D is 3'- and 5'-substituted phenyl, wherein each of the 3'- and 5'-substituents is independently tert-butyl.

In some embodiments, Ring D is 2,4,6-trimethylphenyl. In some embodiments, Ring D is 2,4,6-triethylphenyl. In some embodiments, Ring D is 2,4,6-triisopropylphenyl. In some embodiments, Ring D is 3,5-di(tert-butyl)phenyl.

In some embodiments, Ring D is an optionally substituted group selected from phenyl, an 8-10 membered bicyclic aryl ring, a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, Ring D is an optionally substituted group selected from phenyl or an 8-10 membered bicyclic aryl ring. In some embodiments, Ring D is optionally substituted phenyl. In some embodiments, Ring D is optionally substituted 8-10 membered bicyclic aryl. In some embodiments, Ring D is optionally substituted naphthyl. In some embodiments, Ring D is optionally substituted 1-naphthyl. In some embodiments, Ring D is 1-naphthyl. In some embodiments, Ring D is optionally substituted 2-naphthyl. In some embodiments, Ring D is 2-naphthyl.

In some embodiments, Ring D is an optionally substituted 3-7 membered saturated or partially unsaturated carbocyclic ring. In some embodiments, Ring D is an optionally substituted 8-10 membered bicyclic saturated, partially unsaturated or aryl ring. In some embodiments, Ring D is an optionally substituted 5-6 membered monocyclic heteroaryl ring having 1-4 heteroatoms independently selected from nitrogen, oxygen, and sulfur. In some embodiments, Ring D is an optionally substituted 4-7 membered saturated or partially unsaturated heterocyclic ring having 1-3 heteroatoms independently selected from nitrogen, oxygen, and sulfur. In some embodiments, Ring D is an optionally substituted 7-10 membered bicyclic saturated or partially unsaturated heterocyclic ring having 1-5 heteroatoms independently selected from nitrogen, oxygen, and sulfur. In some embodiments, Ring D is an optionally substituted 8-10 membered bicyclic heteroaryl ring having 1-5 heteroatoms independently selected from nitrogen, oxygen, and sulfur.

In some embodiments,

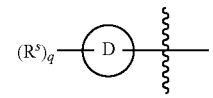

is 2,4,6-trimethylphenyl or 2,4,6-triethylphenyl or 2,4,6-triisopropylphenyl or 3,5-di(tert-butyl)phenyl or phenyl or naphthyl or 1-naphthyl or 2-naphthyl or 4-(tert-butyl)phenyl or 3,5-dimethylphenyl or 3,5-diphenylphenyl.

In some embodiments, each $R^s$ is identical. In some embodiments, Ring C and Ring D are identical. In some embodiments,

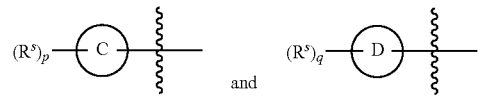

are identical.

In some embodiments, Ar is of the formula:

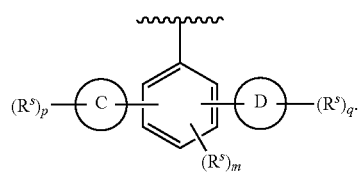

In some embodiments, Ar is of the formula:

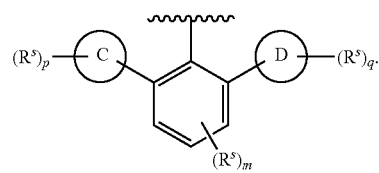

In some embodiments, Ar is of the formula:

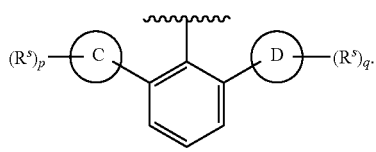

In some embodiments, Ar is of the formula:

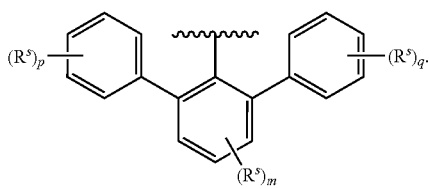

In some embodiments, Ar is of the formula:

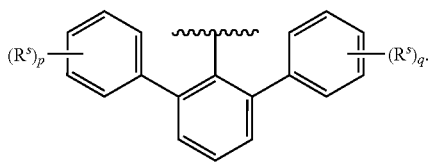

In some embodiments, Ar is of the formula:

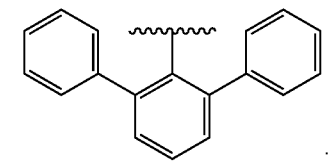 [SMILES: *c1c(-c2ccccc2)cccc1-c1ccccc1]

In some embodiments, Ar is of the formula:

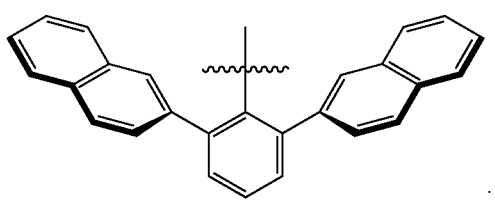

In some embodiments, Ar is of the formula

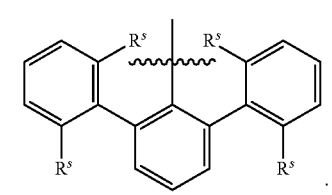

In some embodiments, Ar is of the formula

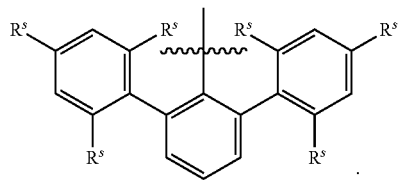

In some embodiments, Ar is of the formula

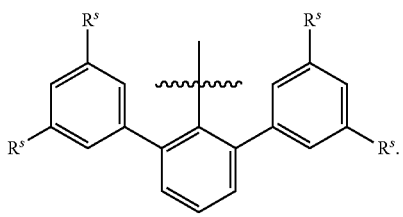

In certain embodiments wherein Ar is as depicted above, each $R^s$ is independently optionally substituted $C_{1-20}$ aliphatic. In certain embodiments wherein Ar is as depicted above, each $R^s$ is independently optionally substituted $C_{1-10}$ aliphatic. In certain embodiments wherein Ar is as depicted above, each $R^s$ is independently optionally substituted $C_{1-6}$ alkyl. In certain embodiments wherein Ar is as depicted above, each $R^s$ is independently optionally substituted primary or secondary $C_{1-6}$ alkyl. In certain embodiments wherein Ar is as depicted above, each $R^s$ is independently optionally substituted primary $C_{1-6}$ alkyl. In certain embodiments wherein Ar is as depicted above, each $R^s$ is independently optionally substituted secondary $C_{1-6}$ alkyl. In certain embodiments wherein Ar is as depicted above, each $R^s$ is independently unsubstituted primary or secondary $C_{1-6}$ alkyl. In certain embodiments wherein Ar is as depicted above, each $R^s$ is independently unsubstituted primary $C_{1-6}$ alkyl. In certain embodiments wherein Ar is as depicted above, each $R^s$ is independently unsubstituted secondary $C_{1-6}$ alkyl. Exemplary $R^s$ groups include methyl, ethyl, propyl, and butyl. In some embodiments, each $R^s$ is methyl. In some embodiments, each $R^s$ is ethyl. In some embodiments, each $R^s$ is isopropyl.

In certain embodiments, Ar has the following structure:

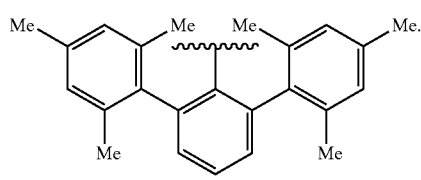

In certain embodiments, Ar has the following structure:

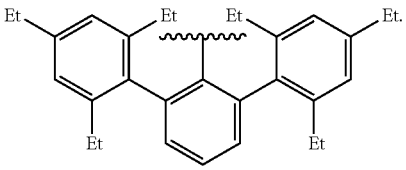 [SMILES: *c1c(-c2c(CC)cc(CC)cc2CC)cccc1-c1c(CC)cc(CC)cc1CC]

In certain embodiments, Ar has the following structure:

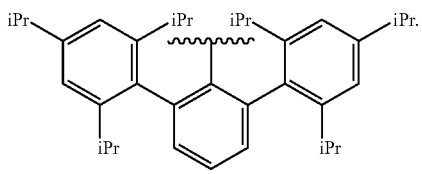 [SMILES: *c1c(-c2c(C(C)C)cc(C(C)C)cc2C(C)C)cccc1-c1c(C(C)C)cc(C(C)C)cc1C(C)C]

In certain embodiments, Ar has the following structure:

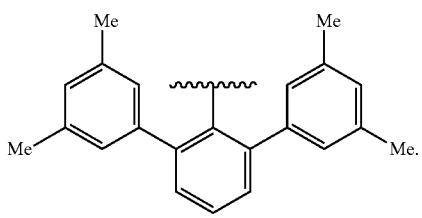 [SMILES: *c1c(-c2cc(C)cc(C)c2)cccc1-c1cc(C)cc(C)c1]

In certain embodiments, Ar has the following structure:

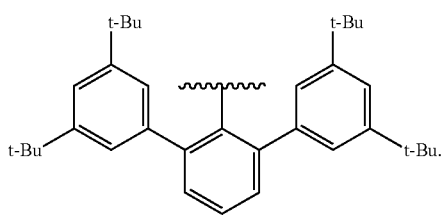 [SMILES: *c1c(-c2cc(C(C)(C)C)cc(C(C)(C)C)c2)cccc1-c1cc(C(C)(C)C)cc(C(C)(C)C)c1]

In certain embodiments, Ar has the following structure:

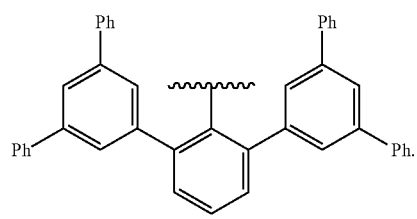 [SMILES: *c1c(-c2cc(-c3ccccc3)cc(-c3ccccc3)c2)cccc1-c1cc(-c2ccccc2)cc(-c2ccccc2)c1]

In certain embodiments, Ar has the following structure:

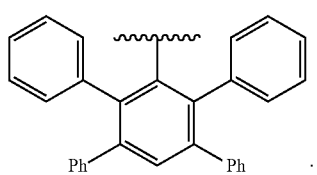 [SMILES: *c1c(-c2ccccc2)c(-c2ccccc2)cc(-c2ccccc2)c1-c1ccccc1]

In certain embodiments, Ar has the following structure:

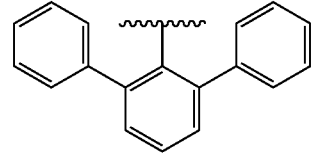

In some embodiments, $R^4$ is optionally substituted Ar, wherein Ar is

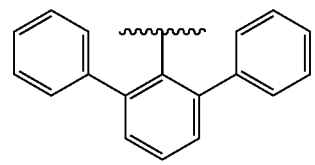

In some embodiments, $R^4$ is

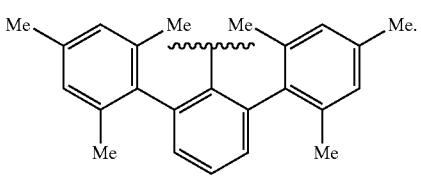 [SMILES: *c1c(-c2c(C)cc(C)cc2C)cccc1-c1c(C)cc(C)cc1C]

In some embodiments, $R^4$ is

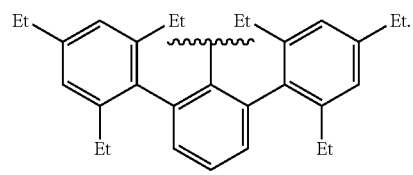 [SMILES: *c1c(-c2c(CC)cc(CC)cc2CC)cccc1-c1c(CC)cc(CC)cc1CC]

In some embodiments, $R^4$ is

In some embodiments, $R^4$ is

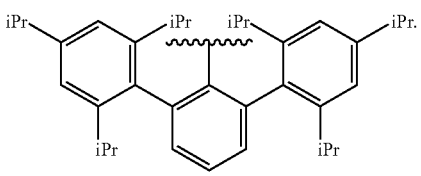 [SMILES: *c1c(-c2c(C(C)C)cc(C(C)C)cc2C(C)C)cccc1-c1c(C(C)C)cc(C(C)C)cc1C(C)C]

In some embodiments, $R^4$ is

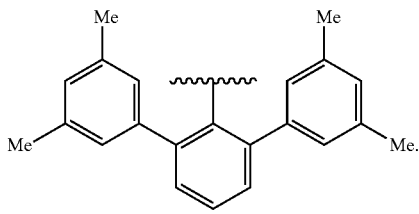 [SMILES: *c1c(-c2cc(C)cc(C)c2)cccc1-c1cc(C)cc(C)c1]

In some embodiments, $R^4$ is

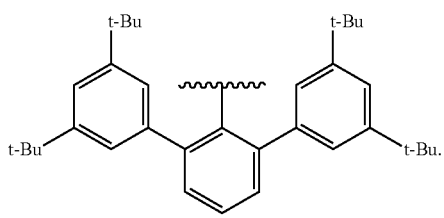 [SMILES: *c1c(-c2cc(C(C)(C)C)cc(C(C)(C)C)c2)cccc1-c1cc(C(C)(C)C)cc(C(C)(C)C)c1]

In some embodiments, $R^4$ is

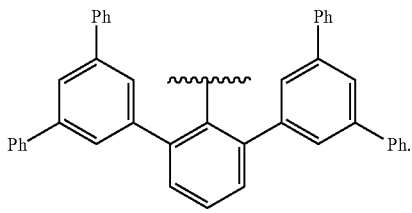 [SMILES: *c1c(-c2cc(-c3ccccc3)cc(-c3ccccc3)c2)cccc1-c1cc(-c2ccccc2)cc(-c2ccccc2)c1]

In some embodiments, $R^4$ is

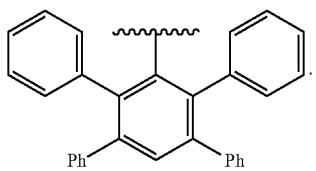 [SMILES: *c1c(-c2ccccc2)c(-c2ccccc2)cc(-c2ccccc2)c1-c1ccccc1]

In some embodiments, $R^4$ is

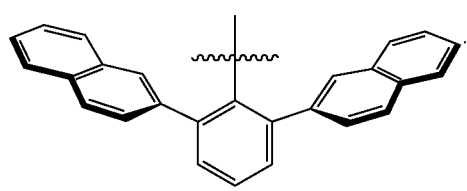

In some embodiments, $R^4$ is

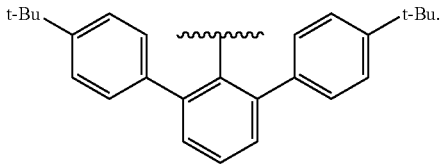 [SMILES: *c1c(-c2ccc(C(C)(C)C)cc2)cccc1-c1ccc(C(C)(C)C)cc1]

In some embodiments, $R^4$ is optionally substituted phenyl. In one embodiment, $R^4$ is optionally substituted phenyl comprising a biphenyl moiety. In one embodiment, $R^4$ is substituted phenyl comprising a 2- and a 6-substituent. In one embodiment, $R^4$ is substituted phenyl comprising a 2- and a 6-substituent, each of which is independently a cyclic group. In one embodiment, $R^4$ is substituted phenyl comprising a 2- and a 6-substituent, each of which is independently an aromatic group. In one embodiment, $R^4$ is phenyl. In another embodiment, $R^4$ is selected from 2,6-(2,6-dimethylphenyl)$_2$C$_6$H$_3$, 2,6-(mesityl)$_2$C$_6$H$_3$, 2,6-(2,6-diethylphenyl)$_2$C$_6$H$_3$, 2,6-(2,4,6-triethylphenyl)$_2$C$_6$H$_3$, 2,6-(2,6-diisopropylphenyl)$_2$C$_6$H$_3$, 2,6-(2,4,6-triisopropylphenyl)$_2$C$_6$H$_3$, 2,6-(2,6-di-t-butylphenyl)$_2$C$_6$H$_3$, 2,6-(2,4,6-tri-t-butylphenyl)$_2$C$_6$H$_3$, 2,6-(2,6-diphenylphenyl)$_2$C$_6$H$_3$, 2,6-(2,4,6-triphenylphenyl)$_2$C$_6$H$_3$, 2,6-(3,5-di-t-butylphenyl)$_2$C$_6$H$_3$, 2,6-(2,6-dichlorphenyl)$_2$C$_6$H$_3$, 2,6-(2,4,6-trichlorophenyl)$_2$C$_6$H$_3$, 2,4,6-(mesityl)$_3$C$_6$H$_2$, 2,3,5,6-(phenyl)$_4$C$_6$H, or 2,3,4,5,6-(phenyl)$_5$C$_6$.

Ar' is of the following structure:

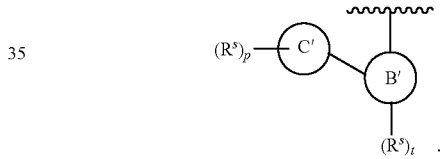

In some embodiments, p is 0-6 such as 0, 1, 2, 3, 4, 5 or 6.

In some embodiments, t is 0. In some embodiments, t is 1-4. In some embodiments, t is 1. In some embodiments, t is 2. In some embodiments, t is 3. In some embodiments, t is 4. In some embodiments, t is 0-2. In some embodiments, t is 0-3.

In some embodiments, Ring B' is optionally substituted phenyl.

In some embodiments, Ring B' is an optionally substituted 3-7 membered saturated carbocyclic ring. In some embodiments, Ring B' is an optionally substituted 5-6 membered saturated carbocyclic ring. In some embodiments, Ring B' is an optionally substituted 8-10 membered bicyclic saturated carbocyclic ring. In some embodiments, Ring B' is an optionally substituted 8-10 membered bicyclic aryl ring.

In some embodiments, Ring B' is an optionally substituted 5-6 membered monocyclic heteroaryl ring having 1-4 heteroatoms independently selected from nitrogen, oxygen, and sulfur. In some embodiments, Ring B' is an optionally substituted 5-6 membered monocyclic heteroaryl ring having 1-2 heteroatoms independently selected from nitrogen, oxygen, and sulfur.

In some embodiments, Ring B' is an optionally substituted 3-7 membered saturated heterocyclic ring having 1-3 heteroatoms independently selected from nitrogen, oxygen, and sulfur. In some embodiments, Ring B' is an optionally substituted 5-6 membered saturated heterocyclic ring having 1-2 heteroatoms independently selected from nitrogen, oxygen, and sulfur.

In some embodiments, Ring B' is an optionally substituted 7-10 membered bicyclic saturated heterocyclic ring having 1-5 heteroatoms independently selected from nitrogen, oxygen, and sulfur. In some embodiments, Ring B' is an optionally substituted 8-10 membered bicyclic saturated heterocyclic ring having 1-2 heteroatoms independently selected from nitrogen, oxygen, and sulfur.

In some embodiments, Ring B' is an optionally substituted 8-14 membered bicyclic or tricyclic heteroaryl ring having 1-5 heteroatoms independently selected from nitrogen, oxygen, and sulfur. In some embodiments, Ring B' is an optionally substituted 8-10 membered bicyclic heteroaryl ring having 1-5 heteroatoms independently selected from nitrogen, oxygen, and sulfur. In some embodiments, Ring B' is an optionally substituted 8 membered bicyclic heteroaryl ring having 1-3 heteroatoms independently selected from nitrogen, oxygen, and sulfur. In some embodiments, Ring B' is an optionally substituted 9 membered bicyclic heteroaryl ring having 1-3 heteroatoms independently selected from nitrogen, oxygen, and sulfur. In some embodiments, Ring B' is an optionally substituted 10 membered bicyclic heteroaryl ring having 1-3 heteroatoms independently selected from nitrogen, oxygen, and sulfur. In some embodiments, Ring B' is a 10-14 membered tricyclic heteroaryl ring having 1-5 heteroatoms independently selected from nitrogen, oxygen, and sulfur.

In some embodiments, Ring B' is an optionally substituted group selected from:

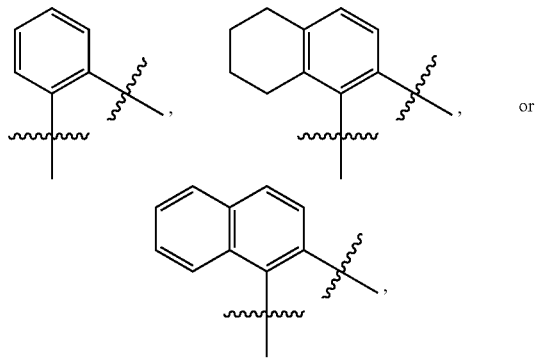

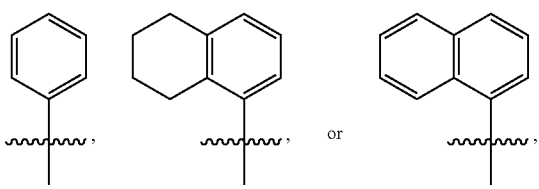

wherein each § independently represents the point of attachment to Ring C' or oxygen, and Ring B' is optionally substituted with 0-4 $R^s$.

In some embodiments, Ring C' is optionally substituted phenyl.

In some embodiments, Ring C' is an optionally substituted group selected from:

wherein each § represents the point of attachment to Ring B'; wherein Ring C' is optionally substituted with 0-6 $R^s$; and wherein each of Ring B' and $R^s$ is independently as defined above and described herein.

In some embodiments, Ring C' is optionally substituted

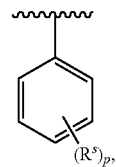

wherein $R^s$ and p is independently as defined above and described herein.

In certain embodiments, Ring C' is of the following formula:

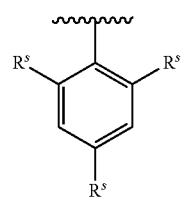

wherein each $R^s$ is independently as defined above and described herein.

In certain embodiments, Ring C' is of the following structure:

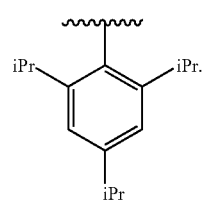 [SMILES: *c1c(C(C)C)cc(C(C)C)cc1C(C)C]

In some embodiments, Ring C' is an optionally substituted a 3-7 membered saturated carbocyclic ring. In some embodiments, Ring C' is an optionally substituted a 5-6 membered saturated carbocyclic ring. In some embodiments, Ring C' is an optionally substituted a 3-7 membered partially unsaturated carbocyclic ring. In some embodiments, Ring C' is an optionally substituted a 5-6 membered partially unsaturated carbocyclic ring.

In some embodiments, Ring C' is an optionally substituted 8-10 membered bicyclic saturated carbocyclic ring. In some embodiments, Ring C' is an optionally substituted 8-10 membered bicyclic partially unsaturated carbocyclic ring. In some embodiments, Ring C' is an optionally substituted 10 membered bicyclic aryl ring.

In some embodiments, Ring C' is an optionally substituted 5-6 membered monocyclic heteroaryl ring having 1-4 heteroatoms independently selected from nitrogen, oxygen, and sulfur. In some embodiments, Ring C' is an optionally substituted 5-6 membered monocyclic heteroaryl ring having 1-2 heteroatoms independently selected from nitrogen, oxygen, and sulfur.

In some embodiments, Ring C' is an optionally substituted 5 membered monocyclic heteroaryl ring having 1-4 heteroatoms independently selected from nitrogen, oxygen, and sulfur. In some embodiments, Ring C' is an optionally substituted 5 membered monocyclic heteroaryl ring having 1-2 heteroatoms independently selected from nitrogen, oxygen, and sulfur.

In some embodiments, Ring C' is an optionally substituted 6 membered monocyclic heteroaryl ring having 1-4 heteroatoms independently selected from nitrogen, oxygen, and sulfur. In some embodiments, Ring C' is an optionally substituted 6 membered monocyclic heteroaryl ring having 1-2 heteroatoms independently selected from nitrogen, oxygen, and sulfur.

In some embodiments, Ring C' is an optionally substituted 4-7 membered saturated heterocyclic ring having 1-3 heteroatoms independently selected from nitrogen, oxygen, and sulfur. In some embodiments, Ring C' is an optionally substituted 5-6 membered saturated heterocyclic ring having 1-2 heteroatoms independently selected from nitrogen, oxygen, and sulfur.

In some embodiments, Ring C' is an optionally substituted 7-10 membered bicyclic saturated heterocyclic ring having 1-5 heteroatoms independently selected from nitrogen, oxygen, and sulfur. In some embodiments, Ring C' is an optionally substituted 8-10 membered bicyclic saturated heterocyclic ring having 1-2 heteroatoms independently selected from nitrogen, oxygen, and sulfur.

In some embodiments, Ring C' is an optionally substituted 8-10 membered bicyclic heteroaryl ring having 1-5 heteroatoms independently selected from nitrogen, oxygen, and sulfur. In some embodiments, Ring C' is an optionally substituted 8 membered bicyclic heteroaryl ring having 1-3 heteroatoms independently selected from nitrogen, oxygen, and sulfur. In some embodiments, Ring C' is an optionally substituted 9 membered bicyclic heteroaryl ring having 1-3 heteroatoms independently selected from nitrogen, oxygen, and sulfur. In some embodiments, Ring C' is an optionally substituted 10 membered bicyclic heteroaryl ring having 1-3 heteroatoms independently selected from nitrogen, oxygen, and sulfur.

In some embodiments, each $R^s$ is independently halogen, R', —OR', —SR', —OSi(R')$_3$, —N(R')$_2$, —NR'C(O)R', or —NR'OR', wherein each R' is independently as defined above.

In some embodiments, $R^s$ is hydrogen. In some embodiments, $R^s$ is halogen. In some embodiments, $R^s$ is —F. In some embodiments, $R^s$ is —Cl. In some embodiments, $R^s$ is —Br. In some embodiments, $R^s$ is —I.

In some embodiments, $R^s$ is R'. In some embodiments, $R^s$ is optionally substituted $C_{1-6}$ aliphatic. In some embodiments, $R^s$ is optionally substituted $C_{1-6}$ aliphatic, wherein $R^s$ comprises one or more halogen. In some embodiments, $R^s$ is optionally substituted $C_{1-6}$ aliphatic, wherein $R^s$ comprises one or more —F. In some embodiments, $R^s$ is $C_{1-6}$ perfluoroaliphatic. In some embodiments, $R^s$ is $C_{1-6}$ perfluoroalkyl. In some embodiments, $R^s$ is —CF$_3$. In some embodiments, $R^s$ is optionally substituted $C_{1-6}$ alkyl. In some embodiments, $R^s$ is optionally substituted linear $C_{1-6}$ alkyl. In some embodiments, $R^s$ is optionally substituted branched $C_{1-6}$ alkyl. In some embodiments, $R^s$ is methyl. In some embodiments, $R^s$ is ethyl. In some embodiments, $R^s$ is propyl. In some embodiments, $R^3$ is isopropyl. In some embodiments, $R^s$ is butyl.

In some embodiments, $R^s$ is $C_{1-20}$ heteroaliphatic having 1-3 heteroatoms. In some embodiments, $R^s$ is optionally substituted phenyl. In some embodiments, $R^s$ is phenyl. In some embodiments, $R^s$ is optionally substituted 8-10 membered bicyclic aryl. In some embodiments, $R^s$ is optionally substituted naphthyl. In some embodiments, $R^s$ is optionally substituted 1-naphthyl. In some embodiments, $R^s$ is optionally substituted 2-naphthyl. In some embodiments, $R^s$ is 1-substituted naphthyl. In some embodiments, $R^s$ is 2-substituted naphthyl. In some embodiments, $R^s$ is optionally substituted 5-6 membered monocyclic heteroaryl ring having 1-4 heteroatoms independently selected from nitrogen, oxygen, and sulfur. In some embodiments, $R^s$ is optionally substituted 8-10 membered bicyclic heteroaryl. In some embodiments, $R^s$ is an optionally substituted 4-7 membered saturated or partially unsaturated heterocyclic ring having 1-3 heteroatoms independently selected from nitrogen, oxygen, and sulfur. In some embodiments, $R^s$ is an optionally substituted 7-10 membered bicyclic saturated or partially unsaturated heterocyclic ring having 1-5 heteroatoms independently selected from nitrogen, oxygen, and sulfur.

In some embodiments, $R^s$ is —OSi(R')$_3$. In some embodiments, $R^s$ is —OSi(R')$_3$, wherein R' is not hydrogen. In some embodiments, $R^s$ is —OSi(R')$_3$, wherein each R' is independently optionally substituted alkyl or phenyl.

In some embodiments, $R^s$ is selected from —SR', wherein R' is independently as defined above and described herein.

In certain embodiments, at least one $R^s$ is independently selected from R', —OR', —SR', —OSi(R')$_3$, or —N(R)$_2$, —NR'C(O)R', or —NR'OR', wherein each R' is independently as defined above and described herein.

In certain embodiments, at least one $R^s$ is R', wherein R' is as defined above and described herein. In some embodiments, at least one $R^s$ is optionally substituted $C_{1-6}$ aliphatic. In some embodiments, at least one $R^s$ is optionally substituted $C_{1-6}$ alkyl. In some embodiments, at least one $R^s$ is optionally substituted $C_{1-6}$ haloalkyl. In some embodiments, at least one $R^s$ is optionally substituted $C_{1-6}$ haloalkyl, wherein one substituent is —F. In some embodiments, at least one $R^s$ is optionally substituted $C_{1-6}$ haloalkyl, wherein two or more substituents are —F. In certain embodiments, at least one $R^s$ is selected from methyl, ethyl, propyl, or butyl. In certain embodiments, at least one $R^s$ is isopropyl. In certain embodiments, at least one $R^s$ is —CF$_3$.

In some embodiments, at least one $R^s$ is hydrogen or an optionally substituted group selected from $C_{1-6}$ aliphatic, phenyl, a 3-7 membered saturated carbocyclic ring, an 8-10 membered bicyclic saturated aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In certain embodiments, at least one $R^s$ is independently halogen. In certain embodiments, at least one $R^s$ is independently —F. In certain embodiments, at least one $R^s$ is independently —Cl. In certain embodiments, at least one $R^s$ is independently —Br. In certain embodiments, at least one $R^s$ is independently —I.

In some embodiments, Ar has at least $R^s$, wherein $R^s$ is halogen. In some embodiments, Ar has at least $R^s$, wherein $R^s$ is —F. In some embodiments, Ar has at least $R^s$, wherein $R^s$ is —Cl. In some embodiments, Ar has at least $R^s$, wherein $R^s$ is —Br. In some embodiments, Ar has at least $R^s$, wherein $R^s$ is —I.

In some embodiments, Ar' has at least $R^s$, wherein $R^s$ is halogen. In some embodiments, Ar' has at least $R^s$, wherein $R^s$ is —F. In some embodiments, Ar' has at least $R^s$, wherein $R^s$ is —Cl. In some embodiments, Ar' has at least $R^s$, wherein $R^s$ is —Br. In some embodiments, Ar' has at least $R^s$, wherein $R^s$ is —I.

In some embodiments, at least one $R^s$ is —OSi(R')$_3$, wherein each R' is independently as defined above and described herein.

In some embodiments, at least one $R^s$ is —OR', wherein each R' is independently as defined above and described herein.

In some embodiments, at least one $R^s$ is selected from —SR', wherein R' is independently as defined above and described herein.

In some embodiments, —OR$^4$ is an optionally substituted group selected from:

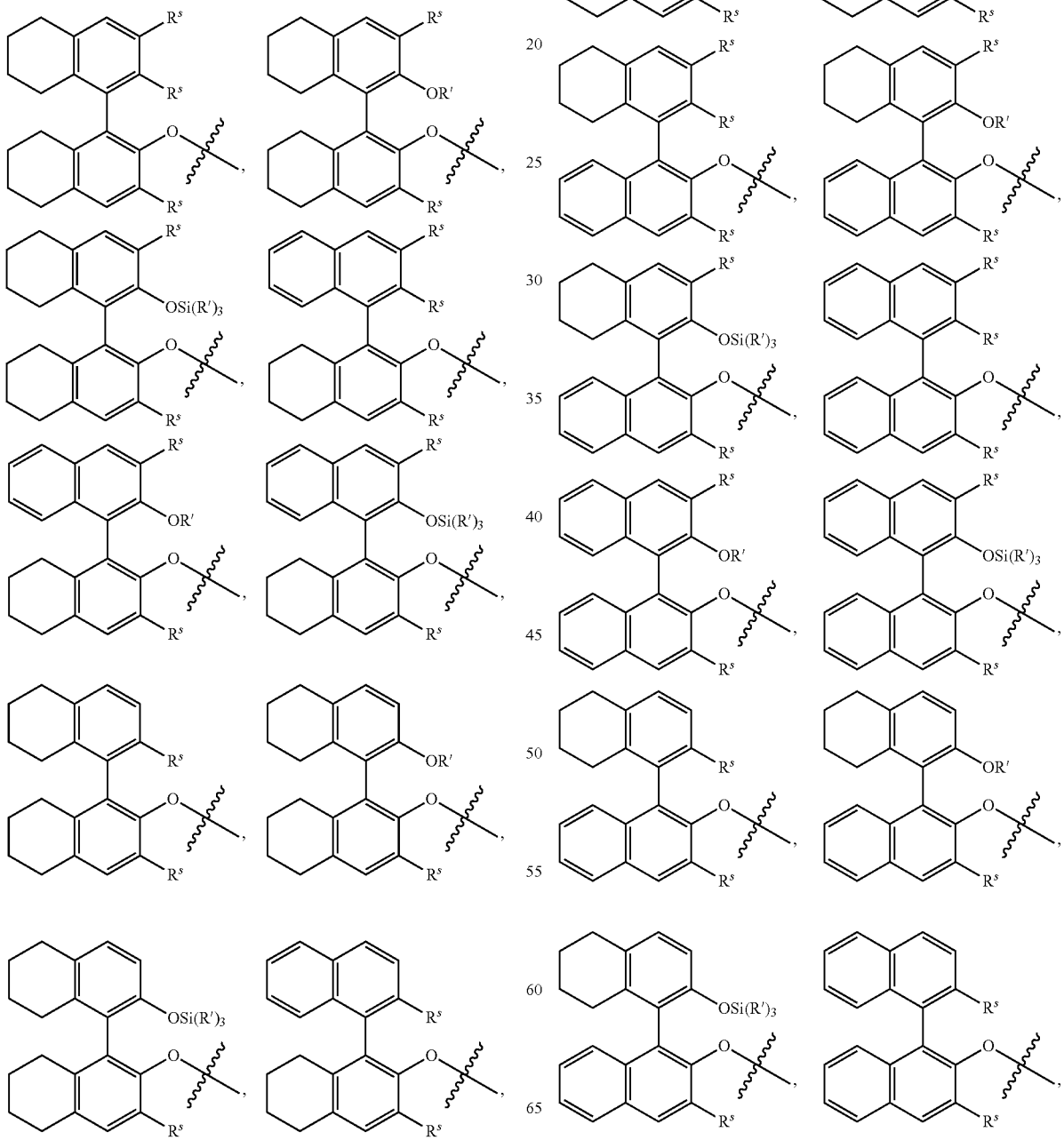

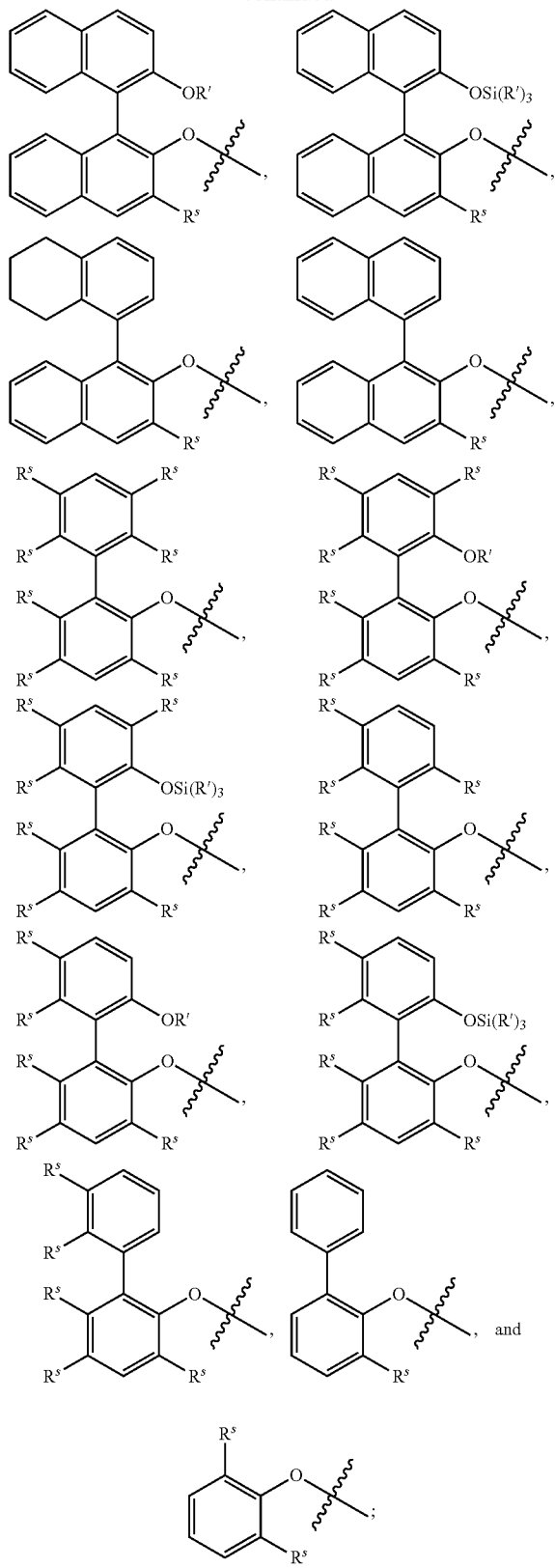

wherein each ⌇ represents the point of attachment to the metal, M, and each of $R^s$ and R' is independently as defined above and described herein.

In some embodiments, $R^s$ at the o-position of the oxygen bonded to M is —Cl, —Br, —I, or R', wherein R' is not hydrogen. In some embodiments, $R^s$ at the o-position of the oxygen bonded to M

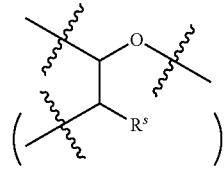

is —Cl, —Br, —I. In some embodiments, $R^s$ at the o-position of the oxygen bonded to M is —Cl. In some embodiments, $R^s$ at the o-position of the oxygen bonded to M is —Br. In some embodiments, $R^s$ at the o-position of the oxygen bonded to M is —I. In some embodiments, each $R^s$ at the o-position of the oxygen bonded to M is independently R', wherein R' is not hydrogen. In some embodiments, each $R^s$ at the o-position of the oxygen bonded to M is independently R', wherein R' is an optionally substituted cyclic group. In some embodiments, each $R^s$ at the o-position of the oxygen bonded to M is independently R', wherein R' is an optionally substituted aromatic group. In some embodiments, each $R^s$ at the o-position of the oxygen bonded to M is independently R', wherein R' is an optionally substituted tertiary group. In some embodiments, each $R^s$ at the o-position of the oxygen bonded to M is independently an optionally substituted group selected from phenyl, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, each $R^s$ at the o-position of the oxygen bonded to M is independently an optionally substituted group selected from phenyl, an 8-10 membered bicyclic aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, each $R^s$ at the o-position of the oxygen bonded to M is independently an optionally substituted group selected from phenyl, an 8-10 membered bicyclic aryl ring, a 5-6 membered monocyclic heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur. In some embodiments, each $R^s$ at the o-position of the oxygen bonded to M is independently optionally substituted phenyl. In some embodiments, each $R^s$ at the o-position of the oxygen bonded to M is independently optionally substituted 8-10 membered bicyclic aryl ring. In some embodiments, each $R^s$ at the o-position of the oxygen bonded to M is independently optionally substituted 1-naphthyl. In some embodiments, each $R^s$ at the o-position of the oxygen bonded to M is independently optionally substituted 2-naphthyl. In some embodiments, each $R^s$ at the o-position of the oxygen bonded to M is independently 1-substituted naphthyl. In some embodiments, each $R^s$ at the o-position of the oxygen bonded to M is independently 2-substituted naphthyl. In some embodiments, each $R^s$ at the o-position of the oxygen bonded to M is independently optionally substituted 5-6 membered monocyclic heteroaryl. In some embodiments, each $R^s$ at the o-position of the oxygen bonded to M is independently optionally substituted 4-7 membered saturated heterocyclyl. In some embodiments, each $R^s$ at the o-position of the oxygen bonded to M is independently optionally substituted 8-10 membered bicyclic heteroaryl. In some embodiments, each $R^s$ at the o-position of the oxygen bonded to M is independently optionally substituted 7-10 membered bicyclic saturated heterocyclyl. As understood by a person having ordinary in the art, an optionally substituted group, such as optionally substituted phenyl, can have one or two or more substituents. In some embodiments, the substituents are the same. In some other embodiments, the substituents are not all the same. In some embodiments, each substituent is different.

In some embodiments, there is $R^s$ at the 3- or 3'-position of $R^4$ when $R^4$ comprises a biaryl moiety

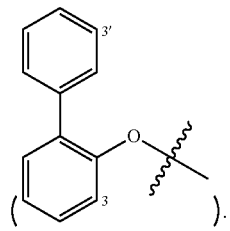

In some embodiments, there is $R^s$ at the 3-position of $R^4$ which comprises a biaryl moiety. In some embodiments, there is $R^s$ at the 3'-position of $R^4$ which comprises a biaryl moiety. In some embodiments, there are $R^s$ at the 3- and 3'-positions of $R^4$ which comprises a biaryl moiety. In some embodiments, $R^s$ is R'. In some embodiments, $R^s$ is optionally substituted $C_{1-6}$ aliphatic. In some embodiments, $R^s$ is optionally substituted $C_{1-6}$ aliphatic, wherein $R^s$ comprises one or more halogen. In some embodiments, $R^s$ is optionally substituted $C_{1-6}$ aliphatic, wherein $R^s$ comprises one or more —F. In some embodiments, $R^s$ is $C_{1-6}$ perfluoroaliphatic. In some embodiments, $R^s$ is $C_{1-6}$ perfluoroalkyl. In some embodiments, $R^s$ is —$CF_3$. In some embodiments, $R^s$ is optionally substituted $C_{1-6}$ alkyl. In some embodiments, $R^s$ is optionally substituted linear $C_{1-6}$ alkyl. In some embodiments, $R^s$ is optionally substituted branched $C_{1-6}$ alkyl. In some embodiments, $R^s$ is optionally substituted phenyl. In some embodiments, $R^s$ is optionally substituted 8-10 membered bicyclic aryl. In some embodiments, $R^s$ is optionally substituted 1-naphthyl. In some embodiments, $R^s$ is optionally substituted 2-naphthyl. In some embodiments, $R^s$ is 1-substituted naphthyl. In some embodiments, $R^s$ is 2-substituted naphthyl. In some embodiments, $R^s$ is optionally substituted 5-6 membered monocyclic heteroaryl ring having 1-4 heteroatoms independently selected from nitrogen, oxygen, and sulfur. In some embodiments, $R^s$ is optionally substituted 8-10 membered bicyclic heteroaryl. In some embodiments, $R^s$ is an optionally substituted 4-7 membered saturated or partially unsaturated heterocyclic ring having 1-3 heteroatoms independently selected from nitrogen, oxygen, and sulfur. In some embodiments, $R^s$ is an optionally substituted 7-10 membered bicyclic saturated or partially unsaturated heterocyclic ring having 1-5 heteroatoms independently selected from nitrogen, oxygen, and sulfur. In some embodiments, $R^s$ is selected from —SR', —S(O)R', —S(O)$_2$R', wherein each R' is independently as defined above and described herein.

In some embodiments, —$OR^4$ is an asymmetric ligand. In some embodiments, —$OR^4$ is a symmetric ligand. In certain embodiments, —$OR^4$ is a silyl-protected BINOL derivative.

In some embodiments, $R^4$ is Ar', and Ar' is an optionally substituted group selected from:

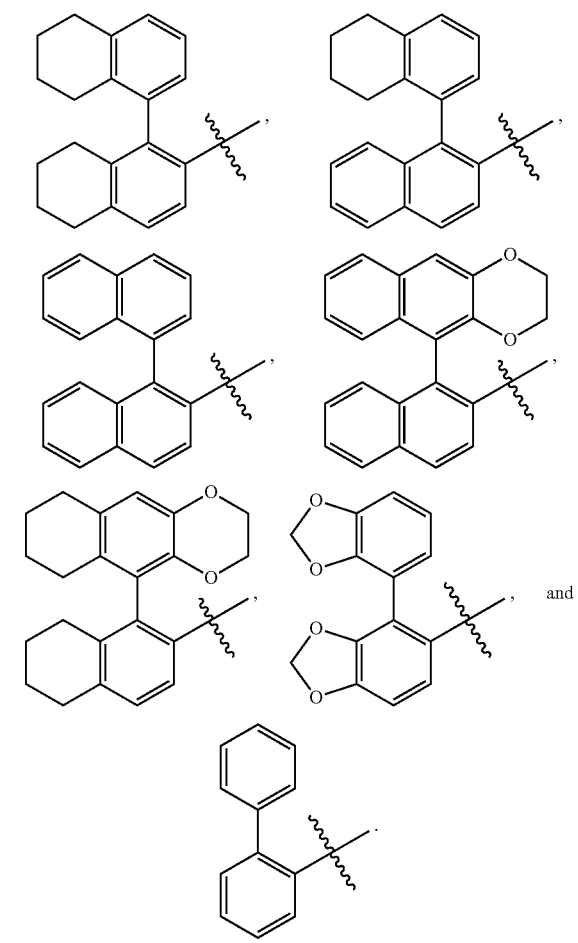

In some embodiments, $R^4$ is Ar', and Ar' is an optionally substituted group selected from:

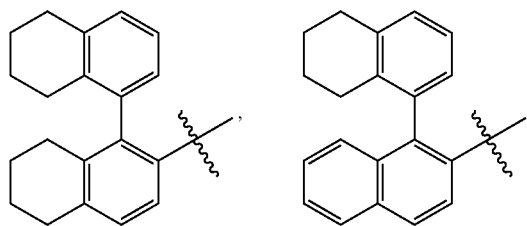

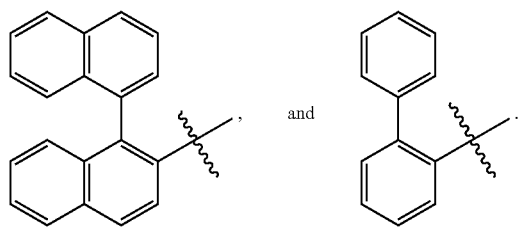
In one embodiment, —OR⁴ is
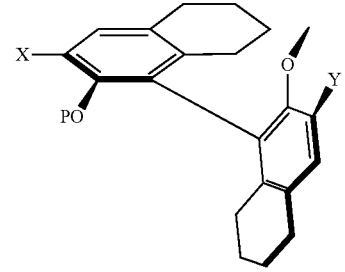
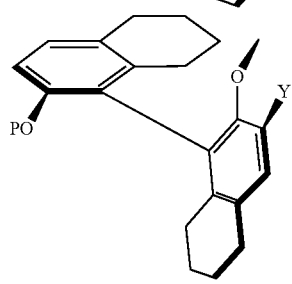
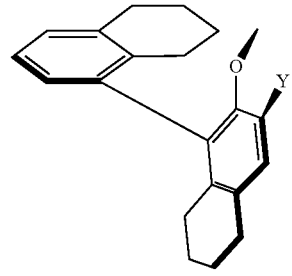
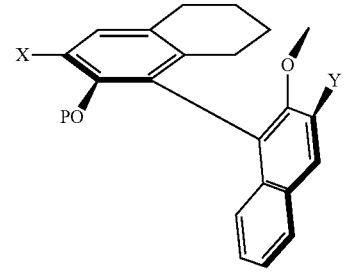
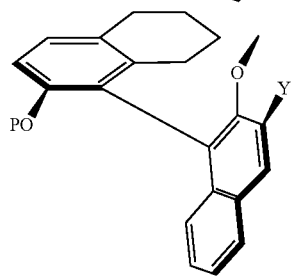
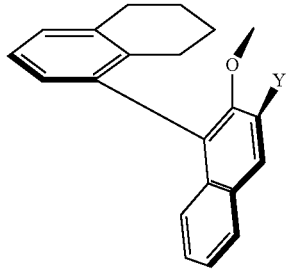
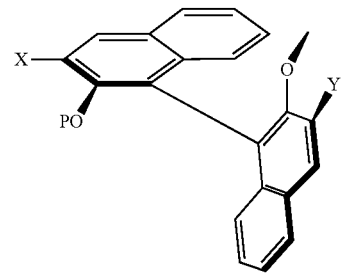
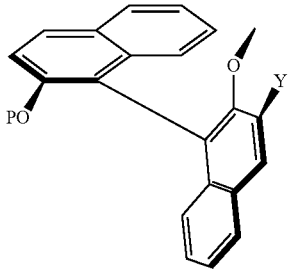
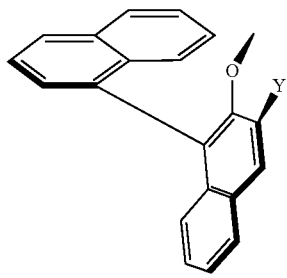
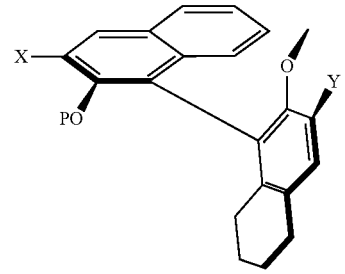
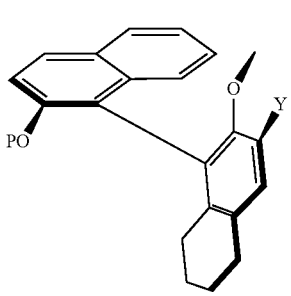

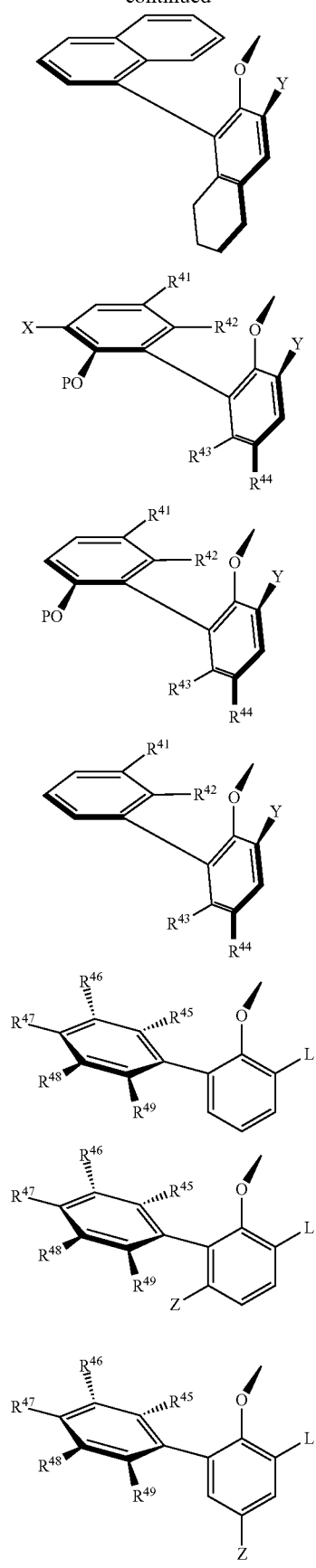

wherein:
X may be the same or different from Y;
each of X and Y is independently —H, —F, —Cl, —Br, —I, —CF₃, or any linear or branched F-containing hydrocarbon, methyl, or any linear or branched alkyl, phenyl, any mono-, di-, tri-, or tetra-substituted aryl, optionally with one or more substituents being the same as for X/Y, 1- or 2-substituted naphthyl or any O-, N-, or S-containing heterocycle, or X and/or Y may be S-based (sulfide, sulfoxide or sulfone, e.g., —SR', —S(O)R', —S(O)₂R');
each of R⁴¹, R⁴², R⁴³, R⁴⁴, R⁴⁵, R⁴⁶, R⁴⁷, R⁴⁸ and R⁴⁹ is independently —H, —F, —Cl, —Br, —I, —CF₃, or any linear or branched hydrocarbon, methyl, or any linear or branched alkyl, phenyl, any mono-, di-, tri-, or tetra-substituted aryl, optionally with substituents, 1- or 2-substituted naphthyl or any O-, N-, or S-containing heterocycle; or R⁴¹, R⁴², R⁴³, R⁴⁴, R⁴⁵, R⁴⁶, R⁴⁷, R⁴⁸ and R⁴⁹ may be S-based based (sulfide, sulfoxide or sulfone, e.g., —SR', —S(O)R', —S(O)₂R');
R⁴¹, R⁴², R⁴³, and R⁴⁴, may be identical or different in any possible combination, and may be X or Y;
R⁴⁵, R⁴⁶, R⁴⁷, R⁴⁸ and R⁴⁹ may be identical or different in any possible combination, and may be X or Y;

L may be phenyl, any mono-, di-, tri-, or tetra-substituted aryl, optionally with substituents, 1- or 2-substituted naphthyl or any O-, N-, or S-containing heterocycle;

Z, Q and G may be identical, or three different substituents, or any 2 (e.g., Z=Q or Q=G) may be identical;

Z, Q and G may be —H, —F, —Cl, —Br, —I, —CF$_3$, or any linear or branched hydrocarbon, Me, or any linear or branched alkyl, Ph, any mono-, di-, tri-, or tetra-substituted aryl (all isomers) optionally with substituents, 1- or 2-substituted naphthyl or any O-, N-, or S-containing heterocycle; or Z, Q and G may be S-based based (sulfide, sulfoxide or sulfone, e.g., —SR', —S(O)R', —S(O)$_2$R'); and P is a protecting group.

In an embodiment, P is a Si protecting group as defined in the Definition section, i.e. a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl).

In one embodiment, X, Y, $R^{41}$, $R^{42}$, $R^{43}$, $R^{44}$, $R^{45}$, $R^{46}$, $R^{47}$, $R^{48}$ and $R^{49}$, Z, Q and G are independently from one another —H, —F, —Cl, —Br, —I, —CF$_3$, or linear or branched F-containing $C_{1-20}$ alkyl, or linear or branched $C_{1-20}$ alkyl, phenyl, optionally substituted with R'; and P is a protecting group.

In one embodiment, $R^4$ is aryl, wherein aryl is selected from naphthyl, tetrahydronaphthyl, binaphthyl, or bi(tetrahydronaphthyl) such as 1,1'-bi(tetrahydronaphthyl), optionally independently substituted with one or more of halogen, or R', —OR', —SR', —OSi(R')$_3$, —N(R')$_2$, —NR'C(O)R', or —NR'OR'. In one embodiment, such binaphthyl or bi(tetrahydronaphthyl) is substituted or is additionally substituted with at least one hydroxy group. In one embodiment, said hydroxyl group or additional hydroxyl group is in 2'-position. In one embodiment, $R^4$ may then act as a bidentate ligand. In one embodiment, $R^4$—O is derived from a BINOL (1,1'-binaphthalene-2,2'-diol), which may act as a bidentate ligand. In another embodiment, $R^4$—O is derived from a 1,1'-bi(tetrahydronaphthalene)-2,2'-diol, which may act as a bidentate ligand. Such residues are known in the art as bitet ligands.

In another embodiment, $R^4$ is an optionally substituted 3-7 membered saturated carbocyclic ring. In some embodiments, $R^4$ is an optionally substituted 8-10 membered bicyclic saturated ring, or aryl ring. In some embodiments, $R^4$ is an optionally substituted 5-6 membered monocyclic heteroaryl ring having 1-4 heteroatoms independently selected from nitrogen, oxygen, and sulfur. In some embodiments, $R^4$ is an optionally substituted 4-7 membered saturated heterocyclic ring having 1-3 heteroatoms independently selected from nitrogen, oxygen, and sulfur. In some embodiments, $R^4$ is an optionally substituted 7-10 membered bicyclic saturated heterocyclic ring having 1-5 heteroatoms independently selected from nitrogen, oxygen, and sulfur. In some embodiments, $R^4$ is an optionally substituted 8-14 membered bicyclic or tricyclic heteroaryl ring having 1-5 heteroatoms independently selected from nitrogen, oxygen, and sulfur.

In a further embodiment, $R^4$ is optionally substituted $C_{1-20}$ aliphatic. In some embodiments, $R^4$ is optionally substituted $C_{1-20}$ alkyl. In some embodiments, $R^4$ is $C_{1-20}$ alkyl. In some embodiments, $R^4$ is $C_{1-20}$ haloalkyl. In some embodiments, $R^4$ is tert-butyl. In some embodiments, $R^4$ is —C(CF$_3$)$_2$Me.

In some embodiments, $R^4$ is optionally substituted $C_{1-20}$ heteroaliphatic having 1-3 heteroatoms independently selected from nitrogen, oxygen, and sulfur. In some embodiments, $R^4$ is optionally substituted $C_{1-6}$ heteroaliphatic having 1-3 heteroatoms independently selected from nitrogen, oxygen, and sulfur.

In some embodiments, $R^4$ is triarylsilyl.

$R^5$ is halogen. In some embodiments, $R^5$ is —F. In some embodiments, $R^5$ is —Cl. In some embodiments, $R^5$ is —Br. In some embodiments, $R^5$ is —I.

Each $R^6$ is independently a neutral ligand.

In one embodiment, $R^6$ is a nitrogen-containing ligand, wherein the nitrogen atom coordinates to M.

In some embodiments, $R^6$ is a nitrile. In some embodiments, $R^6$ has the structure of R'—CN. In some embodiments, $R^6$ is CH$_3$CN. In some embodiments, $R^6$ has the structure of N(=$R^{6'}$)($R^{6'}$), wherein the two $R^{6'}$ are taken together with the nitrogen atom to form an optionally 5-10 membered partially unsaturated heterocyclic or heteroaryl ring having, in addition to the nitrogen atom, 1-4 heteroatoms independently selected from nitrogen, oxygen, and sulfur. In some embodiments, $R^6$ has the structure of N(=$R^{6'}$)($R^{6'}$), wherein the two $R^{6'}$ are taken together with the nitrogen atom to form an optionally substituted 6-membered heteroaryl ring having, in addition to the nitrogen atom, 1-4 heteroatoms independently selected from nitrogen, oxygen, and sulfur. In some embodiments, $R^6$ is optionally substituted pyridine.

In some embodiments, $R^6$ is pyridine. In some embodiments, $R^6$ is substituted pyridine. In some embodiments, $R^6$ is substituted pyridine, wherein one to five of the substituents are independently $R^s$.

In some embodiments, $R^6$ is selected from:

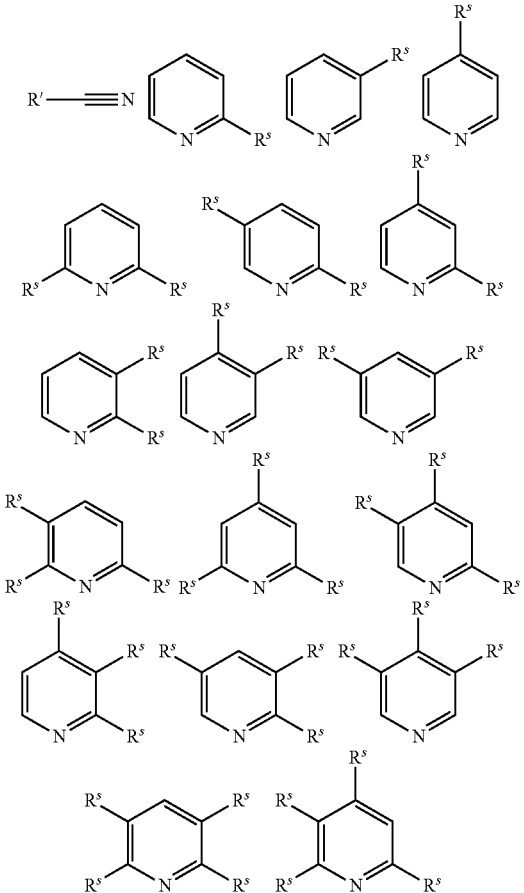

-continued

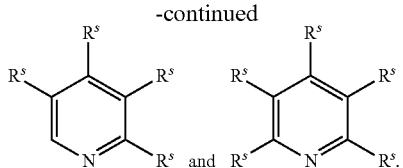

In another embodiment, $R^6$ is a 1,10-phenanthroline. Such ligand may act as a bidentate ligand. Said 1,10-phenanthroline may optionally be substituted with $C_{1-4}$ alkyl, $C_{1-4}$ alkoxy, halogen, or phenyl. The term "pyridine" encompasses a 1,10-phenanthroline.

In one embodiment, $R^6$ is a primary amine $R'$—$NH_2$, wherein R' is defined above. Preferred amines are e.g. tert.-butylamine or 1-aminoadamantane.

In one embodiment, $R^6$ is an oxygen-containing compound, wherein the oxygen atom coordinates to M. Suitable oxygen-containing compounds are linear and cyclic ethers. An example of a cyclic ether is tetrahydrofuran. An example of a linear ether is diethylene glycol dimethyl ether where both oxygen atoms coordinate to M.

In another embodiment, $R^6$ is a phosphorus-containing compound, wherein the phosphorus atom coordinates to M. In one embodiment, the phosphorus-containing compound is of formula $(R^a, R^b, R^c)P$, wherein $R^a$, $R^b$, and $R^e$ independently from one another have the meaning of R' as defined herein. An example is a phosphine such as methyldiphenylphosphine.

In some embodiments, $R^6$ is a monodentate ligand. In some embodiments, $R^6$ is bidentate ligand. In some embodiments, $R^6$ is a polydentate ligand. In some embodiments, n is 2 and the two $R^6$ are optionally taken together to form a bidentate ligand. In some embodiments, n is 2 and the two $R^6$ are taken together to form a bidentate ligand.

In some embodiments, when dissolved in a solvent, one or more of $R^6$ may dissociate.

As generally defined above, n is 0-2. In some embodiments, n is 0. In some embodiments, n is 1. In some embodiments, n is 1-2. In some embodiments, n is 2.

As defined above, R' is independently hydrogen or an optionally substituted group selected from $C_{1-20}$ aliphatic, $C_{1-20}$ heteroaliphatic having 1-3 heteroatoms independently selected from nitrogen, oxygen, and sulfur, or independently selected from nitrogen and oxygen, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur, wherein:

two R' groups on the same nitrogen atom are optionally taken together with the nitrogen atom to form an optionally substituted 3-8 membered, saturated ring, or aryl ring having 1-4 heteroatoms independently selected from nitrogen, oxygen, and sulfur.

In some embodiments, each R' is independently hydrogen or an optionally substituted group selected from $C_{1-6}$ aliphatic, $C_{1-6}$ heteroaliphatic having 1-3 heteroatoms, phenyl, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur, wherein:

two R' groups on the same nitrogen atom are optionally taken together with the nitrogen atom to form an optionally substituted 3-8 membered, saturated ring, or aryl ring having 1-4 heteroatoms independently selected from nitrogen, oxygen, and sulfur.

In some embodiments, each R' is independently optionally substituted $C_{1-20}$ aliphatic. In some embodiments, each R' is independently optionally substituted $C_{1-6}$ aliphatic. In some embodiments, each R' is independently optionally substituted $C_{1-6}$ alkyl. In some embodiments, each R' is independently optionally substituted $C_{1-6}$ haloalkyl. In some embodiments, each R' is independently optionally substituted $C_{1-6}$ haloalkyl, wherein one substituent is —F. In some embodiments, each R' is independently optionally substituted $C_{1-6}$ haloalkyl, wherein two or more substituents are —F. In certain embodiments, at least one R' is independently selected from methyl, ethyl, propyl, or butyl. In certain embodiments, at least one R' is isopropyl. In certain embodiments, at least one R' is —$CF_3$.

In some embodiments, R' is optionally substituted $C_{1-20}$ heteroaliphatic having 1-3 heteroatoms.

In some embodiments, at least one R' is hydrogen. In some embodiments, at least one R' is independently selected from an optionally substituted group selected from $C_{1-6}$ aliphatic, phenyl, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

Exemplary catalysts or metal complexes of formula I-a include those listed below:

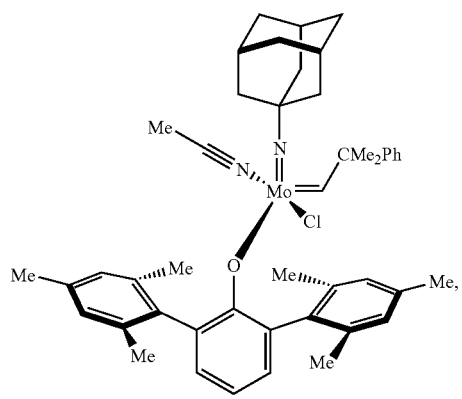

-continued

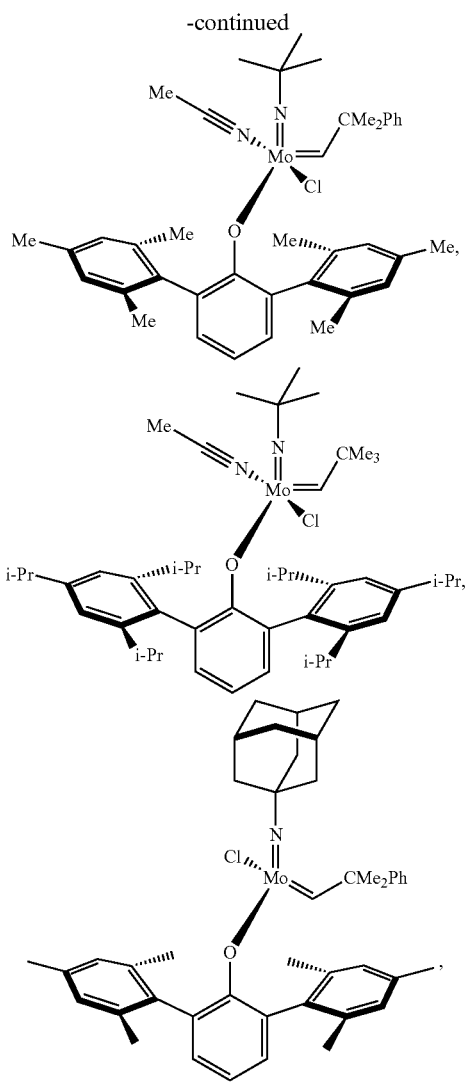

Mo(NAd)(CHCMe₂Ph)(OHMT)(Br)(py), Mo(NAd)(CHR)(OHMT)(Cl)(py), Mo(NAd)(CHR)(OHMT)(Br)(MeCN), Mo(NAd)(CHR)(OHMT)(Cl)(MeCN), Mo(NC₆F₅)(CHR)(OHMT)(Br)(py), Mo(NC₆F₅)(CHR)(OHMT)(Cl)(py), Mo(NAr)(CHCMe₂Ph)(OHIPT)(Cl)(MeCN), Mo(N-t-Bu)(CHCMe₂Ph)(OHMT)(Cl)(MeCN), Mo(N-t-Bu)(CHCMe₂Ph)(OHIPT)(Cl)(MeCN), Mo(N-t-Bu)(CHCMe₂Ph)(OTBT)(Cl)(MeCN), Mo(NAr)(CHCMe₂Ph)(OHIPT)(Cl)(MeCN), Mo(NAd)(CHR)(OHMT)(Br), Mo(NAd)(CHR)(OHMT)(Cl)(AdNH₂), Mo(N-t-Bu)(CHt-Bu)(OHMT)(Cl)(MeCN), Mo(N-t-Bu)(CHt-Bu)(OHMT)(Br)(MeCN), Mo(N-t-Bu)(CHt-Bu)(OHIPT)(Cl)(MeCN), Mo(NC₆F₅)(CHR)(OHMT)(Cl)(PhMe₂P), Mo(NC₆F₅)(CHR)(OHIPT)(Cl)(PhMe₂P), and Mo(NC₆F₅)(CHR)(OHMT)(Cl)(Me₃P),
wherein Ad is adamant-1-yl, AdNH₂ is 1-amino-adamantane, py is pyridine, Ph is phenyl, Me is methyl, R is —CMe₂Ph, OHMT is O-2,6-(mesityl)₂C₆H₃, OHIPT is O-2,6-(2,4,6-(i-Pr)₃C₆H₂)₂C₆H₃, and OTBT is O-2,6-(3,5-(di-t-Bu-phenyl)₂C₆H₃).

The compounds I-a and I-b according to the disclosure may be prepared according to methods which are known to the person skilled in the art, respectively according to methods as specified in the THIRD ASPECT below.

The following compounds of formula I-a are known from L. C. H. Gerber et al., J. Amer. Chem. Soc. 2011, 135, 18142-18144: Mo(NAr*)(CHCMe₂Ph)Cl(OAr*)(py); Mo(NAr*)(CHCMe₂Ph)Cl(O-t-Bu)(py); Mo(NAr*)(CHCMe₂Ph)Cl[OCMe(CF₃)₂](py); Mo(NAr*)(CHCMe₂Ph)Cl(OAr)(py) (termed as compounds 8, 9, 10 and 11 therein). The following compounds of formula I-b are known from Dmitry V. Peryshkov et al., J. Amer. Chem. Soc. 2011, 133, 20754-20757: W(O)(CH-t-Bu)Cl(OHIPT)(PMe₂Ph); W(O)(CH-t-Bu)Cl(OHMT)(PMe₂Ph) (termed as compounds 2 and 4 therein); William P. Forrest et al., Organometallics 2014, 33, 2313-2325: W(O)(CHCMe₂Ph)Cl(OHMT)(PMe₂Ph); W(O)(CHCMe₂Ph)Cl(ODFT)(PMe₂Ph); W(O)(CHCMe₂Ph)Cl(OTPP)(PMe₂Ph); W(O)(CHCMe₂Ph)Cl(OdAdP)(PMe₂Ph); W(O)(CHCMe₂Ph)Cl(ODBMP)(PMe₂Ph) (termed as compounds 2a, 2b, 2c, 2d, 2e therein);
wherein Ar* is 2,6-dimesitylphenyl (HMT); Ar' is 2,6-dimethylphenyl; HIPT is 2,6-di(hexaisopropylphenyl)phenyl, DFT is 2,6-di(pentafluorophenyl)phenyl; TPP is 2,3,5,6-tetraphenylphenyl; dAdP is 2,6-diadamantylphenyl; DBMP is 4-methyl-2,6-di(diphenylmethyl)phenyl; Me is methyl; Ph is phenyl; Bu is butyl; and py is pyridine.

The following compound of formula I-c is known from Hyangsoon Jeong et al., Organometallics 2015, 34, 4408-4418: W(N-t-Bu)(CH-t-Bu)Cl(OHMT)(py) (termed as compound 6_w therein), wherein HMT is 2,6-dimesitylphenyl.

In some embodiments, the present disclosure provides a composition comprising a compound of formula I-a or I-b or I-c. In some embodiments, greater than about 10%, 20%, 30%, 40%, 50%, 60%, 70%, 80%, 90%, 95%, 96%, 97%, 98%, or 99% by mole (mol %) of all compounds comprising M in a provided composition is a compound of formula I-a or I-b or I-c.

As mentioned above, compounds and compositions according to the disclosure are useful in a method of performing metathesis reactions. Exemplary such methods and reactions are described below.

According to a SECOND ASPECT, a compound of formula I-a or I-b or I-c or a composition comprising a compound of formula I-a or I-b or I-c as defined in the FIRST ASPECT promotes a metathesis reaction.

Various types of metathesis reactions are known in the art, including but not limited to those described in present disclosure.

In some embodiments, an olefin metathesis provides at least one product comprising a double bond, wherein the double bond is substituted with halogen. In some embodiments, an olefin metathesis provides at least one product comprising a double bond, wherein the double bond is substituted with optionally substituted $C_{1-6}$ haloalkyl. In some embodiments, an olefin metathesis provides at least one product comprising a double bond, wherein the double bond is substituted with halomethyl.

In some embodiments, an olefin metathesis provides at least one product comprising a double bond, wherein the double bond is substituted with F or —CF₃ or —C₂F₅ or —C₃F₇ or —C₄F₉ or —C₅F₁₁ or —C₆F₁₃. In further embodiments, an olefin metathesis provides at least one product comprising a double bond, wherein the double bond is substituted with —CHF₂. In some embodiments, an olefin metathesis provides at least one product comprising a double bond, wherein the double bond is substituted with —CH₂F.

Accordingly, the present disclosure provides a method for performing a metathesis reaction, comprising:
reacting a first species comprising a first double bond with a second species comprising a second double bond in the presence of a compound of formula I-a or I-b or I-c, or a composition comprising a compound of formula I-a or I-b or I-c, to provide at least one product comprising a third double bond, wherein:

a carbon atom of the first double bond in the first species is substituted with a first substituent selected from halogen and optionally substituted $C_{1-6}$ haloalkyl; and the third double bond in the at least one product comprises a carbon atom of the first double bond and a carbon atom of the second double bond, wherein the carbon atom of the first double bond is substituted with the first substituent;

wherein the compound of formula I-a or I-b is:

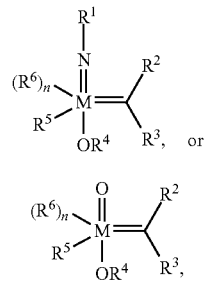

wherein:
M in compound of formula I-b is molybdenum, and M in compound of formula I-b is tungsten;

$R^1$ is a group selected from
$C_{1-20}$ aliphatic, or $C_{1-20}$ heteroaliphatic having 1-3 heteroatoms independently selected from nitrogen, oxygen, and sulfur; or
a 3-7 membered saturated carbocyclic ring, or an 8-10 membered bicyclic or tricyclic saturated ring; or
a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur;

each of $R^2$ and $R^3$ is independently hydrogen or a group selected from $C_{1-20}$ aliphatic, $C_{1-20}$ heteroaliphatic having 1-3 heteroatoms independently selected from nitrogen, oxygen, and sulfur, or aryl;

$R^4$ is a group selected from
$C_{1-20}$ aliphatic, or $C_{1-20}$ heteroaliphatic having 1-3 heteroatoms independently selected from nitrogen, oxygen, and sulfur; or
a 3-7 membered saturated or partially unsaturated carbocyclic ring, or an 8-10 membered bicyclic or tricyclic saturated or partially unsaturated ring; or
a 4-7 membered saturated heterocyclic ring having 1-3 heteroatoms independently selected from nitrogen, oxygen, and sulfur, or a 7-10 membered bicyclic saturated heterocyclic ring having 1-5 heteroatoms independently selected from nitrogen, oxygen, and sulfur; or an aryl ring, a 5-6 membered heteroaryl ring having 1-4 heteroatoms independently selected from nitrogen, oxygen, and sulfur, or an 8-10 membered bicyclic heteroaryl ring having 1-5 heteroatoms independently selected from nitrogen, oxygen, and sulfur, or an 8-14 membered bicyclic or tricyclic heteroaryl ring having 1-5 heteroatoms independently selected from nitrogen, oxygen, and sulfur;
triaryl silyl;
$R^5$ is halogen;
each $R^6$ is independently a neutral ligand; and
n is 0-2;
wherein
each of $R^1$, $R^4$ or $C_{1-20}$ aliphatic, $C_{1-20}$ heteroaliphatic or aryl as defined for $R^2$ and $R^3$ may optionally be independently substituted with one or more of halogen, or R', —OR', —SR', —OSi(R')$_3$, —N(R')$_2$, —NR'C(O)R', or —NR'OR', wherein
R' is independently hydrogen, $C_{1-20}$ aliphatic, $C_{1-20}$ heteroaliphatic having 1-3 heteroatoms, a 3-7 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, and an 8-10 membered bicyclic heteroaryl ring having 1-5 heteroatoms independently selected from nitrogen, oxygen, and sulfur, wherein:
two R' groups on the same nitrogen atom are optionally taken together with the nitrogen atom to form an optionally substituted 3-8 membered saturated ring, or aryl ring having 1-4 heteroatoms independently selected from nitrogen, oxygen, and sulfur.

Some embodiments of the catalyst of formula I-a and I-b used in the method according to the disclosure are specified in the SUMMARY section.

In a further embodiment, the method is promoted with a compound of formula I-c:

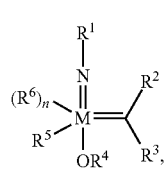

wherein:
M is tungsten;
$R^1$ is a group selected from adamantyl, t-butyl, and phenyl;
each of $R^2$ and $R^3$ is independently hydrogen or $C(CH_3)_3$ or $C(CH_3)_2C_6H_5$ or phenyl;
$R^4$ is a group selected from
an aryl ring;
$R^5$ is chlorine or bromine;
each $R^6$ is independently a neutral ligand selected from a nitrile, a pyridine and a phosphine; and
n is 0-2;
wherein
each of phenyl as defined for $R^1$, $R^2$ and $R^3$ and aryl as defined for $R^4$ may be independently substituted with one or more of halogen, or R', —OR', —SR', —OSi(R')$_3$, —N(R')$_2$, —NR'C(O)R', or —NR'OR', wherein
R' is independently hydrogen, $C_{1-20}$ aliphatic, $C_{1-20}$ heteroaliphatic having 1-3 heteroatoms independently selected from nitrogen and oxygen, a 5-6 membered saturated carbocyclic ring, an 8-10 membered bicyclic saturated ring or aryl ring, a 5-6 membered heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, and an 8-10 membered bicyclic heteroaryl ring having 1-5 heteroatoms independently selected from nitrogen, oxygen, and sulfur, wherein:

two R' groups on the same nitrogen atom are optionally taken together with the nitrogen atom to form an optionally substituted 3-8 membered, saturated ring or aryl ring having 1-4 heteroatoms independently selected from nitrogen, oxygen, and sulfur.

In some embodiments, a first substituent is halogen. In some embodiments, a first substituent is —Cl. In some embodiments, a first substituent is —Br. In some embodiments, a first substituent is —I. In some embodiments, a first substituent is —F.

In a further embodiment, a first substituent is optionally substituted $C_{1-6}$ haloalkyl. In some embodiments, a first substituent is methyl substituted with one to three halogen atoms. In some embodiments, a first substituent is optionally substituted $C_{1-6}$ haloalkyl comprising one or more —F. In some embodiments, a first substituent is methyl substituted with one to three halogen atoms, wherein at least one halogen atom is F. In some embodiments, a first substituent is —CH$_2$F. In some embodiments, a first substituent is —CHF$_2$. In some embodiments, a first substituent is —CF$_3$. In some embodiments, a first substituent is —CF(X')$_2$, wherein each X' is independently —H, —F, —Cl, —Br, or —I. In some embodiments, a first substituent is —CF(X')$_2$, wherein each X' is independently —F, —Cl, —Br, or —I. In some embodiments, a first substituent is —CClF$_2$.

In some embodiments, a first substituent is —CF$_3$ or —C$_2$F$_5$ or —C$_3$F$_7$ or —C$_4$F$_9$ or —C$_5$F$_{11}$ or —C$_6$F$_{13}$.

In some embodiments, each carbon atom of the first double bond in the first species is independently substituted with a first substituent. In some embodiments, the two first substituents are the same.

In some embodiments, a first species is substituted ethylene, wherein a carbon atom is substituted with a first substituent. In some embodiments, a first species is 1,2-disubstituted ethylene. In some embodiments, a first species is substituted ethylene, wherein each carbon atom is independently substituted with a first substituent. In some embodiments, the two substituents are the same. In some embodiments, a first species is cis-1,2-disubstituted ethylene, wherein each carbon atom is independently substituted with a first substitute group. In some embodiments, a first species has the structure of

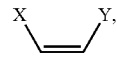

wherein each of X and Y is independently a first substituent. In some embodiments, provided technologies selectively promote metathesis involving cis or Z double bond in the presence of both cis/trans or Z/E double bonds to selectively form a Z double bond via metathesis reactions. Exemplary transformations are exemplified below.

In some embodiments, a first double bond is Z with respect to a halogen substituent on the first carbon atom of the first double bond and a halogen substituent on the second carbon atom of the first double bond. In some embodiments, a first species has the structure of

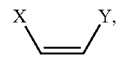

wherein each of X and Y is independently halogen. In some embodiments, each of X and Y is —F. In some embodiments, each of X and Y is —Cl. In some embodiments, each of X and Y is —Br. In some embodiments, one of X and Y is —F and the other is —Cl. In some embodiments, one of X and Y is —F and the other is —Br. In some embodiments, X and Y is different. In some embodiments, X and Y are the same.

In some embodiments, a first species has the structure of

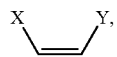

wherein each of X and Y is independently optionally substituted $C_{1-6}$ haloalkyl. In some embodiments, each of X and Y is independently —CF(X')$_2$, wherein each X' is independently —H, —F, —Cl, —Br, or —I. In some embodiments, each of X and Y is independently —CF(X')$_2$, wherein each X' is independently —F, —Cl, —Br, or —I. In some embodiments, X and Y are the same. In some embodiments, each of X and Y is —CF$_3$ or —C$_2$F$_5$ or —C$_3$F$_7$ or —C$_4$F$_9$ or —C$_5$F$_{11}$ or —C$_6$F$_{13}$.

In some embodiments, a second double bond has one or more substituents. In some embodiments, each substituent is independent R$^t$, wherein R$^t$ is an optionally substituted group selected from $C_{1-20}$ aliphatic, $C_{1-20}$ heteroaliphatic having 1-5 heteroatoms independently selected from boron, silicon, phosphorus, nitrogen, oxygen, and sulfur, phenyl, a 3-7 membered saturated carbocyclic ring, an 8-10 membered bicyclic saturated ring, or aryl ring, a 5-6 membered monocyclic heteroaryl ring having 1-4 heteroatoms independently selected from boron, silicon, phosphorus, nitrogen, oxygen, and sulfur, a 4-7 membered saturated heterocyclic ring having 1-5 heteroatoms independently selected from boron, silicon, phosphorus, nitrogen, oxygen, and sulfur, a 7-10 membered bicyclic saturated heterocyclic ring having 1-5 heteroatoms independently selected from boron, silicon, phosphorus, nitrogen, oxygen, and sulfur, and an 8-10 membered bicyclic heteroaryl ring having 1-5 heteroatoms independently selected from boron, silicon, phosphorus, nitrogen, oxygen, and sulfur.

In some embodiments, a second double bond is a terminal olefin. In some embodiments, a second species has the structure of R$^t$—CH=CH$_2$. In some embodiments, a second species has the structure of R$^1$—CH=CH$_2$, wherein R$^1$ is an optionally substituted group selected from $C_{1-20}$ aliphatic, $C_{1-20}$ heteroaliphatic having 1-3 heteroatoms independently selected from nitrogen, oxygen, and sulfur, phenyl, a 3-7 membered saturated carbocyclic ring, an 8-10 membered bicyclic saturated ring, or aryl ring, a 5-6 membered monocyclic heteroaryl ring having 1-4 heteroatoms independently selected from nitrogen, oxygen, and sulfur, a 4-7 membered saturated heterocyclic ring having 1-3 heteroatoms independently selected from nitrogen, oxygen, and sulfur, a 7-10 membered bicyclic saturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, a second double bond is not a terminal olefin. In some embodiments, a second double bond is an internal double bond. In some embodiments, a second double bond is a double bond within a ring of the second species, wherein a ring-opening metathesis reaction is performed. In some embodiments, a second species comprises a =CHR$^t$ moiety, wherein the double bond is the second double bond. In some embodiments, R$^t$ is R, wherein R is optionally substituted $C_{1-6}$ alkyl. In some embodiments, a second species comprises a =CHR moiety, wherein the double bond is the second double bond. In some embodiments, R is unsubstituted $C_{1-6}$ alkyl. In some embodiments, R is methyl. In some embodiments, R is ethyl. In some embodiments, a second species comprises a =CHMe moiety, wherein the double bond is the second double bond. In some embodiments, a second species comprises a =CHEt moiety, wherein the double bond is the second double bond. In some embodiments, the double bond in =CHR$^t$ is cis. In some embodiments, the double bond in =CHR$^t$ is Z.

In some embodiments, a second species comprises a —CH=CHR$^t$ moiety, wherein the double bond is the second double bond. In some embodiments, a second species comprises a —CH=CHR moiety, wherein the double bond is the second double bond. In some embodiments, R is unsubstituted $C_{1-6}$ alkyl. In some embodiments, R is methyl. In some embodiments, R is ethyl. In some embodiments, a second species comprises a —CH=CHMe moiety, wherein the double bond is the second double bond. In some embodiments, a second species comprises a —CH=CHEt moiety, wherein the double bond is the second double bond. In some embodiments, the double bond in —CH=CHR$^t$ is cis. In some embodiments, the double bond in —CH=CHR$^t$ is Z. In some embodiments, a second species comprises a

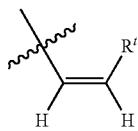

moiety, wherein the double bond is the second double bond. In some embodiments, a second species comprises a

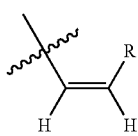

moiety, wherein the double bond is the second double bond. In some embodiments, a second species comprises a

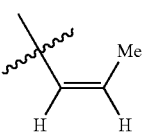 [SMILES: */C=C\C]

moiety, wherein the double bond is the second double bond. In some embodiments, a second species comprises a

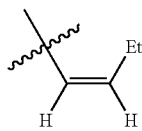 [SMILES: */C=C\CC]

moiety, wherein the double bond is the second double bond.

In some embodiments, a first species of a provided olefin metathesis method is an alkenyl halide, wherein each carbon of the alkene group is independently substituted with a halogen atom. In some embodiments, the two halogen atoms on the two carbon atoms of the double bond are cis. In some embodiments, the two halogen atoms on the two carbon atoms of the double bond are cis, and the at least one product comprises a carbon atom from the olefin of the first species and the halogen atom attached to the carbon atom, and the at least one product is produced with Z-selectivity. In some embodiments, the two halogen atoms on the two carbon atoms of the double bond are trans. In some embodiments, the two halogen atoms on the two carbon atoms of the double bond are trans, and the at least one product comprises a carbon atom from the olefin of the first species and the halogen atom attached to the carbon atom, and the at least one product is produced with E-selectivity.

In some embodiments, each carbon atom of the first double bond is substituted with a first substituent. In some embodiments, a first double bond has an E configuration with respect to the two first substituents. In some embodiments, a first species has the structure of

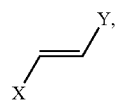

wherein each of X and Y is independently a first substituent. In some embodiments, one of X and Y is —F and the other is —Cl. In some embodiments, one of X and Y is —F and the other is —Br. In some embodiments, each of X and Y is independently $C_{1-6}$ haloalkyl. In some embodiments, each of X and Y is independently —CF(X')$_2$. In some embodiments, the first two substituents, e.g., X and Y, are the same. In some embodiments, each of X and Y is —CF$_3$ or —C$_2$F$_5$ or —C$_3$F$_7$ or —C$_4$F$_9$ or —C$_5$F$_{11}$ or —C$_6$F$_{13}$.

In some embodiments, when a first double bond is E, provided methods may form at least one product comprising a third double bond with E selectivity.

In some embodiments, a third double bond in a product is formed by metathesis of a first double bond and a second double bond. In some embodiments, a third double bond comprises a carbon atom from the first double bond, and a carbon atom from the second double bond. In some embodiments, the carbon atom from the first double bond has a first substituent as in the first double bond, and the carbon atom from the second double bond has its one or two substituents as in the second double bond.

In some embodiments, a provided method comprises ring-opening cross metathesis (ROCM).

In some embodiments, X and Y may be identical or different, and are —H, —F, —Cl, —Br, or —I, but they are not —H at the same time.

In some embodiments, X and Y may be identical or different, and are —H, or —CF$_3$, but are not —H at the same time.

In some embodiments, a provided method comprises cross metathesis.

In some embodiments, provided methods provide regioselectivity. In some embodiments, provided methods provide stereoselectivity or provide regioselectivity and stereoselectivity. In some embodiments, provided methods provide regioselectivity and Z-selectivity.

In some embodiments, a provided compound, e.g., a compound of formula I-a, a compound of formula I-b, etc. is isolated prior to the use in the metathesis reaction. In some embodiments, when used as a solid, a provided compound, e.g., a compound of formula I-a, a compound of formula I-b, etc. is purified. In some embodiments, a provided compound, e.g., a compound of formula I-a, a compound of formula I-b, etc. is added as substantially pure form as a solid and/or solution. In some embodiments, the purity is greater than 50% or 70% or 80% or 90% with respect to the metal in that, for example, 50 mol % of the metal-containing compound in the solid and/or solution is a compound of formula I-a or a compound of formula I-b. In some embodiments, the purity is greater than 91% or 92% or 94% or 96% or 98% or 99%.

In some embodiments, when used in solution, a provided compound, e.g., a compound of formula I-a, or a compound of formula I-b, etc. may not be isolated and may be generated in situ and used without isolation from a solution.

In some embodiments, the present disclosure provides a composition comprising

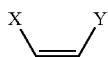

and a compound having the structure of formula I-a or I-b. In some embodiments, the present disclosure provides a composition comprising

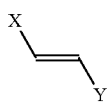

and a compound having the structure of formula I-a or I-b.

In some embodiments, the present disclosure provides a composition comprising a compound having the structure of formula I-a or I-b and a first species comprising a first double bond, wherein a carbon atom of the first double bond is substituted with a first substituent selected from halogen and optionally substituted $C_{1-6}$ haloalkyl. In some embodiments, the present disclosure provides a composition comprising a compound having the structure of formula I-a or I-b and a first species comprising a first double bond, wherein a carbon atom of the first double bond is substituted with a first substituent which is halogen. In some embodiments, the present disclosure provides a composition comprising a compound having the structure of formula I-a or I-b and a first species having the structure of

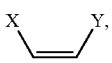

wherein each of X and Y is independently halogen. In some embodiments, X and Y are the same. In some embodiments, the present disclosure provides a composition comprising a compound having the structure of formula I-a or I-b and a first species comprising a first double bond, wherein a carbon atom of the first double bond is substituted with a first substituent which is optionally substituted $C_1$ haloalkyl. In some embodiments, the present disclosure provides a composition comprising a compound having the structure of formula I-a or I-b and a first species having the structure of

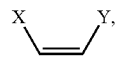

wherein each of X and Y is independently optionally substituted $C_{1-6}$ haloalkyl such as optionally substituted $C_{1-6}$ haloalkyl. In some embodiments, X and Y are —$CF_3$ or —$C_2F_5$ or —$C_3F_7$ or —$C_4F_9$ or —$C_5F_{11}$ or —$C_6F_{13}$.

In some embodiments, the present disclosure provides a composition comprising a first species comprising a first double bond, wherein a carbon atom of the first double bond is substituted with a first substituent selected from halogen and optionally substituted $C_{1-6}$ haloalkyl, and one or more compounds selected from a compound comprising molybdenum or tungsten, $R^4OH$ or a salt thereof, and $R^5H$ or a salt thereof. In some embodiments, the present disclosure provides a composition comprising a first species comprising a first double bond, wherein a carbon atom of the first double bond is substituted with a first substituent selected from halogen and optionally substituted $C_{1-6}$ haloalkyl, and a compound comprising molybdenum or tungsten. In some embodiments, the present disclosure provides a composition comprising a first species comprising a first double bond, wherein a carbon atom of the first double bond is substituted with a first substituent selected from halogen and optionally substituted $C_1$ haloalkyl such as optionally substituted $C_1$ haloalkyl, and a compound selected from $R^4OH$ or a salt thereof, and $R^5H$ or a salt thereof. In some embodiments, the present disclosure provides a composition comprising a first species comprising a first double bond, wherein a carbon atom of the first double bond is substituted with a first substituent selected from halogen and optionally substituted $C_{1-6}$ haloalkyl, and $R^4OH$ or a salt thereof. In some embodiments, the present disclosure provides a composition comprising a first species comprising a first double bond, wherein a carbon atom of the first double bond is substituted with a first substituent selected from halogen and optionally substituted $C_{1-6}$ haloalkyl, and $R^5H$ or a salt thereof. In some embodiments, $R^4OH$ or a salt thereof, and/or $R^5H$ or a salt thereof, is generated, or introduced, when preparing a compound, e.g., a compound of formula I-a, a compound of formula I-b, etc. In some embodiments, $R^4OH$ or a salt thereof, and/or $R^5H$ or a salt thereof, is generated when a compound, e.g., a compound of formula I-a, a compound of formula I-b, etc., degrades and/or is quenched when a metathesis reaction reaches a desired stage. In some embodiments, each carbon atom of the first double bond is independently substituted with a first substituent selected from halogen and optionally substituted $C_{1-6}$ haloalkyl. In some embodiments, a first substituent is independently halogen. In some embodiments, a first substituent is optionally substituted $C_{1-6}$ haloalkyl.

In some embodiments, a provided composition comprises CHR=CHCF₃. In some embodiments, a provided composition comprises (Z)—CHR=CHCF₃. In some embodiments, a provided composition comprises CH₃CH=CHCF₃. In some embodiments, a provided composition comprises (Z)—CH₃CH=CHCF₃. In some embodiments, a provided composition comprises $C_2H_5CH=CHCF_3$. In some embodiments, a provided composition comprises (Z)—$C_2H_5CH=CHCF_3$. In some embodiments, a provided composition comprises $CH_2=CHCF_3$.

In some embodiments, a provided method generates $CHR=CHCF_3$. In some embodiments, a provided method generates (Z)—$CHR=CHCF_3$. In some embodiments, a provided method generates $CH_3CH=CHCF_3$. In some embodiments, a provided method generates (Z)—$CH_3CH=CHCF_3$. In some embodiments, a provided method generates $C_2H_5CH=CHCF_3$. In some embodiments, a provided method generates (Z)—$C_2H_5CH=CHCF_3$. In some embodiments, a provided method generates $CH_2=CHCF_3$.

In some embodiments, a ligand is provided in a molar ratio of about 10:1, 9:1, 8:1, 7:1, 6:1, 5:1, 4:1, 3:1, 2:1, or 1:1 relative to the metal. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, dimethoxy ethane (DME), tetrahydrofuran (THF), or dioxanes, or protic solvents, such as alcohols, or mixtures thereof. In certain embodiments, one or more solvents are deuterated.

In some embodiments, a single solvent is used. In certain embodiments, a solvent is benzene. In certain embodiments, a solvent is ether. In some embodiments, a solvent is a nitrile. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. In some embodiments, an exemplary mixture is a DME/Toluene mixture. In some embodiments, an exemplary mixture is DME/Toluene about 1:1. Solvent mixtures may be comprised of equal volumes of each solvent or may contain one solvent in excess of the other solvent or solvents. Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C.

In certain embodiments, a provided method is performed at elevated temperature. In some embodiments, a suitable temperature is from about 25° C. to about 110° C. In certain embodiments, a provided method is performed at temperature lower than ambient temperatures. In some embodiments, a suitable temperature is from about −100° C. to about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C.

Suitable conditions typically involve reaction times of about 1 minute to about one or more days. In some embodiments, the reaction time ranges from about 0.5 hour to about 72 hours In some embodiments, a provided metal complex compound of formula I-a or I-b or an active catalyst formed from a provided compound, is stable under metathesis conditions.

Some embodiments may provide the ability to selectively synthesize, via a metathesis reaction, products having a Z configuration about a double bond. Some embodiments may provide the ability to selectively synthesize, via a metathesis reaction, products having a Z configuration about a double bond. Some embodiments may provide the ability to selectively synthesize, via a metathesis reaction, products having a E configuration about a double bond. In some embodiments, such methods are useful when applied to a wide range of olefin substrates, including those having sterically small or large groups adjacent the olefin. In some embodiments, the substrate olefins are terminal olefins. In some embodiments, one of the substrate olefin is terminal olefin.

In some embodiments, the present disclosure provides methods for regioselective metathesis in that the methods selectively provide products via one of the possible metathesis pathways. In some embodiments, the present disclosure provides methods for regioselective synthesis of alkenyl fluoride using 1-bromo-2-fluoroethylene or 1-chloro-2-fluoroethylene. In some embodiments, provided methods further provide Z- or E-selectivity. In some embodiments, the regioselectivity is greater than about 2:1, 3:1, 4:1, 5:1, 6:1, 7:1, 8:1, 9:1, 10:1, 20:1, 30:1, 40:1 50:1 or 100:1. In some embodiments, the regioselectivity is greater than about 2:1. Exemplary reactions are described below.

In some embodiments, the present disclosure provides a method for Z-selective metathesis reactions. In some embodiments, a provided method produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, a provided method requires an amount of a provided compound (e.g., a metal complex having the structure of formula I-a or I-b) such that the loading is from about 0.01 mol % to about 20 mol % of the provided compound relative to substrate (e.g., a first or second double bond). In certain embodiments, a provided compound is used in an amount of between about 0.01 mol % to about 10 mol %. In certain embodiments, a provided compound is used in an amount of between about 0.01 mol % to about 6 mol %. In certain embodiments, a provided compound is used in an amount of between about 0.01 mol % to about 5 mol %. In certain embodiments, a provided compound is used in an amount of between about 0.01 mol % to about 4 mol %. In certain embodiments, a provided compound is used in an amount of between about 0.01 mol % to about 3 mol %. In certain embodiments, a provided compound is used in an amount of between about 0.01 mol % to about 1 mol %. In certain embodiments, a provided compound is used in an amount of between about 0.01 mol % to about 0.5 mol %. In certain embodiments, a provided compound is used in an amount of between about 0.01 mol % to about 0.2 mol %. In certain embodiments, a provided compound is used in an amount of about 0.05%, 0.1%, 0.2%, 0.5%, 1%, 2%, 3 mol %, 4 mol %, 5 mol %, 6 mol %, 7 mol %, 8 mol %, 9 mol %, or 10 mol %.

In some embodiments, a method of the present disclosure requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present disclosure is performed at ambient pressure. In some embodiments, a method of the present disclosure is performed at reduced pressure. In some embodiments, a method of the present disclosure is performed at a pressure of less than about 20 torr. In some embodiments, a method of the present disclosure is performed at a pressure of less than about 15 torr. In some embodiments, a method of the present disclosure is performed at a pressure of less than about 10 torr. In some embodiments, a method of the present disclosure is performed at a pressure of about 9, 8, 7, 6, 5, 4, 3, 2, or 1 torr. In certain embodiments, a method of the present disclosure is performed at a pressure of about 7 torr. In certain embodiments, a method of the present disclosure is performed at a pressure of about 1 torr.

In some embodiments, a method of the present disclosure is performed at increased pressure. In some embodiments, a method of the present disclosure is performed at greater than about 1 atm. In some embodiments, a method of the present disclosure is performed at greater than about 2 atm. In some embodiments, a method of the present disclosure is performed at greater than about 3 atm. In some embodiments, a method of the present disclosure is performed at greater than about 5 atm. In some embodiments, a method of the present disclosure is performed at greater than about 10 atm. In some embodiments, a method of the present disclosure is performed at about 2 atm or about 3 atm or about 5 atm or about 10 atm.

In some embodiments, the present disclosure recognizes that ratios of metathesis substrates may have impact on the reaction results, e.g., yield, regioselectivity, stereoselectivity (e.g., Z-selectivity, E-selectivity, etc.), etc. In some embodiments, provided technologies, e.g., compounds, methods, etc. provide high tolerance of molar ratio of substrates. In some embodiments, provided technologies deliver high yield and high selectivity (e.g., regioselectivity, stereoselectivity, chemoselectivity, etc., across a wide range of molar ratios of substrates.

The inventors of the present disclosure surprisingly discovered that, in one embodiment, the activity of the MAX catalyst used in the method according to the disclosure, i.e. the reactivity of the metathesis reaction as such, may be increased by adding a co-catalyst.

Preferably, suitable co-catalysts are selected from the group consisting of: trityl tetrakis(pentafluorophenyl)borate [$(C_6H_5)_3CB(C_6F_5)_4$], sodium tetrakis[3,5-bis(trifluoromethyl)phenyl]borate [$Na(B[3,5-(CF_3)_2C_6H_3]_4)$], tris(pentafluorophenyl)boron [$B(C_6F_5)_3$], dimethylanilinium tetrakis(pentafluorophenyl) borate [$PhNMe_2HB(C_6F_5)_4$], and CuCl. The compounds are known and commercially available.

In one embodiment, such co-catalyst is e.g. effective in increasing the reactivity of MAX complexes bearing a phosphine as the neutral ligand.

According to a THIRD ASPECT, the present disclosure provides a method for preparing a compound of formula I-a, comprising steps of:

(a) providing a first compound of formula II:

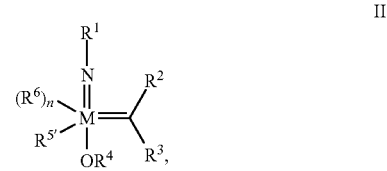

(b) providing a second compound having the structure of $R^5$—CH=CH—$R^5$;

(c) reacting the first compound with the second compound in the presence of a third compound having the structure of $R^6$;

wherein:

each of $R^1$, $R^2$, $R^3$, $R^4$, $R^5$, $R^6$ and n is independently as defined and described herein; and $R^{5'}$ is —N(R')$_2$.

In some embodiments, a first compound has the structure of formula II wherein n is 0. In some embodiments, a second compound is a cis olefin. In some embodiments, $R^5$ is —Br. In some embodiments, $R^6$ is pyridine. In some embodiments, $R^5$ is —N(R')$_2$, wherein the two R' groups are taken together with the nitrogen atom to form an optionally substituted 3-8 membered, saturated ring, or aryl ring having 1-4 heteroatoms independently selected from nitrogen, oxygen, and sulfur. In some embodiments, $R^5$ is —N(R')$_2$, wherein the two R' groups are taken together with the nitrogen atom to form an optionally substituted 5-membered heteroaryl ring having 1-4 heteroatoms independently selected from nitrogen, oxygen, and sulfur. In some embodiments, $R^5$ is optionally substituted pyrrolyl. In some embodiments, $R^5$ is pyrrolyl.

In one embodiment, the present disclosure provides a method for preparing a compound of formula I-a, comprising steps of:
(a) providing a first compound of formula II:

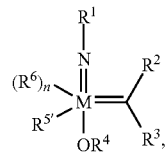

(b) providing a second compound having the structure of $R^5$—H or a salt thereof; and
(c) reacting the first compound with the second compound optionally in the presence of a third compound having the structure of $R^6$;
wherein:
each of $R^1$, $R^2$, $R^3$, $R^4$, $R^5$, $R^6$ and n is independently as defined and described herein; and
$R^{5'}$ is —N(R')$_2$.

In some embodiments, a first compound has the structure of formula II wherein n is 0. In some embodiments, $R^6$ is pyridine. In some embodiments, $R^5$ is —N(R')$_2$, wherein the two R' groups are taken together with the nitrogen atom to form an optionally substituted 3-8 membered, saturated ring, or aryl ring having 1-4 heteroatoms independently selected from nitrogen, oxygen, and sulfur. In some embodiments, $R^5$ is —N(R')$_2$, wherein the two R' groups are taken together with the nitrogen atom to form an optionally substituted 5-membered heteroaryl ring having 1-4 heteroatoms independently selected from nitrogen, oxygen, and sulfur. In some embodiments, $R^5$ is optionally substituted pyrrolyl. In some embodiments, $R^5$ is pyrrolyl.

In some embodiments, a second compound is a salt of $R^5$—H. In some embodiments, a second compound is a salt of $R^5$—H and a nitrogen-based base. In some embodiments, a nitrogen-based base has the structure of N(R')$_3$. In some embodiments, a nitrogen-based base has the structure of N(=$R^{6'}$)($R^{6'}$), wherein the two $R^{6'}$ are taken together with the nitrogen atom to form an optionally substituted 6-membered heteroaryl ring having, in addition to the nitrogen atom, 1-4 heteroatoms independently selected from nitrogen, oxygen, and sulfur. In some embodiments, a nitrogen-based base is optionally substituted pyridine. In some embodiments, a nitrogen-based base is pyridine. In some embodiments, a nitrogen-based base is substituted pyridine. In some embodiments, a nitrogen-based base is substituted pyridine, wherein one to five of the substituents are independently $R^s$. In some embodiments, a second compound is pyridinium bromide.

The present disclosure also provides a method for preparing a compound of formula I-a, wherein n is 1 or 2, comprising steps of:
(a) providing a first compound of formula III:

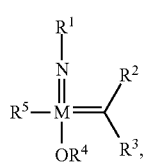

and
(b) providing a neutral ligand having the structure of $R^6$; and
(c) reacting the first compound with the neutral ligand to provide a compound of formula I-a, wherein n is 1 or 2;
wherein each variable is independently as defined described herein.

Suitable ligands are extensively described in the present disclosure. In some embodiments, $R^6$ is CH$_3$CN. In some embodiments, $R^6$ is pyridine. In some embodiments, a compound of formula III is generated in situ and used for a next step without purification.

The present disclosure provides a method for preparing a compound of formula III, comprising steps of:
(a) providing a third compound of formula IV:

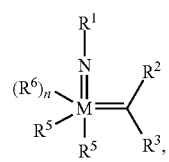

and
(b) reacting the third compound with a fourth compound having the structure of $R^4$OH or a salt thereof;
wherein each variable is independently as defined described herein.

In some embodiments, the two $R^5$ in formula IV are identical. In some embodiments, n is 2 in formula IV, and the two $R^6$ are taken together to form a bidentate ligand. In some embodiments, a bidentate ligand is 2,2'-bipyridine. In some embodiments, n is 2 and each $R^6$ is a monodentate ligand. In some embodiments, each $R^6$ is pyridine. In some embodiments, a fourth compound is a salt of $R^4$OH. In some embodiments, a fourth compound is $R^4$OLi. In some embodiments, a forth compound is HMT-OLi. In some embodiments, a reaction between the third and fourth compounds is conducted in the presence of a Lewis acid. In some embodiments, a Lewis acid is a Zn-based Lewis acid. In some embodiments, a Lewis acid is ZnCl$_2$. In some embodiments, a suitable solvent for a reaction is ether. In some embodiments, a reaction between a third and a fourth compounds is conducted at a lowered temperature (e.g., −30° C.), optionally with temperature increase gradually to room temperature.

The present disclosure provides a method for preparing a compound of formula IV, comprising steps of:
(a) providing a fifth compound of formula V:

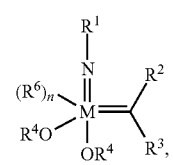

and
(b) reacting the fifth compound with a suitable sixth compound to provide a compound of formula IV;
wherein each variable is independently as defined described herein.

In some embodiments, the two $R^4$ in formula V are identical. In some embodiments, $R^4$ of formula V is optionally substituted phenyl. In some embodiments, each $R^4$ of formula V is —$C_6F_5$. As understood by a person having ordinary skill in the art, a suitable sixth compound provides $R^5$ and reacts with a fifth compound to provide a compound of formula IV. In some embodiments, a sixth compound has the structure of $(R')_3Si$—$R^5$. In some embodiments, a six compound is TMS-Cl. In some embodiments, n of formula V is 2. In some embodiments, n is 2 in formula V, and the two $R^6$ are taken together to form a bidentate ligand. In some embodiments, a bidentate ligand is 2,2'-bipyridine. In some embodiments, n is 2 and each $R^6$ is a monodentate ligand.

The present disclosure provides a method for preparing a compound of formula V, comprising steps of:
(a) providing a seventh compound of formula VI:

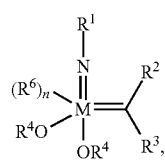

VI (b) reacting the seventh compound with an eighth compound to provide a compound of formula V;
wherein an eighth compound is a neutral ligand having the structure of $R^6$, and each variable is independently as defined described herein.

In some embodiments, n is 1 in formula VI, and $R^6$ is a monodentate ligand.

In some embodiments, $R^6$ is $NH_2$—$R^1$. In some embodiments, $R^6$ is adamantylamine. In some embodiments, the two $R^4$ in formula VI are identical. In some embodiments, $R^4$ of formula VI is optionally substituted phenyl. In some embodiments, each $R^4$ of formula VI is —$C_6F_5$. In some embodiments, an eighth compound is a bidentate ligand and n in formula V is 2. In some embodiments, an eighth compound is 2,2'-bipyridine.

The present disclosure provides a method for preparing a compound of formula VI, comprising steps of:
(a) providing a ninth compound of formula VII:

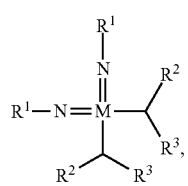

VII and
(b) reacting the ninth compound with a tenth compound having the structure of $R^4$—OH or a salt thereof to provide a compound of formula VI;
wherein each variable is independently as defined described herein.

In some embodiments, the two $R^1$ groups are the same, the two $R^2$ groups are the same, and the two $R^3$ groups are the same. In some embodiments, a tenth compound is $R^4$—OH, wherein $R^4$ is optionally substituted phenyl. In some embodiments, a tenth compound is $R^4$—OH, wherein $R^4$ is substituted phenyl wherein one or more substituents are independently an electron-withdrawing group. In some embodiments, a tenth compound is $C_6F_5OH$. In some embodiments, a compound of formula VI is generated in situ and used without purification.

Exemplary preparation methods are described in the experimental section. Compounds of formula I-b may be prepared analogously.

EXAMPLES

As exemplified herein, the present disclosure demonstrated that ring-opening/cross-metathesis (ROCM) and cross-metathesis (CM) reactions involving commercially available and inexpensive halogen-containing olefin cross-partners promoted by compounds of formula I-a or I-b surprisingly affords Z— substituted alkenes efficiently under mild conditions and with exceptional stereoselectivity. In particular, the present disclosure demonstrated that ring-opening/cross-metathesis (ROCM) and cross-metathesis (CM) reactions involving commercially available and inexpensive perfluoroalkyl, preferably $CF_3$-containing olefin cross-partners promoted by compounds of formula I-a or I-b surprisingly affords Z-trifluoromethyl-substituted alkenes efficiently under mild conditions and with exceptional stereoselectivity.

In some embodiments, provided compounds of formula I-a or I-b, e.g., Mo-based monoaryloxide monohalide complexes, may be isolated in the form of nitrile or pyridine or phosphine ($R^6$) adducts. An exemplary compound is shown in Scheme 1. The structure of this compound was confirmed by X-Ray analysis:

Scheme 1: A compound according to the disclosure (Mo MAX complex) bearing bromo as $R^5$ and pyridine as neutral ligand $R^6$.

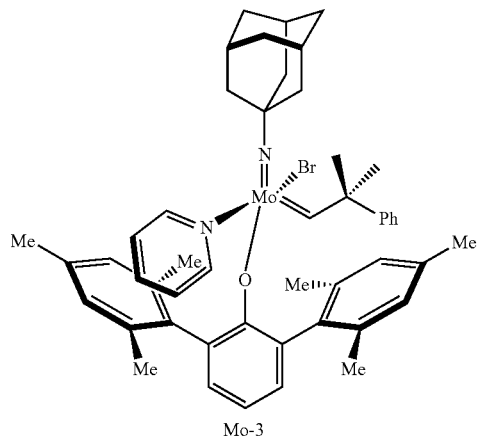

Mo-3

By means of the compounds according to the disclosure, a variety of olefins is available. Illustrative olefins are shown in Scheme 2:

Scheme 2: Examples of an olefin obtained by catalytic cross-metathesis (CM) may be used to obtain a wide range of compounds bearing a Z-trifluoromethyl-substituted alkene. (CM = cross-metathesis)

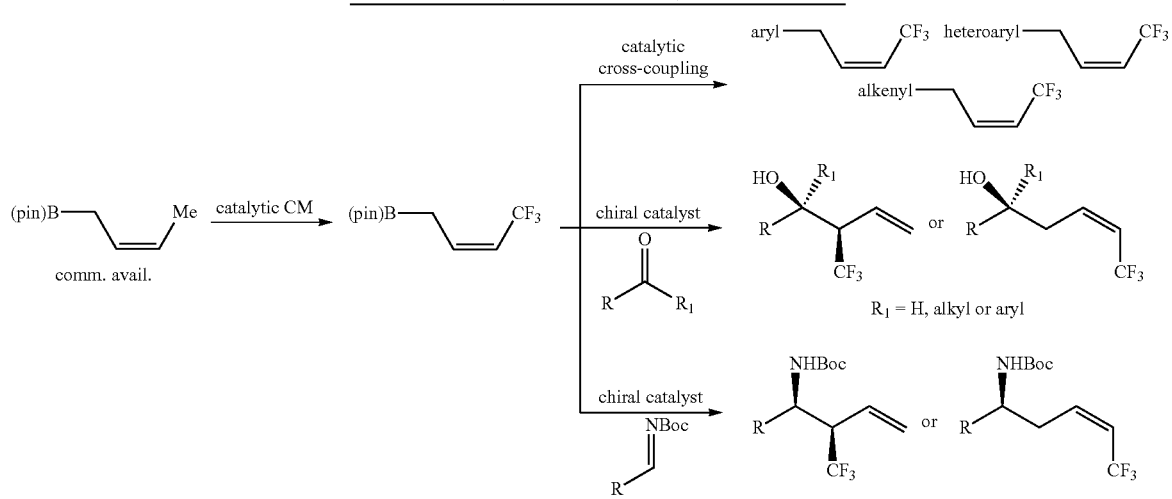

The key compounds in this chemistry are the halogen-containing Mo complexes and W complexes (MAX complexes) according to the disclosure that are capable of delivering unusual and fully unanticipated reactivity levels in catalytic CM. As the representative examples in Scheme 3 indicate, not only are MAX complexes competent in promoting efficient CM reactions that afford Z-haloalkenes, they do so with significantly higher stereoselectivity compared to the known MAP alkylidenes.

For example, in ring-opening/cross-metathesis (ROCM) reaction between cyclooctene and commercially available 1,2-dibromoethene, MAX complex Mo-2a is as efficient as the most suitable MAP system (Mo-1a) but generates the Z alkene product exclusively (>98:2 vs 88:12 Z:E) (Scheme 3). The importance of diene 7 is that it has been used in the synthesis of anti-tumor and immunosuppressive agent tetrahydrosiphonodiol. Considering the difficulty of separating olefin stereoisomers, the inventors considered this a notable finding.

The inventors then probed the ROCM reaction between Z-cyclooctene and 10 equivalents of commercially available Z-1,1,1,4,4,4-hexafluoro-2-butene in the presence of 5.0 mol % MAX complex Mo-2a. The inventors observed that with the MAX complex, after one hour at ambient temperature, the desired ROCM product 8 is formed in 13% yield (by $^1$H NMR yield) and 79:21 Z:E selectivity. This is surprising in view of the fact that the inventors had earlier found that in the presence of a large number of other Ru-, Mo- and W-based catalysts (including recently developed Z-selective Ru carbenes and various MAP systems) there is only ring-opening metathesis polymerization (ROMP) of cyclooctene without generation of even trace amounts of monomeric ROCM product.

Scheme 3: Findings regarding CM and ring-opening/cross-metathesis (ROCM) with halogen-containing alkene substrates. MAX alkylidene Mo-2a and Mo-2b are more selective than MAP complexes in CM and ROCM with 1,2-dichloro- and dibromoethene. The ROCM reaction with Z-1,1,1,4,4,4-hexafluoro-2-butene generates detectable amounts of 8 with an appreciable degree of Z

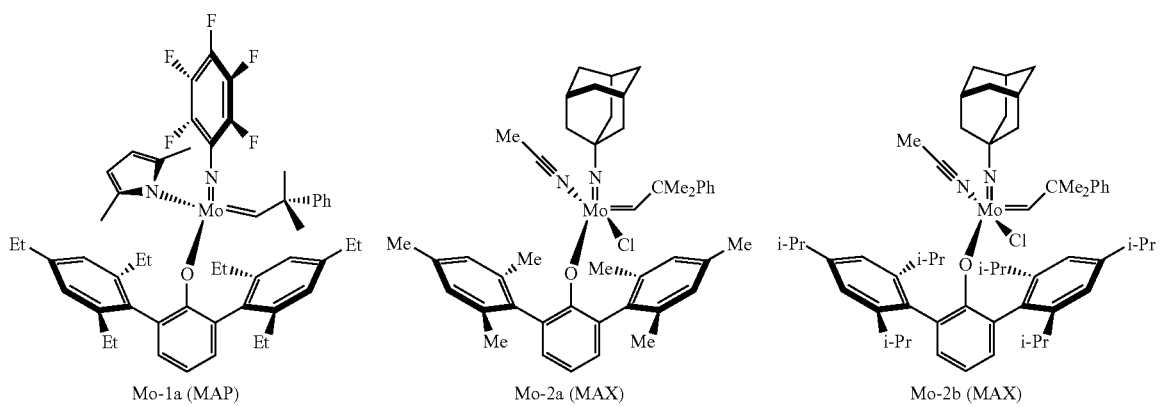

-continued

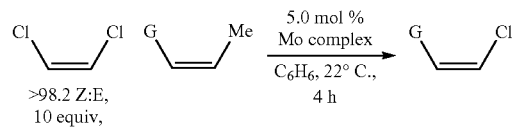

>98.2 Z:E,
10 equiv,
used as received 5.0 mol %
Mo complex
C₆H₆, 22° C.,
4 h

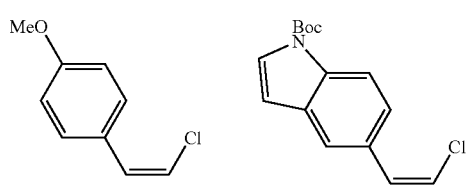

1
with Mo-1:
> 98% conv, 34% conv to 1,
52:48 Z:E
with Mo-2b:
> 98% conv, 80% yield,
> 98:2 Z:E 2
with Mo-1:
> 98% conv, 73% conv to 2,
28:72 Z:E
with Mo-2b:
> 98% conv, 83% yield,
> 98:2 Z:E

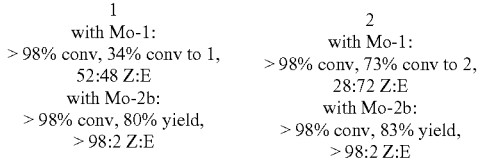

3
with Mo-1:
> 98% conv, 31% conv to 3,
53% conv to β-chlorostyrene,
Z:E ND
with Mo-2b:
> 98% conv, 83% yield,
> 98:2 Z:E 4
with Mo-1:
> 98% conv, 72% conv to 4,
87:13 Z:E
with Mo-2a:
> 98% conv, 88% yield,
> 98:2 Z:E

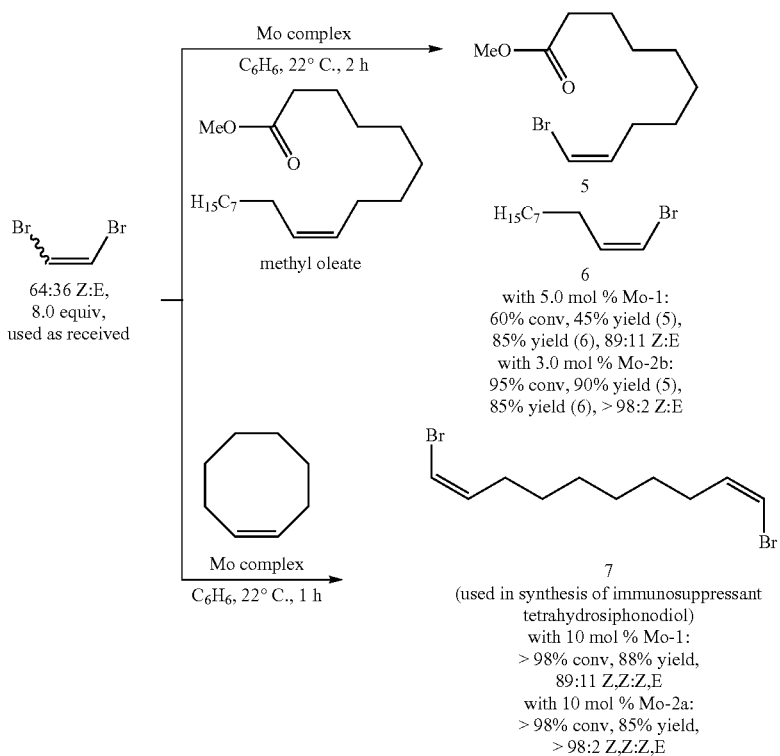

5

6
with 5.0 mol % Mo-1:
60% conv, 45% yield (5),
85% yield (6), 89:11 Z:E
with 3.0 mol % Mo-2b:
95% conv, 90% yield (5),
85% yield (6), > 98:2 Z:E 7
(used in synthesis of immunosuppressant
tetrahydrosiphonodiol)
with 10 mol % Mo-1:
> 98% conv, 88% yield,
89:11 Z,Z:Z,E
with 10 mol % Mo-2a:
> 98% conv, 85% yield,
> 98:2 Z,Z:Z,E

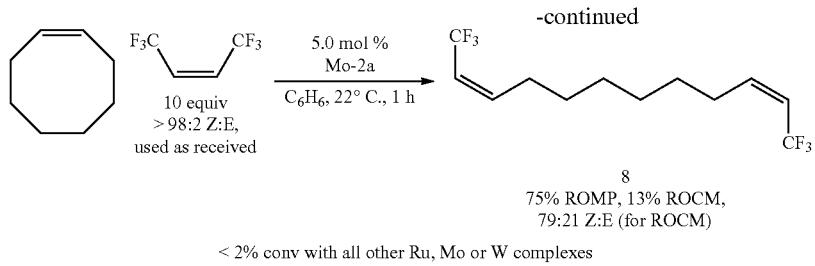

8
75% ROMP, 13% ROCM,
79:21 Z:E (for ROCM)

< 2% conv with all other Ru, Mo or W complexes selectivity; this observation is in stark contrast to when other existing Ru-, Mo- or W-based complexes are utilized (<2% ROCM detected, exclusive ROMP). Abbreviations: G, various functional groups; Ph, phenyl; pin, pinacolato; Boc, tert-butoxycarbonyl; ND, not determined [in the reaction scheme Mo-1=Mo-1a (MAP)].

The inventors subsequently assessed the ability of such modified MAX complexes to promote CM of Z-methyl oleate and Z-1,1,1,4,4,4-hexafluoro-2-butene (Scheme 4). In the presence of 20 equivalents of the hexafluoroalkene reagent, Mo-2a and Mo-2c promoted CM to give trifluoro-substituted alkenes 9 and 10 with appreciable efficiency and higher stereoselectivity was observed with Mo-2a (91:9 vs 81:19 Z:E, respectively). The most optimal results were obtained with MAX complex Mo-2d: products 9 and 10 were isolated in 90% and 65% yield, respectively with complete Z selectivity. It should be noted that the lower yield of 10 is due to its volatility.

Scheme 4:| Cross-metathesis (CM) of methyl oleate and Z-1,1,1,4,4,4-hexafluoro-2-butene with the Mo MAX complexes. Catalytic CM of methyl oleate in the presence of excess the hexafluorobutene reagent was most efficient and stereoselective with Mo-2d, which delivered the CM products in 95% and 67% yield and with complete Z selectivity (E alkene was not detected). Abbreviations: Ph, phenyl; nd, not determined.

Brief screening:

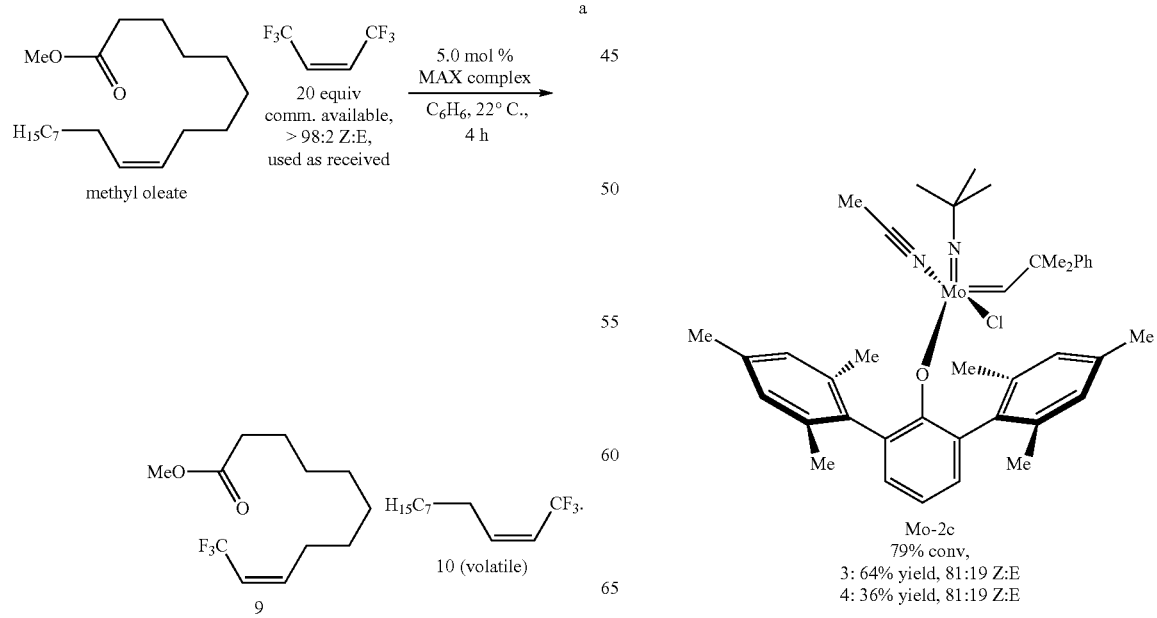

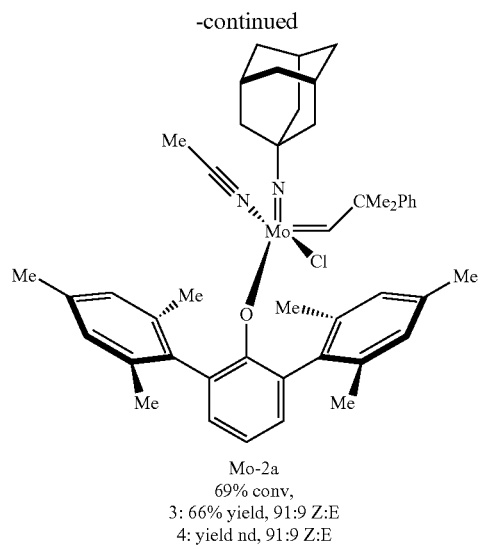

Mo-2a
69% conv,
3: 66% yield, 91:9 Z:E
4: yield nd, 91:9 Z:E

Mo-2c
79% conv,
3: 64% yield, 81:19 Z:E
4: 36% yield, 81:19 Z:E

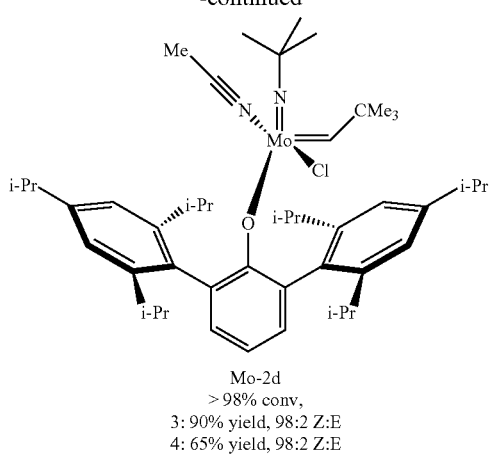

Mo-2d
>98% conv,
3: 90% yield, 98:2 Z:E
4: 65% yield, 98:2 Z:E

Optimized conditions:

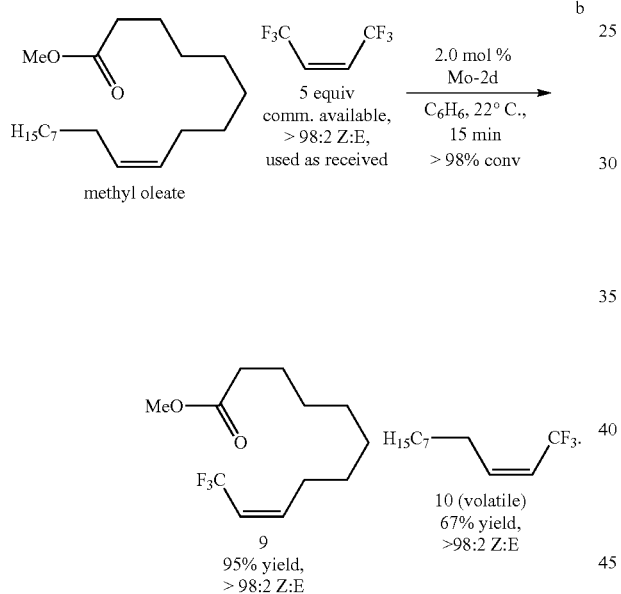

Scheme 5: CM of Z-1,1,1,4,4,4-hexafluoro-2-butene with Z-1,2-disubstituted alkenes. CM promoted by Mo-2d with various Z-1,2-disubstituted alkenes were found to be efficient and stereoselective, generating predominantly Z-alkene products in 62-98% yield. Reactions with aryl olefins and α-branched aliphatic

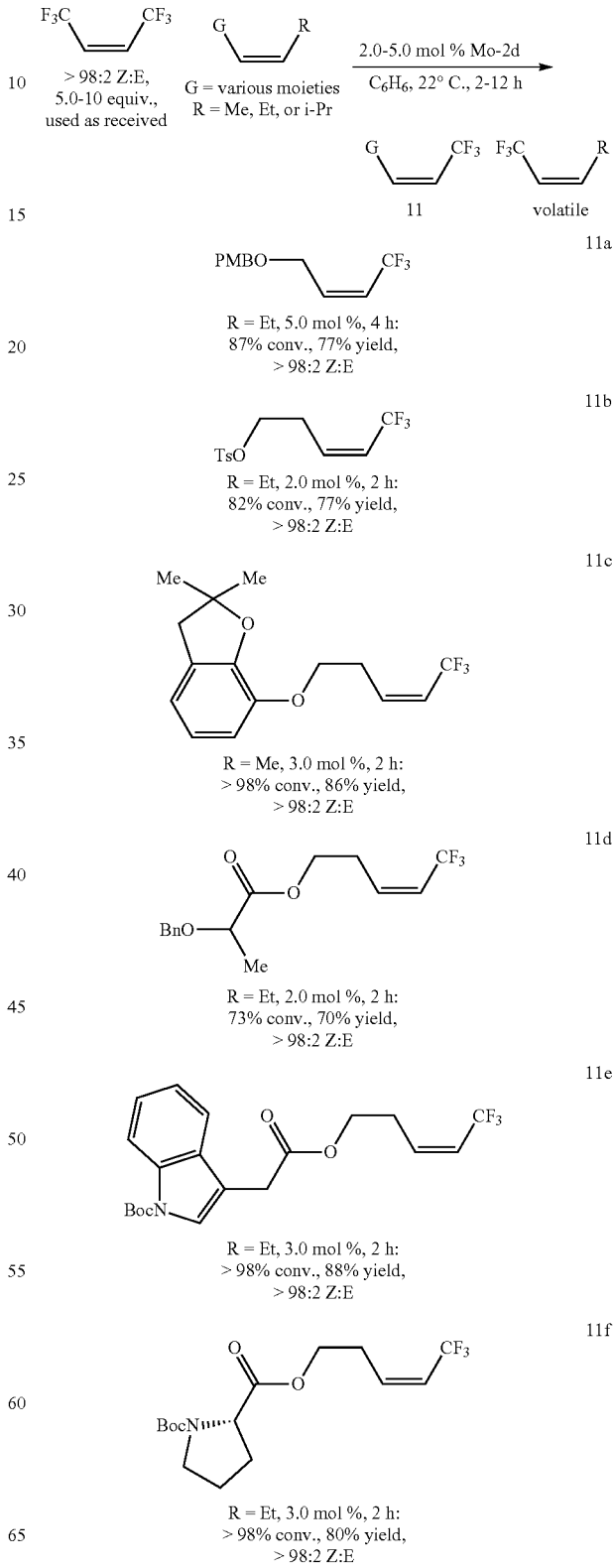

Further optimization of conditions led the inventors to establish that through the use of 2.0 mol % Mo-2d, trifluoromethyl-substituted alkenes 9 and 10 can be obtained in 67 and 95% yield and >98:<2 Z:E ratio after only 15 minutes at room temperature. It should be noted that, similar to Mo MAP complexes, the inventors found that use of air-stable paraffin tablets that contain a MAX species led to the formation of the desired products in similar yields and selectivities as that obtained otherwise. Thus, a glove box is not needed when a Mo MAX complex is employed.

Various readily available Z-1,2-disubstituted olefins may be used as starting materials. The inventors thus investigated the generality of the CM protocol with a variety of Z-1,2-disubstituted alkenes (Scheme 5). The inventors found that through the use of 2.0-5.0 mol % Mo-2d, the desired trifluoromethyl-substituted olefins, containing a number of different useful and desirable functional groups, could be secured in 62 to 98% yield and with 94:6 Z:E selectivity.

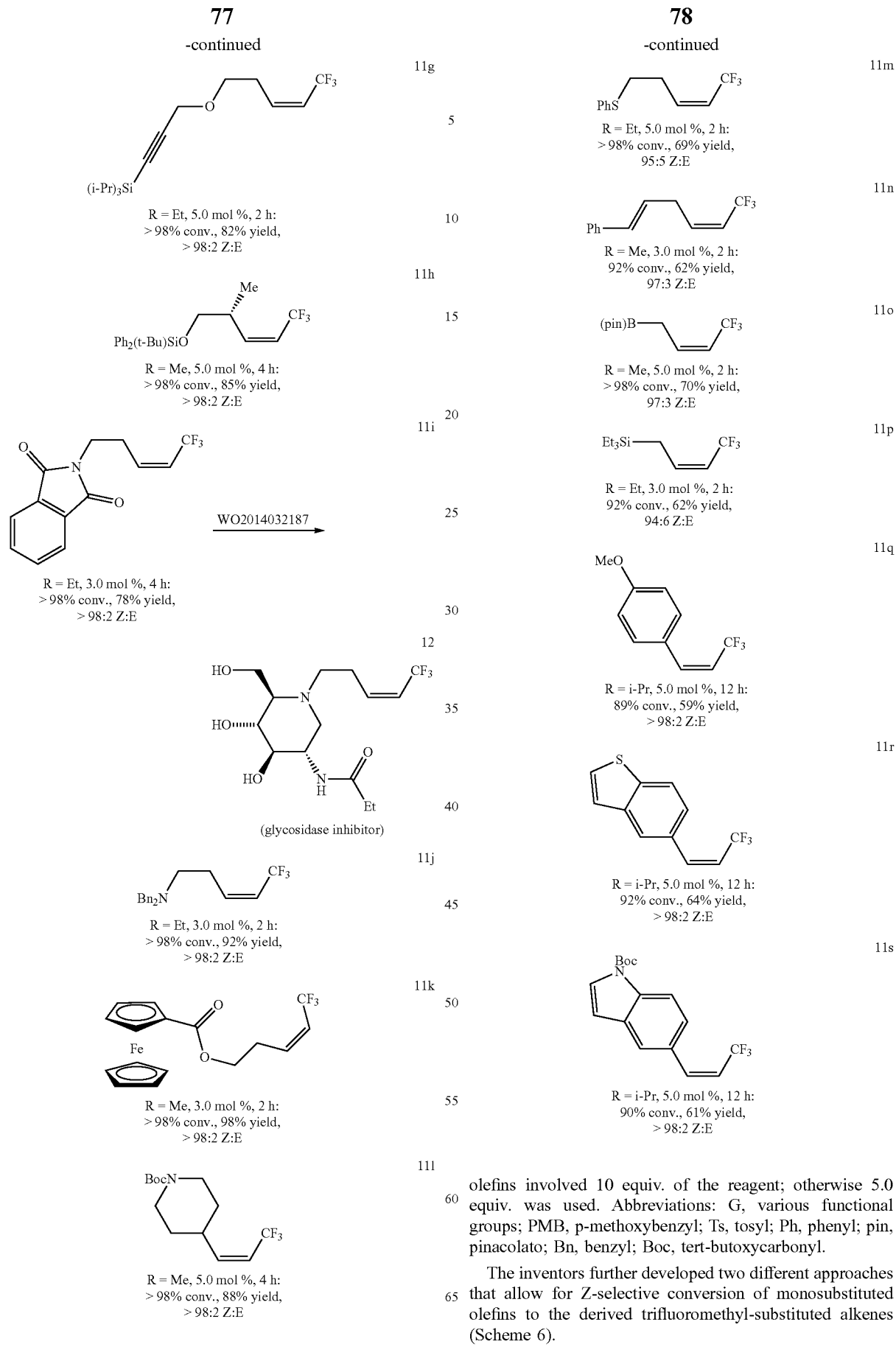

olefins involved 10 equiv. of the reagent; otherwise 5.0 equiv. was used. Abbreviations: G, various functional groups; PMB, p-methoxybenzyl; Ts, tosyl; Ph, phenyl; pin, pinacolato; Bn, benzyl; Boc, tert-butoxycarbonyl.

The inventors further developed two different approaches that allow for Z-selective conversion of monosubstituted olefins to the derived trifluoromethyl-substituted alkenes (Scheme 6).

Scheme 6: Two approaches for CM reactions with alkenes.
Two-catalyst approach:
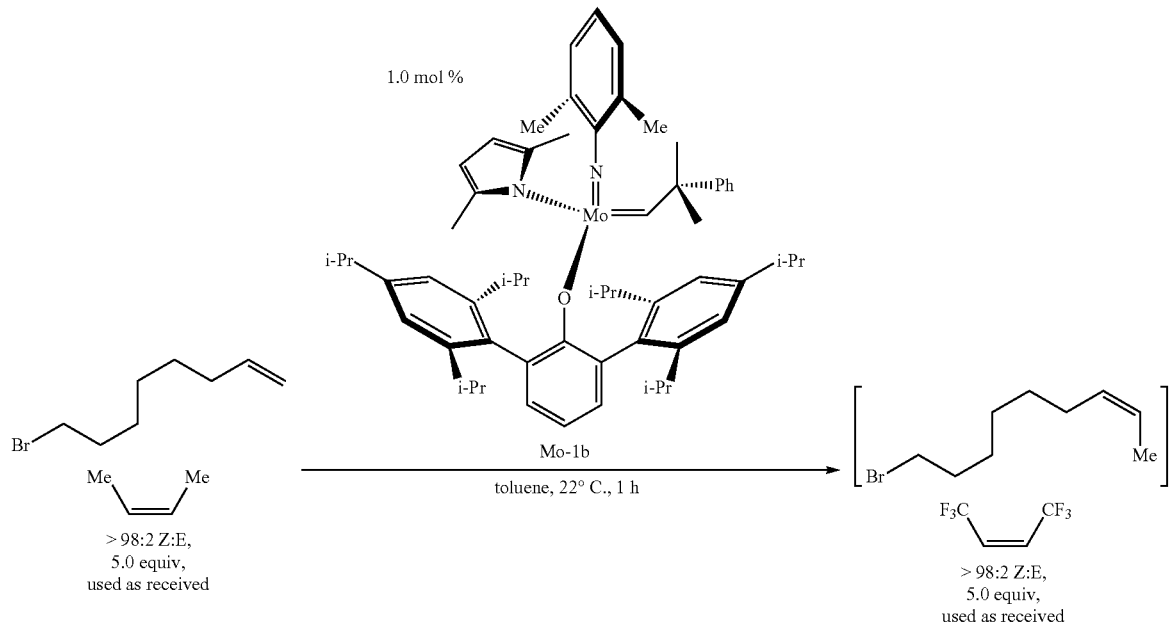

Single catalyst approach:

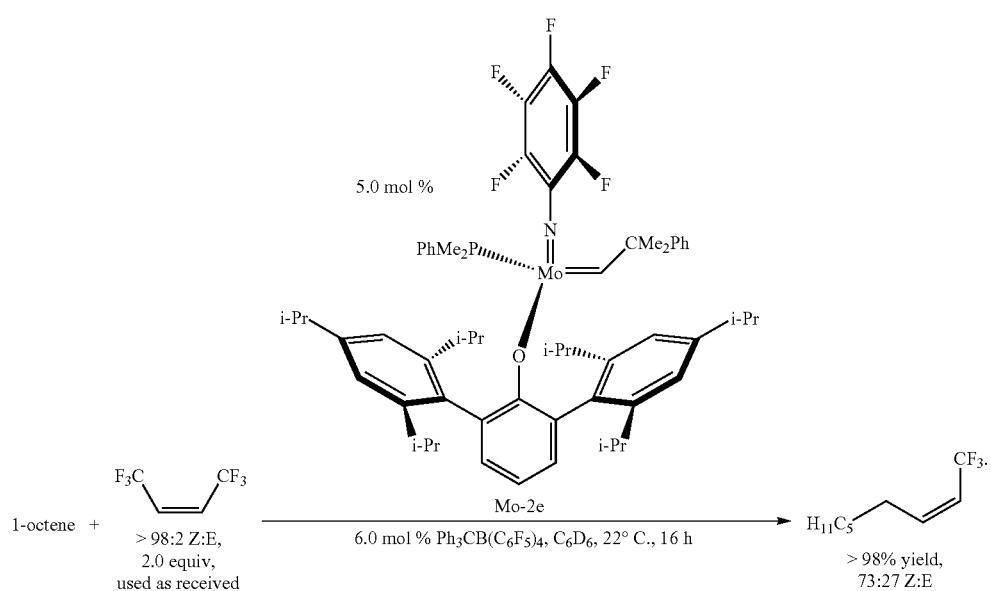

b

In one approach, involving a MAP and a MAX complex, the substrate was first induced to undergo reaction with commercially available, inexpensive and readily removable Z-2-butene using a MAP catalyst; after simple filtration, the resulting disubstituted internal alkene was then converted to the desired products through treatment with a MAX complex.

In an alternative approach entailing the use of a single catalyst, e.g. a phosphine-containing MAX complex and an appropriate co-catalyst [Ph$_3$CB(C$_6$F$_5$)$_4$] were employed to obtain the expected compound directly from a terminal olefin.

The new Mo-chloro (MAX) complexes and their ability to promote efficient CM reactions that afford Z-trifluoromethyl-substituted alkenes are expected to facilitate substantially the preparation of a variety of biologically active molecules. The examples illustrated in Scheme 7a, relating to synthesis of hvR1 receptor inhibitor 16 is a case in point. What is more, and perhaps more importantly, the present catalytic approach allows for catalytic site- and stereoselective late-stage insertion of a trifluoromethyl unit within the structures of biologically active molecules. The examples illustrated in Scheme 7b (cf. 19, and 21-25) not only underscore this latter application, they demonstrate the functional group compatibility of the MAX complexes.

Scheme 7: A representative application to synthesis of a biologically active molecule, examples regarding incorporation of a trifluoromethyl group with a highly functionalized complex system, and illustration of functional group compatibility.

a. Application to synthesis of a biologically active molecule

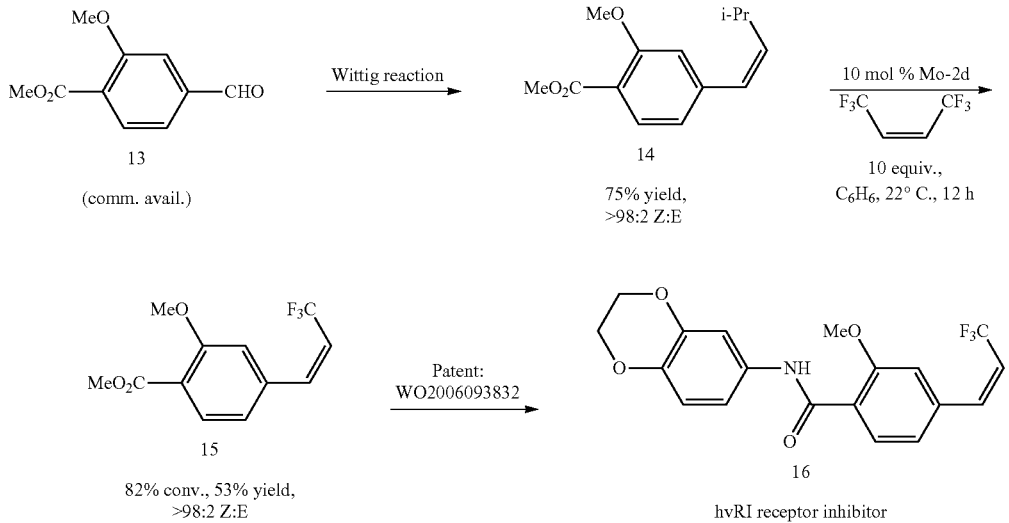

b. Examples regarding modification of biologically active compounds:
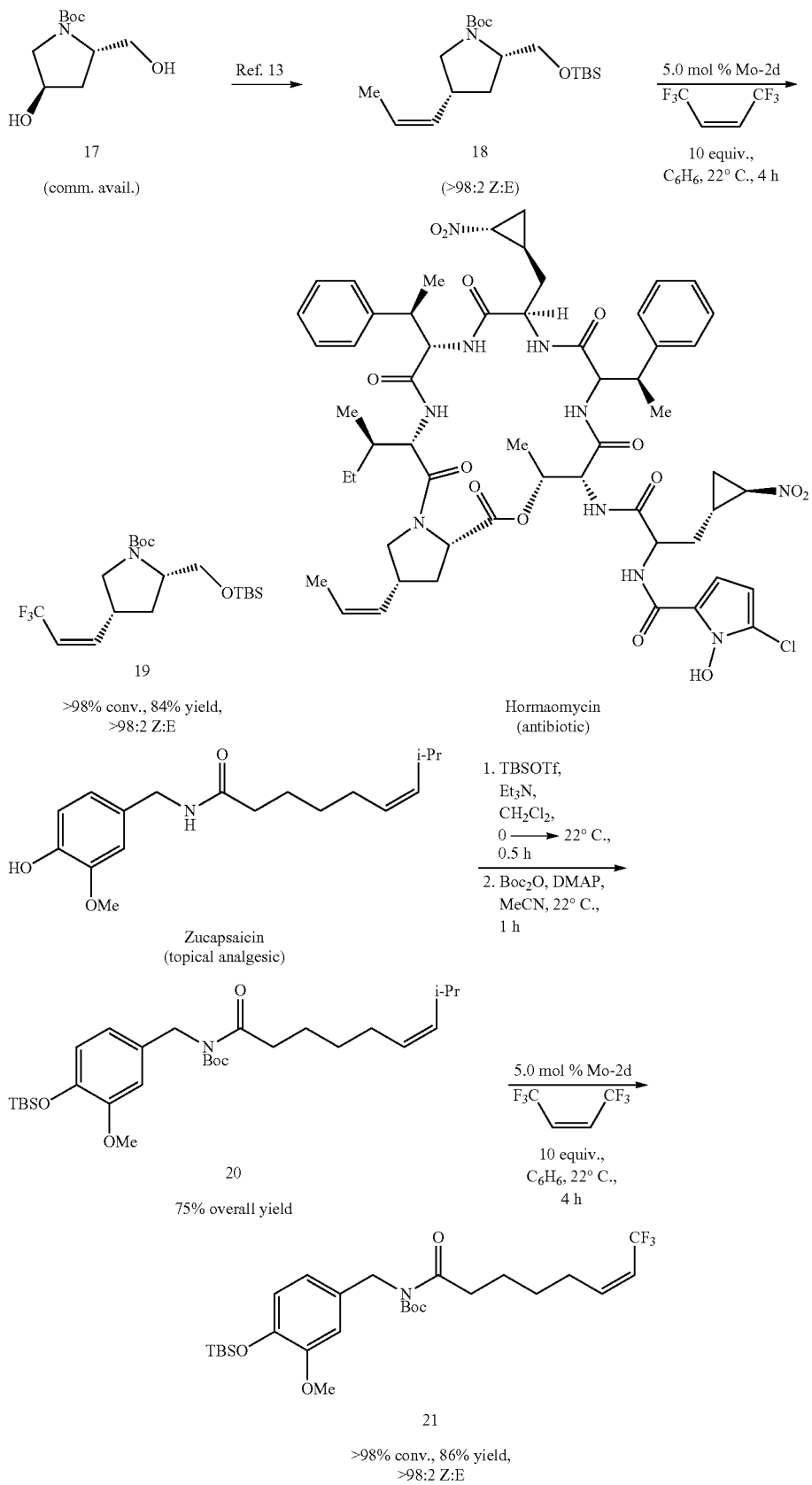

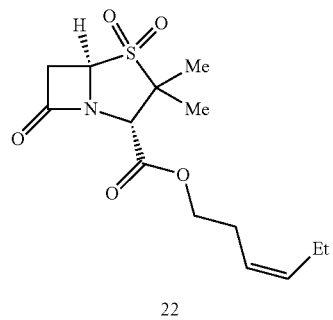
22
(derived from sulbactam, a β-lactamase inhibitor)
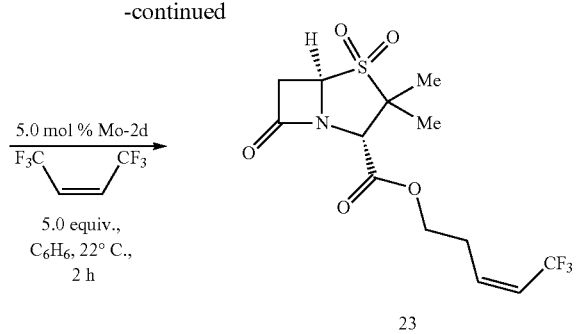
23
>98% conv., 83% yield,
>98:2 Z:E
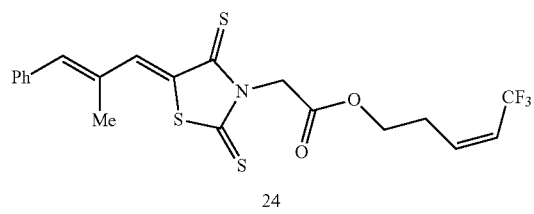
24
(derived from epalrestat,
an aldose reductase inhibitor)
>98% conv., 92% yield,
>98:2 Z:E
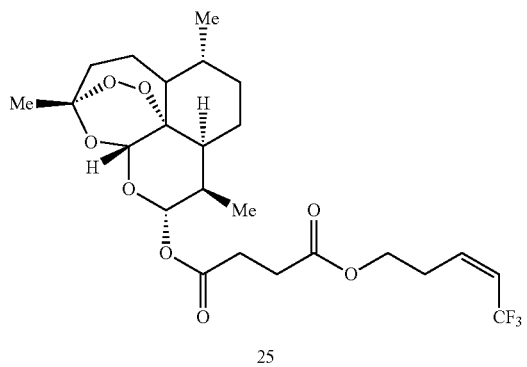
25
(derived from artesunate,
an anti-malarial agent)
86% conv., 81% yield,
>98:2 Z:E
Experimental Procedures for Preparation of Mo-Based MAX Complexes (Illustrated in Scheme 8)
Scheme 8
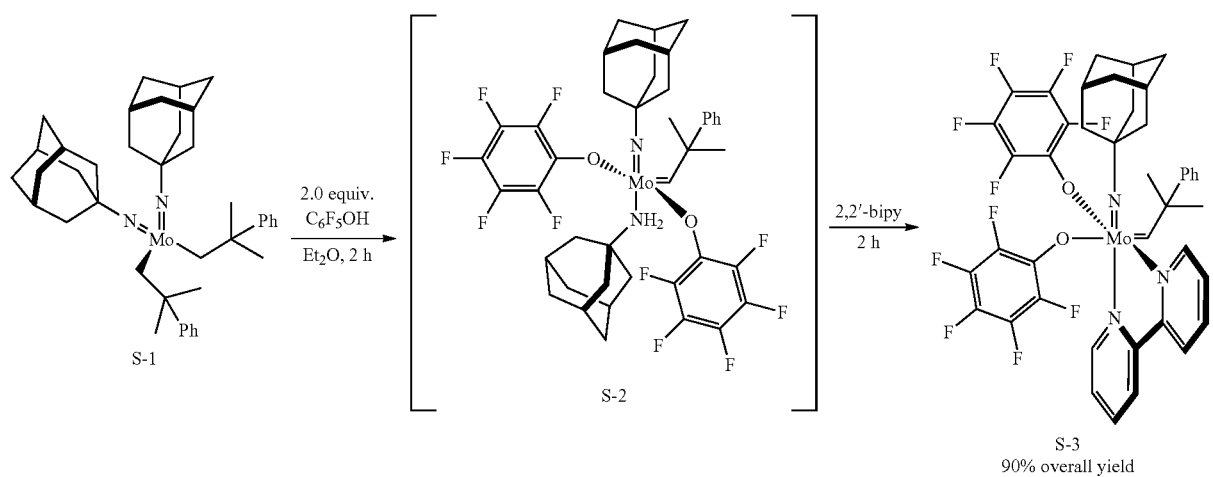

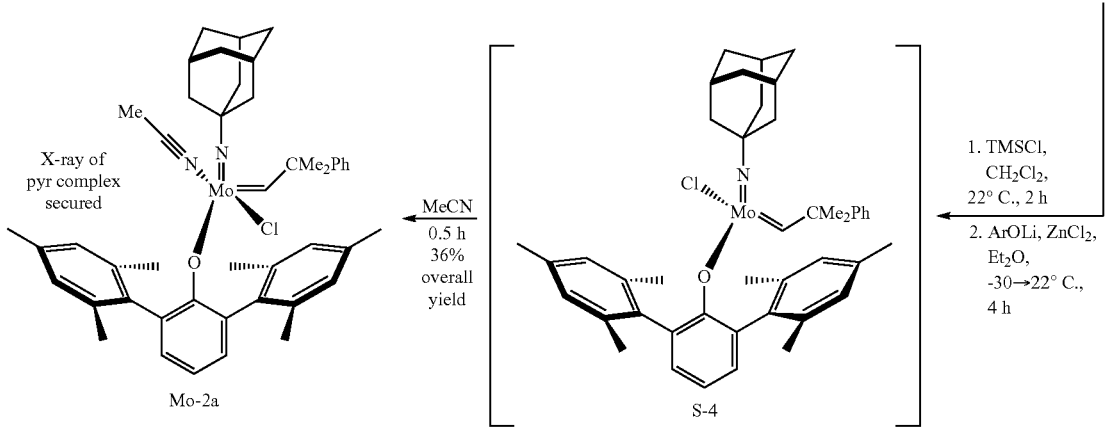

Complex S-3:

Dialkyl Mo species S-1 was prepared according to the published procedure. This compound (2.00 g, 3.02 mmol, 1.00 equiv.) was dissolved in Et$_2$O (50 mL), chilled to −25° C. and treated with a pre-cooled solution of pentafluorophenol (1.17 g, 6.34 mmol, 2.10 equiv.) in Et$_2$O (10 mL). The resulting orange solution was stirred at 22° C. for 2 h, then treated with solid bipyridine (0.48 g, 3.02 mmol, 1.00 equiv.) in one portion. The reaction was allowed to stir at 22° C. for a further 2 h, during which time a yellow precipitate formed. The mixture was then allowed to cool to −25° C. and the precipitate collected by filtration and washed with a solution of cold Et$_2$O to afford S-3 (2.44 g, 90%) as yellow solid, which was re-crystallized from a mixture of CH$_2$Cl$_2$/pentane. $^1$H NMR (500 MHz, CD$_2$Cl$_2$): δ 13.87 (s, 1H), 9.31 (d, J=5.7 Hz, 1H), 8.06 (ddd, J=10.0, 10.0, 2.1 Hz, 1H), 7.98 (dd, J=10.2, 10.2 Hz, 2H), 7.87 (ddd, J=9.7, 9.7, 2.0 Hz, 1H), 7.65 (m, 1H), 7.55-7.47 (m, 3H), 7.34 (m, 2H), 7.22 (m, 1H), 6.90 (m, 1H), 2.07 (s, 3H), 1.81 (brs, 3H), 1.57-1.33 (m, 15H); $^{13}$C NMR (100 MHz, CD$_2$Cl$_2$): (overlapping resonances split by F-coupling are omitted) δ 311.1, 158.6, 253.8, 151.6, 149.6, 140.2, 140.1, 128.7, 126.7, 126.6, 126.2, 125.4, 122.34, 121.6, 72.0, 53.8, 51.1, 42.8, 36.0, 31.4, 30.8, 29.5; $^{19}$F NMR (282 MHz, CD$_2$Cl$_2$): δ−160.1 (d, J=22 Hz), −162.6 (d, J=21 Hz), −169.5 (d, J=21 Hz), −170.1 (d, J=21 Hz), −178.1 (m), −180.2 (m).

MAX Complex Mo-2a:

Complex S-3 (415 mg, 0.461 mmol, 1.00 equiv.) was dissolved in CH$_2$Cl$_2$ (10 mL) and treated with Me$_3$SiCl (660 mg, 6.08 mmol, 13.2 equiv.). After it was allowed to stir at 22° C. for 10 h, the volatiles were removed in vacuo and the resulting solid was allowed to stir with Et$_2$O and yellow solid was collected by filtration to furnish a new complex (242 mg, 87%) as yellow solid. $^1$H NMR (500 MHz, CD$_2$Cl$_2$): δ (major isomer, 60%; selected resolved peaks only) 14.35 (s, 1H), 9.58 (d, J=5.8 Hz, 2H) 1.99 (s, 3H); $^1$H NMR (500 MHz, CD$_2$Cl$_2$): δ (minor isomer, 40%; selected resolved peaks only) 12.98 (s, 1H), 8.90 (brs, 1H), $^{13}$C NMR (100 MHz, CD$_2$Cl$_2$): δ (peaks reported for the mixture of isomers) 316.8, 313.9, 158.5, 154.4, 149.7, 140.8, 140.0 139.9, 139.6, 128.6, 128.2, 126.9, 126.6, 126.1, 125.9, 123.8, 123.0, 122.8, 75.7, 73.5, 54.2, 52.3, 52.1, 42.7, 42.2, 36.1, 35.7, 41.6, 30.6, 30.2, 29.7, 29.2. The resulting complex (250 mg, 0.538 mmol, 1.00 equiv.) was then suspended in Et$_2$O (50 mL) and cooled to −25° C. A suspension of lithium 2,6-(2,4,6-trimethylphenyl)phenoxide (HMTOLi) (196 mg, 0.522 mmol, 0.97 equiv.) in Et$_2$O (5 mL) was added slowly, followed by a solution of ZnCl$_2$ (73 mg, 0.522 mmol, 1.00 equiv.) in Et$_2$O (5 mL). After the solution was allowed to stir at 22° C. for 2 h, the mixture was filtered through Celite and concentrated to give red-brown foam. This material was washed with pentane (30 mL) and filtered through Celite to give a dark brown solution S-4 and unidentified alkylidyne by-products. Acetonitrile (2 mL) was added to this pentane solution, and the resulting pink slurry was concentrated to dryness. The residue obtained was triturated with pentane (5 mL) and cooled to −25° C. and kept at this temperature for 16 h. Solid was collected by filtration, washed with cold pentane (~1 mL) and cold acetonitrile (~1 mL) to give Mo-2a (167 mg, 41% yield) as off-white solid.

Complex S-5 (Precursor to Mo-2e, not Shown):

Mo(NC$_6$F$_5$)$_2$(CHCMe$_2$Ph)$_2$ was prepared according to the published procedure (Sues, P. E.; John, J. M.; Schrock, R. R.; Müller P. Organometallics 2016, 35, 758-761). This compound (1.00 g, 1.38 mmol, 1.00 equiv.) was dissolved in Et$_2$O (6 mL). PPhMe$_2$HCl (0.48 g, 2.76 mmol, 2.00 equiv.) was added as a solid in one portion. The resulting suspension was stirred for 1 hour at room temperature, during which time a white solid of phosphonium salt dissolved and yellow precipitate formed. Precipitate collected by filtration, washed with 4 ml of cold Et$_2$O and dried under vacuum to give complex S-5 [Mo(NC$_6$F$_5$)(CHCMe$_2$Ph)(PPhMe$_2$)$_2$Cl$_2$*Et$_2$O] (760 mg, 66%) as yellow solid. $^1$H NMR (600 MHz; C$_6$D$_6$): δ 14.32 (t, J$_{P-H}$=4.4 Hz, J$_{C-H}$=126 Hz, 1H), 7.64 (s, 4H), 7.10 (d, J=7.4 Hz, 2H), 6.95 (s, 6H), 6.90 (t, J=7.4 Hz, 3H), 6.75 (t, J=7.0 Hz, 1H), 1.92 (t, J=3.9 Hz, 6H), 1.72 (t, J=3.9 Hz, 6H), 1.11 (s, 6H). $^{13}$C NMR (151 MHz; C$_6$D$_6$): δ 334.67 (t, J$_{C-P}$=14.8 Hz, Mo=C), 148.8, 146.14, 146.09, 146.05, 144.42, 144.35, 138.00, 137.81, 137.68, 137.56, 136.4, 130.62, 130.59, 129.8, 128.40, 128.37, 128.35, 127.98, 127.5, 126.43, 126.31, 125.9, 56.5, 30.0, 28.4, 15.93, (t, J$_{C-P}$=15.0 Hz, PCH$_3$), 14.51 (t, J$_{C-P}$=14.9 Hz, PCH$_3$). $^{31}$P NMR (162 MHz; C$_6$D$_6$): δ−0.1. $^{19}$F NMR (376 MHz; C$_6$D$_6$): δ−140.5 (m), −156.3 (t, J=21.8 Hz), −163.7 (m). Anal Calcd for C$_{32}$H$_{34}$Cl$_2$F$_5$MoNP$_2$: C, 50.81; H, 4.53; N, 1.85. Found: C, 50.77; H, 4.59; N, 1.82.

MAX Complex Mo-2e:

Complex S-5 (640 mg, 0.771 mmol, 1.00 equiv.) was suspended in Et$_2$O (15 mL) and chilled to −25° C. Cold solution (−25° C.) of lithium 2,6-(2,4,6-triisopropylphenyl) phenoxide (HIPTOLi) (339 mg, 0.771 mmol, 1.00 equiv.) in 5 ml of Et$_2$O was added slowly and the resulting suspension was stirred for 16 hours at room temperature. The reaction mixture was filtered through Celite and volatiles were evaporated in vacuum. The residue was dissolved in 20 ml of pentane and filtered through Celite. The resulting brown solution was stirred at room temperature for 1 hour. During this time yellow precipitate formed. Precipitate collected by filtration, washed with 4 ml of cold pentane and dried under vacuum to give Mo-2e (540 mg, 65%) as yellow solid. $^1$H NMR (500 MHz; C$_6$D$_6$): δ 12.95 (d, $J_{P-H}$=3.1 Hz, $J_{C-H}$=126 Hz, 1H), 7.61-7.55 (m, 2H), 7.39-7.29 (m, 3H), 7.19-6.74 (m, 12H), 4.01-3.94 (m, 2H), 3.54-3.51 (m, 1H), 2.90-2.83 (m, 3H), 1.62-1.07 (m, 45H), 0.62 (d, J=9.0 Hz, 3H). Two isomers were observed in $^{13}$C, $^{31}$P and $^{19}$F NMR spectra. $^{13}$C NMR (151 MHz; C$_6$D$_6$): δ 328.5, 308.8, 163.2, 150.1, 149.42, 149.23, 148.25, 148.22, 148.17, 147.43, 147.35, 147.28, 146.9, 144.28, 144.23, 144.17, 142.62, 142.58, 142.54, 142.51, 140.3, 138.6, 137.8, 137.2, 136.95, 136.93, 135.9, 135.53, 135.41, 135.27, 135.0, 134.7, 133.6, 132.10, 131.98, 131.68, 131.61, 131.54, 131.11, 131.02, 130.94, 130.6, 130.2, 128.64, 128.58, 128.46, 128.44, 128.41, 128.35, 128.30, 128.14, 127.98, 127.0, 126.66, 126.53, 126.35, 123.6, 122.1, 121.4, 120.8, 120.0, 119.7, 59.4, 53.2, 34.87, 34.83, 34.60, 32.1, 31.2, 30.85, 30.80, 30.70, 27.7, 27.4, 26.7, 26.3, 25.6, 25.3, 24.70, 24.54, 24.39, 24.30, 23.8, 23.3, 22.9, 16.45, 16.36, 16.27, 15.17, 15.08, 14.99, 13.52, 13.35, 12.40, 12.38, 12.26. $^{31}$P NMR (162 MHz; C$_6$D$_6$): δ 8.0, 6.4. $^{19}$F NMR (376 MHz; C$_6$D$_6$): δ −144.1 (d, J=18.8 Hz), −150.0 (dd, J=18.6, 4.7 Hz), −157.0 (t, J=21.7 Hz), −162.9 (m), −166.3 (m), −167.6 (m). Anal Calcd for C$_{60}$H$_{72}$ClF$_5$MoNOP: C, 66.69; H, 6.72; N, 1.30. Found: C, 64.00; H, 6.18; N, 1.35.

Experimental Procedure for Z-Selective Cross-Metathesis of Z-1,2-Disubstituted Alkenes with Mo-2a-2d General Procedure:

In a N$_2$-filled glove box, an oven-dried 8 mL vial equipped with a magnetic stir bar was charged with alkene substrate (1.0 equiv) and Z-1,1,1,4,4,4-hexafluoro-2-butene (5.0 equiv). To this vessel, a solution of Mo-2a, Mo-2b, Mo-2c or Mo-2d in benzene (2-5 mol %) was added. The resulting mixture was allowed to stir for 15 min-12 h at 22° C., after which the reaction was quenched by the addition of wet CDCl$_3$; percent conversion was determined by 400 MHz $^1$H NMR analysis of the unpurified mixture). Purification was performed through silica gel chromatography, preparative thin layer chromatography and/or Kugelrohr distillation.

(Z)-1-(2-Chlorovinyl)-4-methoxybenzene (1)

Following the general procedure, a solution of Mo-2b in benzene (0.1 M, 50 μL, 5.0 μmol, 5 mol %) was transferred by syringe to an oven-dried vial containing Z-1,2-dichloroethene (96.9 mg, 1.00 mmol, 10.0 equiv) and Z-1-methoxy-4-(prop-1-enyl)benzene (14.8 mg, 0.100 mmol, 1.0 equiv). The resulting solution was allowed to stir for 4 h at 22° C. The reaction was quenched by addition of wet CDCl$_3$ and analysis of the unpurified mixture revealed >98% consumption of Z-1-methoxy-4-(prop-1-enyl)benzene. The resulting green oil was purified by silica gel chromatography (2% Et$_2$O/hexane) to afford 1 (13.5 mg, 0.0801 mmol, 80% yield) in >98:<2 Z:E ratio as colorless oil. The spectral data for this compound were identical to those reported previously (Lebrun, M.-V.; Marquand, P. L.; Berthelette, C. *J. Org. Chem.* 2006, 71, 2009-2013).

(Z)-tert-Butyl 5-(2-chlorovinyl)-1H-indole-1-carboxylate (2)

Following the general procedure, a solution of Mo-2b in benzene (0.1 M, 25 μL, 2.5 μmol, 5 mol %) was transferred by syringe to an oven-dried vial containing Z-1,2-dichloroethene (48.5 mg, 0.500 mmol, 10.0 equiv) and (Z)-tert-butyl 5-(prop-1-enyl)-1H-indole-1-carboxylate (12.9 mg, 0.0500 mmol, 1.0 equiv). The resulting solution was allowed to stir for 2 h at 22° C. The reaction was quenched by addition of wet CDCl$_3$ and analysis of the unpurified mixture revealed >98% consumption of (Z)-tert-butyl 5-(prop-1-enyl)-1H-indole-1-carboxylate. The resulting green oil was purified by silica gel chromatography (1% EtOAc/hexane to 2% EtOAc/hexane) to afford 2 (11.5 mg, 0.0414 mmol, 83% yield) in >98:<2 Z:E ratio as pale yellow oil. $^1$H NMR (400 MHz, CDCl$_3$): Z-isomer (major): δ 8.11 (1H, d, J=8.6 Hz), 7.95 (1H, s), 7.62 (2H, m), 6.73 (1H, d, J=8.2 Hz), 6.58 (1H, d, J=3.7 Hz), 6.24 (1H, d, J=8.1 Hz), 1.68 (9H, s).

(1E,3Z)-4-Chlorobuta-1,3-dienyl)benzene (3)

Following the general procedure, a solution of Mo-2b in benzene (0.1 M, 50 μL, 5.0 μmol, 5 mol %) was transferred by syringe to an oven-dried vial containing Z-1,2-dichloroethene (96.9 mg, 1.00 mmol, 10.0 equiv) and (1E,3Z)-penta-1,3-dienylbenzene (14.4 mg, 0.100 mmol, 1.0 equiv). The resulting solution was allowed to stir for 4 h at 22° C. The reaction was quenched by addition of wet CDCl$_3$ and analysis of the unpurified mixture revealed >98% consumption of (1E,3Z)-penta-1,3-dienylbenzene. The resulting green oil was purified by silica gel chromatography (100% hexane) to afford 3 (13.7 mg, 0.0832 mmol, 83% yield) in >98:<2 Z:E ratio as colorless oil. The spectral data for this compound were identical to those reported previously (Sues, P. E.; John, J. M.; Schrock, R. R.; Müller P. *Organometallics* 2016, 35, 758-761).

(Z)-2-(3-Chloroallyl)-4,4,5,5-tetramethyl-1,3,2-dioxaborolane (4)

Following the general procedure, a solution of Mo-2a in benzene (0.1 M, 150 μL, 15.0 μmol, 3 mol %) was transferred by syringe to an oven-dried vial containing Z-1,2-dichloroethene (242 mg, 2.50 mmol, 5.0 equiv) and Z-crotylboronic acid pinacol ester (91 mg, 0.500 mmol, 1.0 equiv). The resulting solution was allowed to stir for 2 h at 22° C. The reaction was quenched by addition of wet CDCl$_3$ and analysis of the unpurified mixture revealed >98% consumption of Z-crotylboronic acid pinacol ester. The resulting green oil was purified by Kugelrohr distillation (50° C., 1 torr, 1 hour) to afford 4 (89 mg, 0.440 mmol, 88% yield) in >98:2 Z:E ratio as colorless oil. The spectral data for this compound are identical to those reported previously (Koh, M. J.; Nguyen, T. T.; Zhang, H.; Schrock, R. R.; Hoveyda, A. H. *Nature* 2016, 531, 459-465).

(Z)-Methyl 10-bromodec-9-enoate (5) & (Z)-1-bromodec-1-ene (6)

Following the general procedure, a solution of Mo-2b in benzene (0.1 M, 12 μL, 1.2 μmol, 3 mol %) was transferred by syringe to an oven-dried vial containing 1,2-dibromoethene (59.5 mg, 0.320 mmol, 8.0 equiv) and Z-methyl oleate (11.9 mg, 0.0400 mmol, 1.0 equiv). The resulting solution was allowed to stir for 2 h at 22° C. The reaction was quenched by addition of wet CDCl$_3$ and analysis of the unpurified mixture revealed 95% consumption of Z-methyl oleate. The resulting green oil was purified by silica gel chromatography (100% hexane to 4% Et$_2$O/hexane) to afford 5 (10.0 mg, 0.0380 mmol, 95% yield) in >98:<2 Z:E ratio as colorless oil and 6 (7.5 mg, 0.0342 mmol, 85% yield) in >98:2 Z:E ratio as colorless oil. Spectral data for 5: $^1$H NMR (500 MHz, CDCl$_3$): Z isomer (major): δ 6.14 (1H, d, J=6.9 Hz), 6.08 (1H, q, J=6.9 Hz), 3.67 (3H, s), 2.30 (2H, t, J=7.5 Hz), 2.18 (2H, dt, J=7.6, 4.0 Hz), 1.61 (2H, dd, J=14.2, 7.1 Hz), 1.43 (2H, m), 1.32 (6H, brs). The spectral data for 6 were identical to those reported previously (Millar, J. G.; Underhill, E. W. *J. Org. Chem.* 1986, 51, 4726-4728).

(1Z,9Z)-1,10-Dibromodeca-1,9-diene (7)

In a N$_2$-filled glove box, a solution of Mo-2a in benzene (0.1 M, 100 μL, 10.0 μmol, 10 mol %) was transferred by syringe to an oven-dried vial containing 1,2-dibromoethene (148.7 mg, 0.800 mmol, 8.0 equiv) and Z-cyclooctene (11.0 mg, 0.100 mmol, 1.0 equiv.). The resulting solution was allowed to stir for 2 h at 22° C. The reaction was quenched by addition of wet CDCl$_3$ and analysis of the unpurified mixture revealed >98% consumption of Z-cyclooctene. The resulting green oil was purified by silica gel chromatography (100% hexanes) to afford 1 (25.2 mg, 0.0851 mmol, 85% yield) in >98:2 Z:E ratio as colorless oil. The spectral data for this compound were identical to those reported previously (Koh, M. J.; Nguyen, T. T.; Zhang, H.; Schrock, R. R.; Hoveyda, A. H. *Nature* 2016, 531, 459-465).

(Z)-Methyl 11,11,11-trifluoro-9-undecenoate (9) & (Z)-1,1,1-trifluoro-2-undecene (10)

Following the general procedure, a solution of Mo-2d in benzene (0.1 M, 8 μL, 0.8 μmol, 2 mol %) was transferred by syringe to an oven-dried vial containing Z-1,1,1,4,4,4-hexafluoro-2-butene (32.8 mg, 0.200 mmol, 5.0 equiv) and Z-methyl oleate (11.9 mg, 0.0400 mmol, 1.0 equiv). The resulting solution was allowed to stir for 15 min at 22° C. The reaction was quenched by addition of wet CDCl$_3$ and analysis of the unpurified mixture revealed >98% consumption of Z-methyl oleate. The resulting green oil was purified by silica gel chromatography (100% pentane to 4% Et$_2$O/pentane) to afford 9 (9.6 mg, 0.0381 mmol, 95% yield) in >98:<2 Z:E ratio as colorless oil and 10 (5.6 mg, 0.0269 mmol, 67% yield) in >98:2 Z:E ratio as colorless oil. Spectral data for 9: $^1$H NMR (400 MHz, CDCl$_3$): Z isomer (major): δ 5.97 (1H, dt, J=11.5, 7.9 Hz), 5.64 (1H, m), 3.67 (3H, s), 2.33 (4H, m), 1.67 (2H, m), 1.45-1.37 (2H, m), 1.34-1.29 (6H, m). Spectral data for 10: $^1$H NMR (400 MHz, CDCl$_3$): Z isomer (major): δ 5.98 (1H, dt, J=11.6, 7.9 Hz), 5.64 (1H, m), 2.35 (2H, m), 1.47 (2H, m), 1.33-1.23 (10H, m), 0.88 (3H, t, J=6.9 Hz).

(Z)-1-Methoxy-4-((4,4,4-trifluorobut-2-enyloxy)methyl)benzene (11a)

Following the general procedure, a solution of Mo-2d in benzene (0.1 M, 25 μL, 2.5 μmol, 5 mol %) was transferred by syringe to an oven-dried vial containing Z-1,1,1,4,4,4-hexafluoro-2-butene (41.0 mg, 0.250 mmol, 5.0 equiv) and (Z)-1-methoxy-4-((pent-2-enyloxy)methyl)benzene (10.3 mg, 0.0499 mmol, 1.0 equiv). The resulting solution was allowed to stir for 4 h at 22° C. The reaction was quenched by addition of wet CDCl$_3$ and analysis of the unpurified mixture revealed 87% consumption of (Z)-1-methoxy-4-((pent-2-enyloxy)methyl)benzene. The resulting green oil was purified by silica gel chromatography (5% Et$_2$O/pentane to 10% Et$_2$O/pentane) to afford 11a (9.5 mg, 0.0386 mmol, 77% yield) in >98:2 Z:E ratio as colorless oil. $^1$H NMR (400 MHz, CDCl$_3$): Z isomer (major): δ 7.27 (2H, d, J=8.6 Hz), 6.89 (2H, d, J=8.6 Hz), 6.17 (1H, dt, J=11.8, 5.7 Hz), 5.75 (1H, m), 4.46 (2H, s), 4.29 (2H, td, J=5.2, 2.5 Hz), 3.81 (3H, s).

(Z)-5,5,5-Trifluoro-3-pentenyl 4-methylbenzenesulfonate (11b)

Following the general procedure, a solution of Mo-2d in benzene (0.1 M, 8 μL, 0.8 μmol, 2 mol %) was transferred by syringe to an oven-dried vial containing Z-1,1,1,4,4,4-hexafluoro-2-butene (32.9 mg, 0.201 mmol, 5.0 equiv) and (Z)-3-hexenyl 4-methylbenzenesulfonate (10.2 mg, 0.0401 mmol, 1.0 equiv). The resulting solution was allowed to stir for 2 h at 22° C. The reaction was quenched by addition of wet CDCl$_3$ and analysis of the unpurified mixture revealed 82% consumption of (Z)-3-hexenyl 4-methylbenzenesulfonate. The resulting green oil was purified by silica gel chromatography (5% Et$_2$O/hexane) to afford 11b (9.1 mg, 0.0309 mmol, 77% yield) in >98:2 Z:E ratio as colorless oil. $^1$H NMR (400 MHz, CDCl$_3$): Z isomer (major): δ 7.79 (2H, d, J=8.3 Hz), 7.36 (2H, d, J=8.5 Hz), 5.96 (1H, dt, J=11.7, 7.5 Hz), 5.75 (1H, m), 4.10 (2H, t, J=6.3 Hz), 2.69 (2H, m), 2.46 (3H, s).

(Z)-2,2-Dimethyl-7-(6,6,6-trifluorohex-4-enyloxy)-2,3-dihydrobenzofuran (11c)

Following the general procedure, a solution of Mo-2d in benzene (0.1 M, 15 μL, 1.5 μmol, 3 mol %) was transferred by syringe to an oven-dried vial containing Z-1,1,1,4,4,4-hexafluoro-2-butene (41.0 mg, 0.250 mmol, 5.0 equiv) and (Z)-7-(hex-4-enyloxy)-2,2-dimethyl-2,3-dihydrobenzofuran (12.3 mg, 0.0499 mmol, 1.0 equiv). The resulting solution was allowed to stir for 2 h at 22° C. The reaction was quenched by addition of wet CDCl$_3$ and analysis of the unpurified mixture revealed >98% consumption of (Z)-7-(hex-4-enyloxy)-2,2-dimethyl-2,3-dihydrobenzofuran. The resulting green oil was purified by silica gel chromatography (2% Et$_2$O/hexane) to afford 11c (12.9 mg, 0.0430 mmol, 86% yield) in >98:2 Z:E ratio as colorless oil. $^1$H NMR (400 MHz, CDCl$_3$): δ 6.82-6.69 (3H, m), 6.05 (1H, dtd, J=11.6, 7.9, 0.9 Hz), 5.62 (1H, dddd, J=11.6, 10.2, 8.5, 7.1 Hz), 4.12-4.03 (2H, m), 3.06-2.98 (2H, m), 2.54-2.43 (2H, m), 2.00-1.87 (2H, m), 1.50 (6H, s).

(Z)-5,5,5-Trifluoro-3-pentenyl 2-(benzyloxy)propanoate (11d)

Following the general procedure, a solution of Mo-2d in benzene (0.1 M, 8 μL, 0.8 μmol, 2 mol %) was transferred by syringe to an oven-dried vial containing Z-1,1,1,4,4,4-hexafluoro-2-butene (32.8 mg, 0.200 mmol, 5.0 equiv) and (Z)-3-hexenyl 2-(benzyloxy)propanoate (10.5 mg, 0.0400 mmol, 1.0 equiv). The resulting solution was allowed to stir for 2 h at 22° C. The reaction was quenched by addition of wet CDCl$_3$ and analysis of the unpurified mixture revealed 73% consumption of (Z)-3-hexenyl 2-(benzyloxy)propanoate. The resulting green oil was purified by silica gel chromatography (4% Et$_2$O/pentane to 12% Et$_2$O/pentane) to afford 11d (8.5 mg, 0.0281 mmol, 70% yield) in >98:2 Z:E ratio as colorless oil. $^1$H NMR (400 MHz, CDCl$_3$): Z isomer (major): δ 7.39 (5H, m), 6.01 (1H, dt, J=11.6, 7.7 Hz), 5.79 (1H, m), 4.69 (1H, d, J=11.6 Hz), 4.45 (1H, d, J=11.7 Hz), 4.31 (2H, m), 4.06 (1H, q, J=6.9 Hz), 2.74 (2H, m), 1.43 (3H, d, J=6.9 Hz).

(Z)-tert-Butyl 3-(2-oxo-2-(5,5,5-trifluoro-3-pentenyloxy)ethyl)-1H-indole-1-carboxylate (11e)

Following the general procedure, a solution of Mo-2d in benzene (0.1 M, 9 µL, 0.9 µmol, 3 mol %) was transferred by syringe to an oven-dried vial containing Z-1,1,1,4,4,4-hexafluoro-2-butene (24.6 mg, 0.150 mmol, 5.0 equiv) and (Z)-tert-butyl 3-(2-(3-hexenyloxy)-2-oxoethyl)-1H-indole-1-carboxylate (10.7 mg, 0.0299 mmol, 1.0 equiv). The resulting solution was allowed to stir for 2 h at 22° C. The reaction was quenched by addition of wet $CDCl_3$ and analysis of the unpurified mixture revealed >98% consumption of (Z)-tert-butyl 3-(2-(3-hexenyloxy)-2-oxoethyl)-1H-indole-1-carboxylate. The resulting green oil was purified by silica gel chromatography (10% $Et_2O$/hexane to 15% $Et_2O$/hexane) to afford 11e (10.5 mg, 0.0264 mmol, 88% yield) in >98:<2 Z:E ratio as colorless oil. $^1$H NMR (400 MHz, $CDCl_3$): Z isomer (major): δ 8.14 (1H, d, J=7.1 Hz), 7.56 (1H, s), 7.52 (1H, J=7.8 Hz), 7.33 (1H, ddd, J=8.4, 7.3, 1.3 Hz), 7.27-7.23 (1H, m), 5.93 (1H, dt, J=11.7, 7.7 Hz), 5.71-5.59 (1H, m), 4.21 (2H, t, J=6.3 Hz), 3.72 (2H, d, J=1.0 Hz), 2.69-2.60 (2H, m), 1.67 (9H, s).

(S,Z)-1-tert-Butyl 2-(5,5,5-trifluoropent-3-enyl) pyrrolidine-1,2-dicarboxylate (11f)

Following the general procedure, a solution of Mo-2d in benzene (0.1 M, 9 µL, 0.9 µmol, 3 mol %) was transferred by syringe to an oven-dried vial containing Z-1,1,1,4,4,4-hexafluoro-2-butene (24.6 mg, 0.150 mmol, 5.0 equiv) and (S,Z)-1-tert-butyl 2-hex-3-enyl pyrrolidine-1,2-dicarboxylate (8.9 mg, 0.0299 mmol, 1.0 equiv). The resulting solution was allowed to stir for 2 h at 22° C. The reaction was quenched by addition of wet $CDCl_3$ and analysis of the unpurified mixture revealed >98% consumption of (S,Z)-1-tert-butyl 2-hex-3-enyl pyrrolidine-1,2-dicarboxylate. The resulting green oil was purified by silica gel chromatography (4% $Et_2O$/pentane to 20% $Et_2O$/pentane) to afford 11f (8.1 mg, 0.0240 mmol, 80% yield) in >98:<2 Z:E ratio as colorless oil. $^1$H NMR (400 MHz, $CDCl_3$): Z isomer (major): δ 6.02 (1H, ddd, J=17.3, 13.9, 7.5 Hz), 5.79-5.64 (1H, m), 4.34-4.13 (3H, m), 3.59-3.33 (2H, m), 2.67 (2H, brs), 2.27-2.14 (1H, m), 2.01-1.81 (3H, m), 1.46 (3H, s), 1.41 (6H, s).

(Z)-Triisopropyl(3-(5,5,5-trifluoropent-3-enyloxy)prop-1-ynyl)silane (11g)

Following the general procedure, a solution of Mo-2d in benzene (0.1 M, 20 µL, 2.0 µmol, 5 mol %) was transferred by syringe to an oven-dried vial containing Z-1,1,1,4,4,4-hexafluoro-2-butene (32.9 mg, 0.200 mmol, 5.0 equiv) and (Z)-(3-(hex-3-enyloxy)prop-1-ynyl)triisopropylsilane (11.8 mg, 0.0401 mmol, 1.0 equiv). The resulting solution was allowed to stir for 2 h at 22° C. The reaction was quenched by addition of wet $CDCl_3$ and analysis of the unpurified mixture revealed >98% consumption of (Z)-(3-(hex-3-enyloxy)prop-1-ynyl)triisopropylsilane. The resulting green oil was purified by silica gel chromatography (1% $Et_2O$/hexane to 2% $Et_2O$/hexane) to afford 11g (11.0 mg, 0.0329 mmol, 82% yield) in >98:2 Z:E ratio as colorless oil. $^1$H NMR (400 MHz, $CDCl_3$): Z isomer (major): δ 6.10 (1H, dt, J=11.5, 7.4 Hz), 5.72 (1H, m), 4.19 (2H, d, J=0.6 Hz), 3.64 (2H, t, J=6.3 Hz), 2.64 (2H, m), 1.07 (21H, brs).

(R,Z)-tert-Butyldiphenyl(5,5,5-trifluoro-2-methylpent-3-enyloxy)silane (11h)

Following the general procedure, a solution of Mo-2d in benzene (0.1 M, 20 µL, 2.0 µmol, 5 mol %) was transferred by syringe to an oven-dried vial containing Z-1,1,1,4,4,4-hexafluoro-2-butene (65.4 mg, 0.399 mmol, 10.0 equiv) and (R,Z)-tert-butyl(2-methylpent-3-enyloxy)diphenylsilane (13.5 mg, 0.0399 mmol, 1.0 equiv). The resulting solution was allowed to stir for 4 h at 22° C. The reaction was quenched by addition of wet $CDCl_3$ and analysis of the unpurified mixture revealed >98% consumption of (R,Z)-tert-butyl(2-methylpent-3-enyloxy)diphenylsilane. The resulting green oil was purified by preparative thin layer chromatography (100% hexane) to afford 11h (13.3 mg, 0.0339 mmol, 85% yield) in >98:<2 Z:E ratio as colorless oil. $^1$H NMR (400 MHz, $CDCl_3$): Z isomer (major): δ 7.68-7.62 (4H, m), 7.46-7.35 (6H, m), 5.98 (1H, dd, J=11.6, 10.9 Hz), 5.60 (1H, dq, J=11.6, 8.8 Hz), 3.61-3.50 (2H, m), 3.06-2.95 (1H, m), 1.05 (12H, brs).

(Z)-2-(5,5,5-Trifluoro-3-pentenyl)isoindoline-1,3-dione (11h)

Following the general procedure, a solution of Mo-2d in benzene (0.1 M, 12 µL, 1.2 µmol, 3 mol %) was transferred by syringe to an oven-dried vial containing Z-1,1,1,4,4,4-hexafluoro-2-butene (32.9 mg, 0.201 mmol, 5.0 equiv), (Z)-2-(3-hexenyl)isoindoline-1,3-dione (9.2 mg, 0.0401 mmol, 1.0 equiv) and toluene (80 µL). The resulting solution was allowed to stir for 4 h at 22° C. The reaction was quenched by addition of wet $CDCl_3$ and analysis of the unpurified mixture revealed >98% consumption of (Z)-2-(3-hexenyl)isoindoline-1,3-dione. The resulting green oil was purified by silica gel chromatography (5% EtOAc/hexane) to afford 11i (8.4 mg, 0.0312 mmol, 78% yield) in >98:2 Z:E ratio as colorless oil. The spectral data for this compound were identical to those reported previously (Mizuta, S.; Verhoog, S.; Engle, K. M.; Khotavivattana, T.; O'Duill, M.; Wheelhouse, K.; Rassias, G.; Médebielle, M.; Gouverneur, V. *J. Am. Chem. Soc.* 2013, 135, 2505-2508).

(Z)—N,N-Dibenzyl-5,5,5-trifluoropent-3-en-1-amine (11j)

Following the general procedure, a solution of Mo-2d in benzene (0.1 M, 12 µL, 1.2 µmol, 3 mol %) was transferred by syringe to an oven-dried vial containing Z-1,1,1,4,4,4-hexafluoro-2-butene (32.9 mg, 0.200 mmol, 5.0 equiv) and (Z)—N,N-dibenzylhex-3-en-1-amine (11.2 mg, 0.0401 mmol, 1.00 equiv). The resulting solution was allowed to stir for 2 h at 22° C. The reaction was quenched by addition of wet $CDCl_3$ and analysis of the unpurified mixture revealed >98% consumption of (Z)—N,N-dibenzylhex-3-en-1-amine. The resulting green oil was purified by silica gel chromatography (5% EtOAc/hexane) to afford 11j (11.8 mg, 0.0369 mmol, 92% yield) in >98:2 Z:E ratio as colorless oil. $^1$H NMR (400 MHz, $CDCl_3$): δ 7.44-7.17 (10H, m), 5.96 (1H, dt, J=12.8, 6.4 Hz), 5.67-5.53 (1H, m), 3.57 (4H, s), 2.62-2.43 (4H, m).

(Z)-6,6,6-Trifluoro-4-hexenyl ferrocenecarboxylate (11k)

Following the general procedure, a solution of Mo-2d in benzene (0.1 M, 12 µL, 1.2 µmol, 3 mol %) was transferred by syringe to an oven-dried vial containing Z-1,1,1,4,4,4-hexafluoro-2-butene (32.8 mg, 0.200 mmol, 5.0 equiv) and (Z)-4-hexenyl ferrocenecarboxylate (12.5 mg, 0.0400 mmol, 1.0 equiv). The resulting solution was allowed to stir for 2 h at 22° C. The reaction was quenched by addition of wet $CDCl_3$ and analysis of the unpurified mixture revealed >98% consumption of (Z)-4-hexenyl ferrocenecarboxylate. The resulting reddish-brown oil was purified by silica gel chromatography (2% EtOAc/hexane to 5% EtOAc/hexane) to afford 11k (14.4 mg, 0.0393 mmol, 98% yield) in >98:2 Z:E ratio as red oil. $^1$H NMR (400 MHz, CDCl$_3$): Z isomer (major): δ 6.06 (1H, dt, J=11.5, 7.9 Hz), 5.74 (1H, m), 4.84 (2H, m), 4.43 (2H, m), 4.24 (2H, t, J=6.4 Hz), 4.22 (5H, m), 2.54 (2H, m), 1.93 (2H, m).

(Z)-tert-Butyl 4-(3,3,3-trifluoroprop-1-enyl)piperidine-1-carboxylate (11l)

Following the general procedure, a solution of Mo-2d in benzene (0.1 M, 20 μL, 2.0 μmol, 5 mol %) was transferred by syringe to an oven-dried vial containing Z-1,1,1,4,4,4-hexafluoro-2-butene (65.5 mg, 0.399 mmol, 10.0 equiv) and (Z)-tert-butyl 4-(prop-1-enyl)piperidine-1-carboxylate (9.0 mg, 0.0399 mmol, 1.0 equiv). The resulting solution was allowed to stir for 2 h at 22° C. The reaction was quenched by addition of wet CDCl$_3$ and analysis of the unpurified mixture revealed >98% consumption of (Z)-tert-butyl 4-(prop-1-enyl)piperidine-1-carboxylate. The resulting green oil was purified by silica gel chromatography (1.5% Et$_2$O/hexane) to afford 11l (9.8 mg, 0.0351 mmol, 88% yield) in >98:2 Z:E ratio as colorless oil. $^1$H NMR (400 MHz, CDCl$_3$): Z isomer (major): δ 5.78 (1H, dd, J=11.5, 10.5 Hz), 5.62 (1H, m), 4.21 (2H, m), 2.82 (3H, m), 1.68 (2H, m), 1.46 (9H, s), 1.35 (2H, m).

(Z)-Phenyl(5,5,5-trifluoropent-3-enyl)sulfane (11m)

Following the general procedure, a solution of Mo-2d in benzene (0.1 M, 18 μL, 1.9 μmol, 3 mol %) was transferred by syringe to an oven-dried vial containing Z-1,1,1,4,4,4-hexafluoro-2-butene (49.0 mg, 0.299 mmol, 5.0 equiv) and (Z)-hex-3-enyl(phenyl)sulfane (11.5 mg, 0.0598 mmol, 1.0 equiv). The resulting solution was allowed to stir for 2 h at 22° C. The reaction was quenched by addition of wet CDCl$_3$ and analysis of the unpurified mixture revealed >98% consumption of (Z)-hex-3-enyl(phenyl)sulfane. The resulting green oil was purified by silica gel chromatography (100% pentane to 2% Et$_2$O/pentane) to afford 11m (9.6 mg, 0.0413 mmol, 69% yield) in 95:5 Z:E ratio as colorless oil. $^1$H NMR (400 MHz, CDCl$_3$): Z isomer (major): δ 7.36 (2H, d, J=7.9 Hz), 7.30 (2H, t, J=7.6 Hz), 7.36 (1H, t, J=7.2 Hz), 6.09 (1H, dt, J=11.7, 7.6 Hz), 5.72-5.59 (1H, m), 3.00 (2H, t, J=7.2 Hz), 2.67-2.58 (2H, m).

((1E,4Z)-6,6,6-Trifluoro-1,4-hexadienyl)benzene (11n)

Following the general procedure, a solution of Mo-2d in benzene (0.1 M, 19 μL, 1.9 μmol, 3 mol %) was transferred by syringe to an oven-dried vial containing Z-1,1,1,4,4,4-hexafluoro-2-butene (51.8 mg, 0.316 mmol, 5.0 equiv) and (1E,4Z)-1,4-hexadienylbenzene (10.0 mg, 0.0632 mmol, 1.0 equiv). The resulting solution was allowed to stir for 2 h at 22° C. The reaction was quenched by addition of wet CDCl$_3$ and analysis of the unpurified mixture revealed 92% consumption of (1E,4Z)-1,4-hexadienylbenzene. The resulting green oil was purified by silica gel chromatography (100% pentane) to afford 11n (8.3 mg, 0.0391 mmol, 62% yield) in 97:3 Z:E ratio as colorless oil. $^1$H NMR (400 MHz, CDCl$_3$): Z isomer (major): δ 7.37 (4H, m), 7.25 (1H, m), 6.45 (1H, d, J=15.8 Hz), 6.16 (1H, dt, J=15.7, 6.7 Hz), 6.08 (1H, dt, J=11.6, 7.9 Hz), 5.76 (1H, m), 3.26 (2H, m).

(Z)-4,4,5,5-Tetramethyl-2-(4,4,4-trifluoro-2-butenyl)-1,3,2-dioxaborolane (11o)

Following the general procedure, a solution of Mo-2d in benzene (0.1 M, 50 μL, 5.0 μmol, 5 mol %) was transferred by syringe to an oven-dried vial containing Z-1,1,1,4,4,4-hexafluoro-2-butene (82.0 mg, 0.500 mmol, 5.0 equiv) and Z-crotylboronic acid pinacol ester (18.2 mg, 0.100 mmol, 1.0 equiv). The resulting solution was allowed to stir for 2 h at 22° C. The reaction was quenched by addition of wet CDCl$_3$ and analysis of the unpurified mixture revealed >98% consumption of Z-crotylboronic acid pinacol ester. The resulting green oil was purified by Kugelrohr distillation (50° C., 1 torr, 15 minutes) to afford 11o (16.6 mg, 0.0703 mmol, 70% yield) in 97:3 Z:E ratio as colorless oil. $^1$H NMR (400 MHz, CDCl$_3$): Z isomer (major): δ 6.16 (1H, dt, J=11.5, 8.9 Hz), 5.63-5.50 (1H, m), 1.98 (2H, d, J=8.2 Hz), 1.25 (12H, s).

(Z)-Triethyl(4,4,4-trifluorobut-2-en-1-yl)silane (11p)

Following the general procedure, a solution of Mo-2d in benzene (0.1 M, 15 μL, 1.5 μmol, 3 mol %) was transferred by syringe to an oven-dried vial containing Z-1,1,1,4,4,4-hexafluoro-2-butene (40.5 mg, 0.250 mmol, 5.0 equiv) and (Z)-but-2-en-1-yltriethylsilane (8.5 mg, 0.0500 mmol, 1.0 equiv). The resulting solution was allowed to stir for 4 h at 22° C. The reaction was quenched by addition of wet CDCl$_3$ and analysis of the unpurified mixture revealed >98% consumption of (Z)-but-2-en-1-yltriethylsilane. The resulting green oil was purified by silica gel chromatography (100% pentane) to afford an inseparable mixture of 11p and (Z)-1,4-bis(triethylsilyl)but-2-ene (8.6 mg, 82% wt, 0.0314 mmol, 62% yield) in 94:6 Z:E ratio as colorless oil. $^1$H NMR (400 MHz, CDCl$_3$): δ 6.04 (1H, dt, J=11.6, 9.6 Hz), 5.49-5.35 (1H, m), 1.90-1.81 (2H, m), 1.00-0.89 (9H, m), 0.59 (6H, t, J=8.0 Hz).

(Z)-1-Methoxy-4-(3,3,3-trifluoroprop-1-enyl)benzene (11q)

Following the general procedure, a solution of Mo-2d in benzene (0.1 M, 25 μL, 2.5 μmol, 5 mol %) was transferred by syringe to an oven-dried vial containing Z-1,1,1,4,4,4-hexafluoro-2-butene (81.9 mg, 0.499 mmol, 10.0 equiv) and (Z)-1-methoxy-4-(3-methylbut-1-enyl)benzene (8.8 mg, 0.0499 mmol, 1.0 equiv). The resulting solution was allowed to stir for 12 h at 22° C. The reaction was quenched by addition of wet CDCl$_3$ and analysis of the unpurified mixture revealed 89% consumption of (Z)-1-methoxy-4-(3-methylbut-1-enyl)benzene. The resulting green oil was purified by preparative thin layer chromatography (5% EtOAc/hexane) to afford 11q (6.0 mg, 0.0297 mmol, 59% yield) in >98:<2 Z:E ratio as colorless oil. The spectral data for this compound were identical to those reported previously (Zhang, X.-G.; Chen, M.-W.; Zhong, P.; Hu, M-.L. *J. Fluorine Chem.* 2008, 129, 335-342).

(Z)-5-(3,3,3-Trifluoroprop-1-enyl)benzo[b]thiophene (11r)

Following the general procedure, a solution of Mo-2d in benzene (0.1 M, 25 μL, 2.5 μmol, 5 mol %) was transferred by syringe to an oven-dried vial containing Z-1,1,1,4,4,4-hexafluoro-2-butene (81.9 mg, 0.499 mmol, 10.0 equiv) and (Z)-5-(3-methylbut-1-enyl)benzo[b]thiophene (10.1 mg, 0.0499 mmol, 1.0 equiv). The resulting solution was allowed to stir for 12 h at 22° C. The reaction was quenched by addition of wet CDCl$_3$ and analysis of the unpurified mixture revealed 90% consumption of (Z)-5-(3-methylbut-1-enyl) benzo[b]thiophene. The resulting green oil was purified by preparative thin layer chromatography (100% hexane) to afford 11r (7.0 mg, 0.0307 mmol, 61% yield) in >98:<2 Z:E ratio as colorless oil. $^1$H NMR (400 MHz, CDCl$_3$): Z isomer (major): δ 7.89-7.86 (2H, m), 7.48 (1H, d, J=5.5 Hz), 7.39 (1H, d, J=8.4 Hz), 7.36 (1H, d, J=5.5 Hz), 7.05 (1H, d, J=12.6 Hz), 5.80 (1H, dq, J=12.9, 9.1 Hz).

tert-Butyl (Z)-5-(3,3,3-trifluoroprop-1-en-1-yl)-1H-indole-1-carboxylate (11s)

Following the general procedure, a solution of Mo-2d in benzene (0.1 M, 20 μL, 2.0 μmol, 5 mol %) was transferred by syringe to an oven-dried vial containing Z-1,1,1,4,4,4-hexafluoro-2-butene (65.6 mg, 0.400 mmol, 10.0 equiv) and tert-butyl (Z)-5-(3-methylbut-1-en-1-yl)-1H-indole-1-carboxylate (11.4 mg, 0.0400 mmol, 1.0 equiv). The resulting solution was allowed to stir for 12 h at 22° C. The reaction was quenched by addition of wet CDCl$_3$ and analysis of the unpurified mixture revealed 92% consumption of tert-butyl (Z)-5-(3-methylbut-1-en-1-yl)-1H-indole-1-carboxylate. The resulting green oil was purified by preparative thin layer chromatography (5% EtOAc/hexane) to afford 11s (8.0 mg, 0.0257 mmol, 64% yield) in >98:2 Z:E ratio as colorless oil. $^1$H NMR (400 MHz, CDCl$_3$): δ 8.12 (1H, d, J=8.7 Hz), 7.64 (1H, s), 7.62 (1H, d, J=3.7 Hz), 7.39-7.34 (1H, m), 7.02 (1H, d, J=12.6 Hz), 6.59 (1H, dt, J=3.7, 0.9 Hz), 5.74 (1H, dqd, J=12.6, 9.2, 0.8 Hz), 1.68 (9H, s).

(Z)-Methyl 2-methoxy-4-(3,3,3-trifluoroprop-1-enyl)benzoate (15)

Following the general procedure, a solution of Mo-2d in benzene (0.1 M, 30 μL, 3.0 μmol, 10 mol %) was transferred by syringe to an oven-dried vial containing Z-1,1,1,4,4,4-hexafluoro-2-butene (49.0 mg, 0.299 mmol, 10.0 equiv) and (Z)-methyl 2-methoxy-4-(3-methylbut-1-enyl)benzoate (7.0 mg, 0.0299 mmol, 1.0 equiv). The resulting solution was allowed to stir for 12 h at 22° C. The reaction was quenched by addition of wet CDCl$_3$ and analysis of the unpurified mixture revealed 82% consumption of (Z)-methyl 2-methoxy-4-(3-methylbut-1-enyl)benzoate. The resulting green oil was purified by silica gel chromatography (5% EtOAc/hexane to 10% EtOAc/hexane) to afford 15 (4.1 mg, 0.0158 mmol, 53% yield) in >98:<2 Z:E ratio as colorless oil. $^1$H NMR (400 MHz, CDCl$_3$): Z isomer (major): δ 7.79 (1H, d, J=8.0 Hz), 7.01 (1H, s), 6.98 (1H, d, J=8.1 Hz), 6.94 (1H, d, J=12.7 Hz), 5.93-5.80 (1H, m), 3.92 (3H, s), 3.90 (3H, s).

(2S,4R)-tert-Butyl 2-((tert-butyldmethylsilyloxy) methyl)-4((Z)-3,3,3-trifluoroprop-1-enyl)pyrrolidine-1-carboxylate (19)

Following the general procedure, a solution of Mo-2d in benzene (0.1 M, 15 μL, 1.5 μmol, 5 mol %) was transferred by syringe to an oven-dried vial containing Z-1,1,1,4,4,4-hexafluoro-2-butene (49.4 mg, 0.301 mmol, 10.0 equiv) and (2S,4R)-tert-butyl 2-((tert-butyldimethylsilyloxy)methyl)-4-((Z)-prop-1-enyl)pyrrolidine-1-carboxylate (10.7 mg, 0.0301 mmol, 1.0 equiv). The resulting solution was allowed to stir for 4 hours at 22° C. The reaction was quenched by addition of wet CDCl$_3$ and analysis of the unpurified mixture revealed >98% consumption of (2S,4R)-tert-butyl 2-((tert-butyldimethylsilyloxy)methyl)-4-((Z)-prop-1-enyl)pyrrolidine-1-carboxylate. The resulting green oil was purified by silica gel chromatography (1% EtOAc/hexane to 4% EtOAc/hexane) to afford 19 (10.4 mg, 0.0254 mmol, 84% yield) in >98:<2 Z:E ratio as colorless oil. $^1$H NMR (400 MHz, CDCl$_3$): Z isomer (major): δ 5.88 (1H, dd, J=11.5, 10.3 Hz), 5.65 (1H, dq, J=11.9, 8.4 Hz), 4.01-3.60 (4H, m), 3.22 (1H, dd, J=18.1, 9.3 Hz), 2.92 (1H, t, J=10.3 Hz), 2.29-2.12 (1H, m), 1.96-1.80 (1H, m), 1.46 (9H, s), 0.88 (9H, s), 0.04 (6H, d, J=3.0 Hz).

(Z)-tert-Butyl 4-(tert-butyldimethylsilyloxy)-3-methoxybenzyl(8,8,8-trifluorooctan-6-enoyl)carbamate (21)

Following the general procedure, a solution of Mo-2d in benzene (0.1 M, 15 μL, 1.5 μmol, 5 mol %) was transferred by syringe to an oven-dried vial containing Z-1,1,1,4,4,4-hexafluoro-2-butene (49.2 mg, 0.300 mmol, 10.0 equiv) and (Z)-tert-butyl 4-(tert-butyldimethylsilyloxy)-3-methoxybenzyl(8-methylnon-6-enoyl)carbamate (15.6 mg, 0.0300 mmol, 1.0 equiv). The resulting solution was allowed to stir for 4 h at 22° C. The reaction was quenched by addition of wet CDCl$_3$ and analysis of the unpurified mixture revealed >98% consumption of (Z)-tert-butyl 4-(tert-butyldimethylsilyloxy)-3-methoxybenzyl(8-methylnon-6-enoyl)carbamate. The resulting green oil was purified by silica gel chromatography (2% EtOAc/hexane to 4% EtOAc/hexane) to afford 21 (14.1 mg, 0.0258 mmol, 86% yield) in >98:<2 Z:E ratio as colorless oil. $^1$H NMR (400 MHz, CDCl$_3$): Z isomer (major): δ 6.76 (2H, d, J=8.1 Hz), 6.73-6.66 (1H, m), 5.98 (1H, dt, J=11.5, 7.8 Hz), 5.66-5.50 (1H, m), 4.79 (2H, s), 3.76 (3H, s), 2.90 (2H, t, J=7.3 Hz), 2.36-2.27 (2H, m), 1.75-1.64 (2H, m), 1.52-1.44 (2H, m), 1.42 (9H, s), 0.98 (9H, s), 0.13 (6H, s).

(Z)-5,5,5-Trifluoropent-3-enyl (2S,5R)-3,3-dimethyl-7-oxo-4-thia-1-azabicyclo[3.2.0]heptane-2-carboxylate 4,4-dioxide (23)

Following the general procedure, a solution of Mo-2d in benzene (0.1 M, 20 μL, 2.0 μmol, 5 mol %) was transferred by syringe to an oven-dried vial containing Z-1,1,1,4,4,4-hexafluoro-2-butene (32.8 mg, 0.200 mmol, 5.0 equiv) and (Z)-hex-3-enyl (2S,5R)-3,3-dimethyl-7-oxo-4-thia-1-azabicyclo[3.2.0]heptane-2-carboxylate 4,4-dioxide (12.6 mg, 0.0400 mmol, 1.0 equiv). The resulting solution was allowed to stir for 2 h at 22° C. The reaction was quenched by addition of wet CDCl$_3$ and analysis of the unpurified mixture revealed 86% consumption of (Z)-hex-3-enyl (2S,5R)-3,3-dimethyl-7-oxo-4-thia-1-azabicyclo[3.2.0]heptane-2-carboxylate 4,4-dioxide. The resulting green oil was purified by silica gel chromatography (20% EtOAc/hexane to 30% EtOAc/hexane) to afford 23 (11.8 mg, 0.0332 mmol, 83% yield) in >98:<2 Z:E ratio as colorless oil. $^1$H NMR (400 MHz, CDCl$_3$): δ 5.99 (1H, dt, J=11.7, 7.7 Hz), 5.85-5.72 (1H, m), 4.60 (1H, dd, J=4.0, 2.3 Hz), 4.38 (1H, s), 4.31 (2H, t, J=6.3 Hz), 3.47 (2H, dd, J=5.0, 3.2 Hz), 2.78-2.67 (2H, m), 1.60 (3H, s), 1.41 (3H, s).

(Z)-5,5,5-Trifluoropent-3-en-1-yl 24(Z)-5-((E)-2-methyl-3-phenylallylidene)-4-oxo-2-thioxothiazolidin-3-yl)acetate (24)

Following the general procedure, a solution of Mo-2c in benzene (0.1 M, 10 μL, 1.0 μmol, 5 mol %) was transferred by syringe to an oven-dried vial containing Z-1,1,1,4,4,4- hexafluoro-2-butene (16.2 mg, 0.100 mmol, 5.0 equiv) and (Z)-pent-3-en-1-yl 2-((Z)-5-((E)-2-methyl-3-phenylallylidene)-4-oxo-2-thioxothiazolidin-3-yl)acetate (8.0 mg, 0.0200 mmol, 1.0 equiv). The resulting solution was allowed to stir for 4 h at 22° C. The reaction was quenched by addition of wet CDCl$_3$ and analysis of the unpurified mixture revealed >98% consumption of (Z)-pent-3-en-1-yl 2-((Z)-5-((E)-2-methyl-3-phenylallylidene)-4-oxo-2-thioxothiazolidin-3-yl)acetate. The resulting green oil was purified by silica gel chromatography (10% Et$_2$O/pentane to 20% Et$_2$O/pentane) to afford 24 (8.1 mg, 0.0183 mmol, 92% yield) in >98:2 Z:E ratio as yellow oil. $^1$H NMR (400 MHz, CDCl$_3$): δ 7.57 (1H, d, J=1.0 Hz), 7.45-7.32 (5H, m), 7.09 (1H, s), 6.00 (1H, dt, J=11.7, 7.6 Hz), 5.74 (1H, dtdd, J=11.7, 8.4, 6.7, 1.8 Hz), 4.86 (2H, s), 4.27 (2H, t, J=6.3 Hz), 2.68 (2H dtq, J=10.4, 6.3, 2.1 Hz), 2.26 (3H, d, J=1.3 Hz).

Artesunate (Z)-5,5,5-trifluoropent-3-enyl ester (25)

Following the general procedure, a solution of Mo-2d in benzene (0.1 M, 15 µL, 1.5 µmol, 5 mol %) was transferred by syringe to an oven-dried vial containing Z-1,1,1,4,4,4-hexafluoro-2-butene (49.2 mg, 0.150 mmol, 5.0 equiv), artesunate (Z)-hex-3-enyl ester (14.0 mg, 0.0300 mmol, 1.0 equiv) and toluene (45 µL). The resulting solution was allowed to stir for 4 h at 22° C. The reaction was quenched by addition of wet CDCl$_3$ and analysis of the unpurified mixture revealed 86% consumption of artesunate (Z)-hex-3-enyl ester. The resulting green oil was purified by silica gel chromatography (10% EtOAc/hexane to 20% EtOAc/hexane) to afford 25 (12.3 mg, 0.0243 mmol, 81% yield) in >98:<2 Z:E ratio as colorless oil. $^1$H NMR (400 MHz, CDCl$_3$): Z isomer (major): δ 6.03 (1H, dt, J=11.7, 7.7 Hz), 5.79 (1H, d, J=9.9 Hz), 5.77-5.67 (1H, m), 5.43 (1H, s), 4.18 (2H, t, J=6.4 Hz), 2.76-2.53 (8H, m), 2.38 (1H, ddd, J=14.5, 13.4, 4.0 Hz), 2.03 (1H, ddd, J=14.7, 4.6, 3.0 Hz), 1.93-1.85 (1H, m), 1.80-1.69 (2H, m), 1.62 (1H, dt, J=13.9, 4.4 Hz), 1.43 (3H, s), 1.39-1.25 (4H, m), 0.96 (3H, d, J=6.0 Hz), 0.85 (3H, d, J=7.1 Hz).

Experimental Procedure for Z-Selective Cross-Metathesis of Monosubstituted Alkenes with Mo-1b and Mo-2d (Two-Catalyst Approach):

A solution of Mo-1b in benzene (0.1 M, 5 µL, 0.5 µmol, 1 mol %) was transferred by syringe to an oven-dried vial containing a solution of Z-2-butene in toluene (3.0 M, 85 µL, 0.250 mmol, 5.0 equiv) and 8-bromo-1-octene (9.6 mg, 0.0500 mmol, 1.0 equiv). The resulting solution was allowed to stir for 1 h at 22° C. then filtered through a short pad of silica gel and concentrated in vacuo. Percent conversion and $^1$H NMR yield were determined by 400 MHz $^1$H NMR analysis of the unpurified mixture. Z:E ratio was calculated based on $^{19}$F NMR analysis of the unpurified mixture. Conversion of 8-bromo-1-octene was determined to be 94%. $^1$H NMR yield of 9-bromonon-2-ene was determined to be 90%. Z:E ratio was determined to be 88:12.

A solution of Mo-2d in benzene (0.1 M, 16 µL, 1.6 µmol, 5 mol %) was transferred by syringe to an oven-dried vial containing Z-1,1,1,4,4,4-hexafluoro-2-butene (26.2 mg, 0.160 mmol, 5.0 equiv) and the crude 9-bromonon-2-ene obtained above (6.4 mg, 0.0320 mmol, 1.0 equiv). The resulting solution was allowed to stir for 4 h at 22° C. The reaction was quenched by addition of wet CDCl$_3$ and analysis of the unpurified mixture revealed >98% consumption of 9-bromonon-2-ene. $^1$H NMR yield of (Z)-9-bromo-1,1,1-trifluoronon-2-ene was determined to be 66%. Z:E ratio was determined to be 95:5.

Experimental Procedure for Z-Selective Cross-Metathesis of Monosubstituted Alkenes with Mo-2e (Single-Catalyst Approach)

In a N$_2$-filled glove box, Mo-2e (2.70 mg, 2.5 µmol, 0.05 equiv.) and Ph$_3$CB(C$_6$F$_5$)$_4$ (2.77 mg, 3.0 µmol, 0.06 equiv.) in 50 µL of C$_6$D$_6$ were allowed to stir for 10 min in an oven-dried 1.9 ml vial equipped with a magnetic stir bar. To this vessel, 1-octene (7.85 µL, 5.61 mg, 50.0 µmol, 1.0 equiv) was added via micro syringe. The resulting solution was allowed to stir without cap under N$_2$ for 20 minutes. Z-1,1,1,4,4,4-Hexafluoro-2-butene (11.7 µL, 100.0 µmol, 2.0 equiv) was subsequently added via micro syringe and the vial was sealed tightly. The resulting dark brown solution was allowed to stir for 16 h. 0.5 ml of C$_6$D$_6$ was added and the resulting solution was transferred to an NMR tube. Percent conversion and $^1$H NMR yield were determined by 400 MHz $^1$H NMR analysis of the unpurified mixture. Z:E ratio was calculated based on $^{19}$F NMR analysis of the unpurified mixture. Conversion of 1-octene was determined to be >98%. $^1$H NMR yield of 1,1,1-trifluoronon-2-ene was determined to be >98%. Z:E ratio was determined to be 73:27.

The invention claimed is:

1. A method for performing an alkene metathesis reaction, comprising:
   reacting a first species comprising a first carbon to carbon double bond with a second species comprising a second carbon to carbon double bond in the presence of a compound of formula I-a, to provide at least one product comprising a third carbon to carbon double bond, wherein:
   a carbon atom of the first carbon to carbon double bond in the first species is substituted with a first substituent selected from halogen and optionally substituted $C_{1-6}$ haloalkyl; and
   the third carbon to carbon double bond in the at least one product comprises a carbon atom of the first carbon to carbon double bond and a carbon atom of the second carbon to carbon double bond, wherein the carbon atom of the first carbon to carbon double bond is substituted with the first substituent;
   wherein each carbon atom of the first carbon to carbon double bond in the first species is independently substituted with the first substituent;
   wherein the first species is

wherein each of X and Y is independently halogen or independently optionally substituted $C_{1-6}$ haloalkyl; or
   wherein

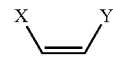

is cis-1,2-dichloroethene or cis 1,2-dibromoethene or cis-1,1,1,4,4,4-hexafluoro-2-butene; or
   wherein a carbon atom of the first carbon to carbon double bond in the first species is independently substituted with an optionally substituted $C_{1-6}$ haloalkyl group, and the at least one product comprises a third carbon to carbon double bond substituted with the optionally substituted $C_{1-6}$ haloalkyl group, and wherein the optionally substituted $C_{1-6}$ haloalkyl is methyl substituted with one to three halogens, wherein the optionally substituted $C_{1-6}$ haloalkyl comprises one or more —F; or wherein the optionally substituted $C_{1-6}$ haloalkyl is methyl substituted with one to three halogens, wherein at least one halogen is —F; or wherein the optionally substituted $C_{1-6}$ haloalkyl is —CH$_2$F, —CHF$_2$, —CClF$_2$, —CF$_3$, —C$_2$F$_5$, —C$_3$F$_7$, —C$_4$F$_9$, —C$_5$F$_{11}$, or —C$_6$F$_{13}$;

wherein the alkene metathesis reaction is a Z-selective cross-metathesis reaction or a Z-selective ring-opening cross metathesis reaction; and wherein the compound of formula I-a is:

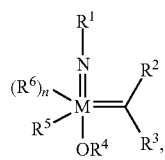

I-a

M is molybdenum;

wherein:

$R^1$ is adamantyl, tert-butyl, 2,6-dichlorophenyl, 2,6-dibromophenyl, 2,6-dimethylphenyl, 2,6-di-t-butylphenyl, 2,6-diisopropylphenyl, or pentafluorophenyl;

one of $R^2$ and $R^3$ is hydrogen and the other is —C(Me)$_3$ or is —C(Me)$_2$Ph or is phenyl or 2-methoxyphenyl or 2-isopropoxyphenyl;

$R^4$ is 2,6-(2,6-dimethylphenyl)$_2$C$_6$H$_3$, 2,6-(mesityl)$_2$C$_6$H$_3$, 2,6-(2,6-diethylphenyl)$_2$C$_6$H$_3$, 2,6-(2,4,6-triethylphenyl)$_2$C$_6$H$_3$, 2,6-(2,6-diisopropylphenyl)$_2$C$_6$H$_3$, 2,6-(2,4,6-triisopropylphenyl)$_2$C$_6$H$_3$, 2,6-(2,6-di-t-butylphenyl)$_2$C$_6$H$_3$, 2,6-(2,4,6-tri-t-butylphenyl)$_2$C$_6$H$_3$, 2,6-(2,6-diphenylphenyl)$_2$C$_6$H$_3$, 2,6-(2,4,6-triphenylphenyl)$_2$C$_6$H$_3$, 2,6-(3,5-di-t-butylphenyl)$_2$C$_6$H$_3$, 2,6-(2,6-dichlorphenyl)$_2$C$_6$H$_3$, 2,6-(2,4,6-trichlorophenyl)$_2$C$_6$H$_3$, 2,4,6-(mesityl)$_3$C$_6$H$_2$, 2,3,5,6-(phenyl)$_4$C$_6$H, or 2,3,4,5,6-(phenyl)$_5$C$_6$;

$R^5$ is —Cl or Br;

$R^6$ is selected from the group consisting of an ether, a nitrile, a phosphine, a pyridine, and an amine; and n is 0-2.

2. The method of claim 1, wherein the method is performed in the presence of a compound selected from the group consisting of: trityl tetrakis(pentafluorophenyl)borate [(C$_6$H$_5$)$_3$CB(C$_6$F$_5$)$_4$], sodium tetrakis[3,5-bis(trifluoromethyl)phenyl]borate [Na(B[3,5-(CF$_3$)$_2$C$_6$H$_3$]$_4$)], tris(pentafluorophenyl)boron [B(C$_6$F$_5$)$_3$], dimethylanilinium tetrakis(pentafluorophenyl) borate [PhNMe$_2$HB(C$_6$F$_5$)$_4$], and CuCl.

3. The method of claim 1, wherein the compound of formula I-a is selected from:

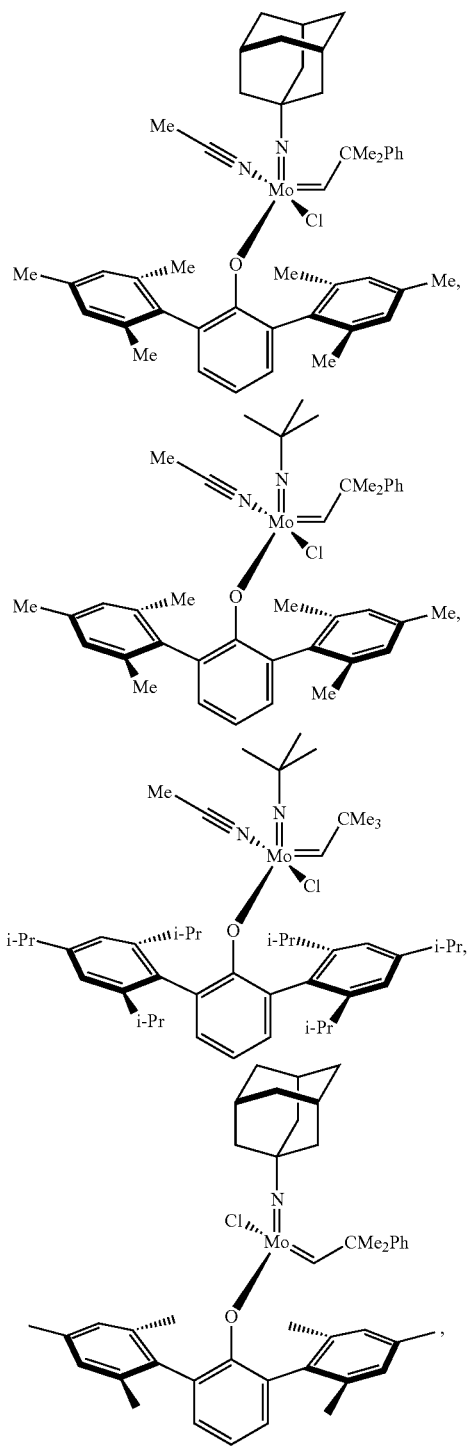

Mo(NAd)(CHCMe$_2$Ph)(OHMT)(Br)(py), Mo(NAd)(CHR)(OHMT)(Cl)(py), Mo(NAd)(CHR)(OHMT)(Br)(MeCN), Mo(NAd)(CHR)(OHMT)(Cl)(MeCN), Mo(NC$_6$F$_5$)(CHR)(OHMT)(Br)(py), Mo(NC$_6$F$_5$)(CHR)(OHMT)(Cl)(py), Mo(N-t-Bu)(CHCMe$_2$Ph)(OHMT)(Cl)(MeCN), Mo(N-t-Bu)(CHCMe$_2$Ph)(OHIPT)(Cl)(MeCN), Mo(N-t-Bu)(CHCMe$_2$Ph)(OTBT)(Cl)(MeCN), Mo(NAd)(CHR)(OHMT)(Br), Mo(NAd)(CHR)(OHMT)(Cl)(ADNH$_2$), Mo(N-t-Bu)(CHt-Bu)(OHMT)(Cl)(MeCN), Mo(N-t-Bu)(CHt-Bu)(OHMT)(Br)(MeCN), Mo(N-t-Bu)(CHt-Bu)(OHIPT)(Cl)

(MeCN), Mo(NC$_6$F$_5$)(CHR)(OHMT)(Cl)(PhMe$_2$P), Mo(NC$_6$F$_5$)(CHR)(OHIPT)(Cl)(PhMe$_2$P), and Mo(NC$_6$F$_5$)(CHR)(OHMT)(Cl)(Me$_3$P), wherein Ad is adamant-1-yl, AdNH$_2$ is 1-amino-adamantane, py is pyridine, Ph is phenyl, Me is methyl, R is —CMe$_2$Ph, OHMT is O-2,6-(mesityl)$_2$C$_6$H$_3$, OHIPT is O-2,6-(2,4,6-(i-Pr)$_3$C$_6$H$_2$)$_2$C$_6$H$_3$, and OTBT is O-2,6-(3,5-(di-t-Bu-phenyl)$_2$C$_6$H$_3$).

\* \* \* \* \*